US008900124B2

(12) United States Patent
Hirakawa

(10) Patent No.: US 8,900,124 B2
(45) Date of Patent: Dec. 2, 2014

(54) IMAGE DISPLAY DEVICE

(75) Inventor: Katsumi Hirakawa, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 1815 days.

(21) Appl. No.: 11/888,871

(22) Filed: Aug. 2, 2007

(65) Prior Publication Data

US 2008/0039692 A1    Feb. 14, 2008

(30) Foreign Application Priority Data

Aug. 3, 2006  (JP) .................. 2006-212510
Sep. 5, 2006  (JP) .................. 2006-240384

(51) Int. Cl.
*A61B 1/04* (2006.01)
*A61B 1/00* (2006.01)

(52) U.S. Cl.
CPC ............... *A61B 1/04* (2013.01); *A61B 1/00045* (2013.01); *A61B 1/041* (2013.01)
USPC ............................ 600/109; 348/65

(58) Field of Classification Search
USPC ................ 600/103, 109, 160; 348/65, 71
See application file for complete search history.

(56) References Cited

U.S. PATENT DOCUMENTS

| 2004/0225223 | A1  | 11/2004 | Honda et al. |
| 2004/0249291 | A1  | 12/2004 | Honda et al. |
| 2005/0007551 | A1  | 1/2005  | Wakil et al. |
| 2005/0075551 | A1* | 4/2005  | Horn et al. ............ 600/361 |
| 2006/0074275 | A1* | 4/2006  | Davidson et al. ........ 600/160 |
| 2009/0135249 | A1  | 5/2009  | Hirakawa |

FOREIGN PATENT DOCUMENTS

| JP | 11-288426  | A | 10/1999 |
| JP | 11-328209  | A | 11/1999 |
| JP | 2000-172401| A | 6/2000  |
| JP | 2003-019111|   | 1/2003  |
| JP | 2004-337596|   | 12/2004 |
| JP | 2005-107867| A | 4/2005  |
| JP | 2006-061469| A | 3/2006  |
| JP | 2006-138957| A | 6/2006  |

(Continued)

OTHER PUBLICATIONS

Japanese Office Action dated Jan. 4, 2012 from corresponding Japanese Patent application No. JP 2006-212510 together with English language translation.

(Continued)

*Primary Examiner* — John P Leubecker
(74) *Attorney, Agent, or Firm* — Scully, Scott, Murphy & Presser, PC

(57) ABSTRACT

A device for displaying in vivo images picked up inside a subject in a time series. The device automatically detects lesion images contained in all in vivo images picked up over the time series. The device displays an elongated display area having a time scale assigned along a longitudinal direction thereof and an indicator which moves along the time scale to indicate a time position in the time scale which corresponds to a current in vivo image currently displayed in a main display area. In response to a detection of the lesion image, the device makes pixels located at a time position in the elongated display area which position corresponds to the lesion image to emit light in a predetermined pixel-display mode. The display mode of the indicator is controlled in response to information on a lesion that is possible to be contained in the current in vivo image.

11 Claims, 33 Drawing Sheets

(56) References Cited

FOREIGN PATENT DOCUMENTS

| | | |
|---|---|---|
| JP | 2006-149684 A | 6/2006 |
| JP | 2007-507277 A | 3/2007 |
| WO | WO 2005/031650 A1 | 4/2005 |
| WO | WO 2006/019120 A1 | 2/2006 |

OTHER PUBLICATIONS

Decision of a Patent Grant dated Jan. 4, 2012 from corresponding Japanese Patent application No. JP 2006-240384 together with English language translation.

English language abstract only of International Publication No. WO 2005/031650 A1.

* cited by examiner

FIG.20
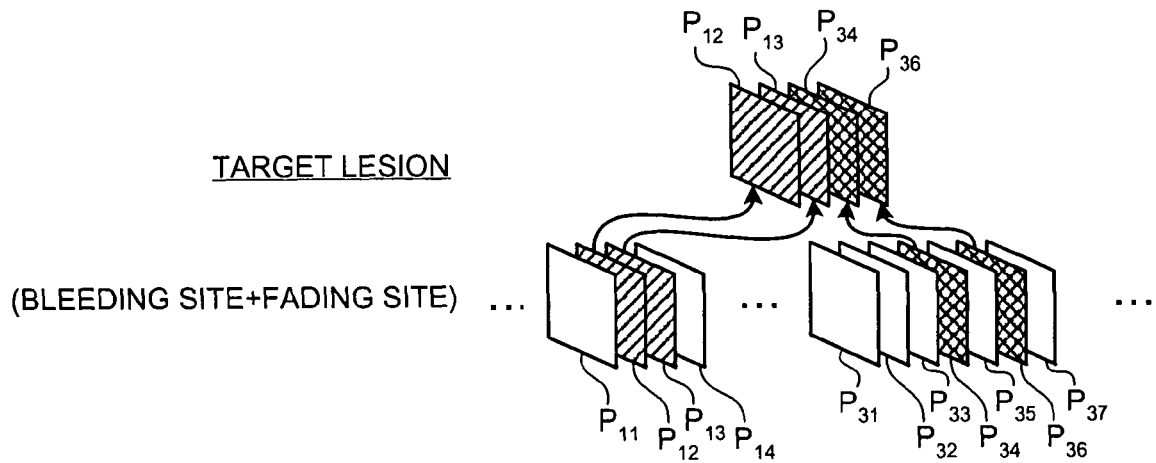
TARGET LESION
(BLEEDING SITE+FADING SITE)
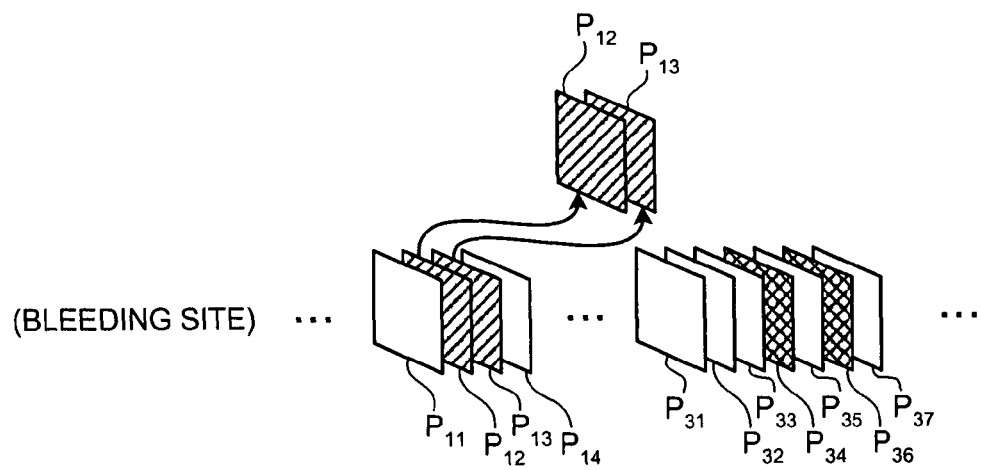
(BLEEDING SITE)
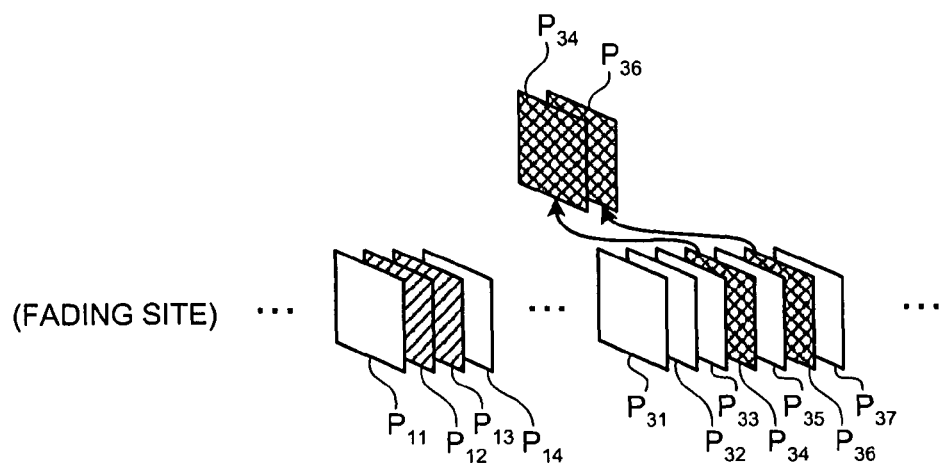
(FADING SITE)

IMAGE DISPLAY DEVICE

CROSS-REFERENCE TO RELATED APPLICATIONS

This application is based upon and claims the benefit of priority from Japanese Patent Application No. 2006-212510, filed Aug. 3, 2006; and Japanese Patent Application No. 2006-240384, filed Sep. 5, 2006, the entire contents of both of which are incorporated herein by reference.

BACKGROUND OF THE INVENTION

1. Field of the Invention

The present invention relates to an image display device that displays each image contained in a group of images picked up in a time series inside a subject or a patient's body.

2. Description of the Related Art

In the field of endoscope, capsule endoscopes of swallow-type equipped with an imaging function and radio communication function have been proposed and in-vivo information acquiring systems for acquiring a group of images inside organs by inserting such a capsule endoscope into the organs of a subject have been developed. A capsule endoscope is swallowed through the month of a subject such as a patient to make observations (examinations) inside the organs. Then, the capsule endoscope moves through organs such as stomach and small intestine due to peristaltic movement or the like until the capsule endoscope is naturally discharged from the subject while at the same time successively picking up images inside organs of the subject (hereinafter sometimes referred to as images inside the subject) at intervals, for example, of 0.5 seconds in a time series.

While the capsule endoscope moves through organs of the subject, images inside the organs picked up by the capsule endoscope are successively transmitted by radio communication to an external receiving device. The receiving device has a receiving antenna and storage medium and functions so as to receive images inside organs transmitted from the relevant capsule endoscope and to successively store the received images inside organs. By carrying such a receiving device, the subject can move about freely throughout a period between a time when a capsule endoscope is swallowed and a time when the capsule endoscope is naturally discharged.

After the capsule endoscope is naturally discharged, a user such as a physician and nurse causes an image display device to capture a group of images inside organs stored in the storage medium of the relevant receiving device to successively display the group of images inside organs on a display monitor of the image display device. The user successively observes the group of images inside the subject being displayed by the image display device so as to be able to diagnose the subject (Refer, for example, to Japanese Patent Application Laid-Open No. 2003-19111).

Some of such image display devices display a time bar that shows images inside organs picked up by a capsule endoscope in a time series and time positions of the whole group of images inside organs and, if there is any bleeding site image (hereinafter referred to as a bleeding image) among the images inside organs, a mark indicating the time position of such a bleeding image is attached onto the time bar (Refer, for example, to Japanese Patent Application Laid-Open No. 2004-337596). An image display device described in this Patent Document 2 detects color information of a group of images inside organs and, based on the detected color information, detects bleeding images from among the group of images inside organs. Such an image display device displays a mark indicating the time position of a bleeding image (hereinafter sometimes referred to as a lesion mark) at positions on the time bar corresponding to the bleeding images detected from among the group of images inside organs. By visually confirming such a lesion mark displayed on the time bar, a user such as a physician and nurse can easily conjecture in which organ of a subject bleeding images contained in the group of images inside organs were picked up.

Some other image display devices display bleeding site images extracted from among a group of images inside a subject in a display area and also displays a predetermined mark near the bleeding site images to notify a user such as a physician and nurse that images currently displayed in the display area are bleeding site images.

Meanwhile, the time bar described above is generally formed of a group of picture elements arranged in a line. A picture element inside the group of picture elements forming the time bar represents a continuous image group having a predetermined number of images contained in the group of images inside organs successively displayed by the image display device. If, for example, a time bar is formed of 1,000 picture elements arranged in a line and the time bar of the 1,000 picture elements shows time positions of a whole group of 60,000 images inside organs picked up by a capsule endoscope, one picture element in the time bar of the 1,000 picture elements represents a continuous image group having 60 images contained in the group of 60,000 images inside organs.

A mark attached to such a time bar only indicates a temporal position of an image representing a group of partial images including bleeding images inside a subject. Thus, there has been a problem that, when a slider is moved to the position of a mark attached to the time bar, it is difficult to identify which of a group of partial images displayed in the display area are bleeding images.

If a mark to indicate a bleeding image is additionally displayed near a bleeding image currently displayed in the display area, there has a possibility that observation of images inside a subject displayed in the display area may be disturbed because the mark also comes into view of a user such as a physician and nurse and flickers.

A lesion mark displayed at a time position on the time bar (that is, a position corresponding to one picture element of the time bar), on the other hand, represents one or more bleeding images in a continuous image group having 60 images represented by such a picture element of the time bar. That is, if at least one bleeding image is contained in a continuous image group having 60 images, such a lesion mark is displayed in the same way regardless of the number of bleeding images. Thus, there has been a problem that, although it is possible to understand the time positions of bleeding images contained in a group of images inside organs by such a lesion mark, it is difficult to understand distribution of the numbers of images in the overall time positions of the groups of images inside organs.

SUMMARY OF THE INVENTION

According to an aspect of the invention, an image display device for displaying in vivo images picked up inside a subject in a time series is provided. The image display device comprises an image detector for detecting a lesion image contained in in vivo images picked up over the time series, a fundamental display unit for displaying an elongated display area having a scale assigned along a longitudinal direction thereof and an indicator which moves along the scale to indicate a position in the scale which corresponds to a current one of the all in vivo images which is currently displayed in a main display area, a lesion display unit, responsive to a detection of the lesion image by the image detector, for making pixels located at a position in the elongated display area which position corresponds to the lesion image to emit light in a predetermined pixel-display mode, and a display controlling unit for controlling a display mode of the indicator based on information on a lesion that is possible to be contained in the current in vivo image.

In a preferred embodiment, the fundamental display unit displays a bar which is parallel with the elongated display area so as to align the bar with the elongated display area, and displays the indicator as a slider which is movable along the bar.

The image display device preferably comprises a unit for displaying icons for permitting the user to issue respective display instructions for a next image, a play, a previous image and a reverse play with respect to the current in vivo image, an image display unit, responsive to an operation of one of the icons, for executing a display operation according to a display instruction associated with the one icon, and a unit for permitting the user to select either a normal play mode in which all in vivo images are to be displayed and a lesion play mode in which only the lesion images are to be displayed. The image display unit is preferably adapted to respond to a selection of the normal play mode and set all in vivo images to operation target, and is further adapted to respond to a selection of the lesion play mode and extract lesion images from all in vivo images and setting only the extracted lesion images to the operation target.

The fundamental display unit may be adapted to respond to a determination that the total number of all in vivo images is larger than a pixel number L of pixels along a long side of the elongated display area, to map L continuous image groups into which all in vivo images are divided by the pixel number onto L positions of the scale and to display the indicator at a position corresponding to a continuous image group in which the current in vivo image is included. Further, the lesion display unit may include a lesion mark display unit for making a pixel column at each position in the elongated display area to emit light quantitatively in response to a number of lesion images included in the continuous image group corresponding to the position.

According to another aspect of the invention, an image display method of displaying in vivo images picked up inside a subject in a time series is provide. The image display method comprises the steps of detecting a lesion image contained in in vivo images picked up over the time series; displaying an elongated display area having a scale assigned along a longitudinal direction thereof and an indicator which moves along the scale to indicate a position in the scale which corresponds to a current one of all in vivo images which is currently displayed in a main display area; in response to a detection of the lesion image by the image detector, making pixels located at a position in the elongated display area which position corresponds to the lesion image to emit light in a predetermined pixel-display mode; and controlling a display mode of the indicator in response to information on a lesion that is possible to be contained in the current in vivo image.

The above and other objects, features, and advantages of the present invention will become apparent to those skilled in the art upon consideration of further descriptions provided below with reference to the drawings.

BRIEF DESCRIPTION OF THE DRAWINGS

FIG. 20 is a schematic view illustrating an operation of the control unit displaying in the main display area a lesion image containing the target lesion as a photographic object from among multiple kinds of lesion images;

DETAILED DESCRIPTION OF THE PREFERRED EMBODIMENTS

Figure 1:
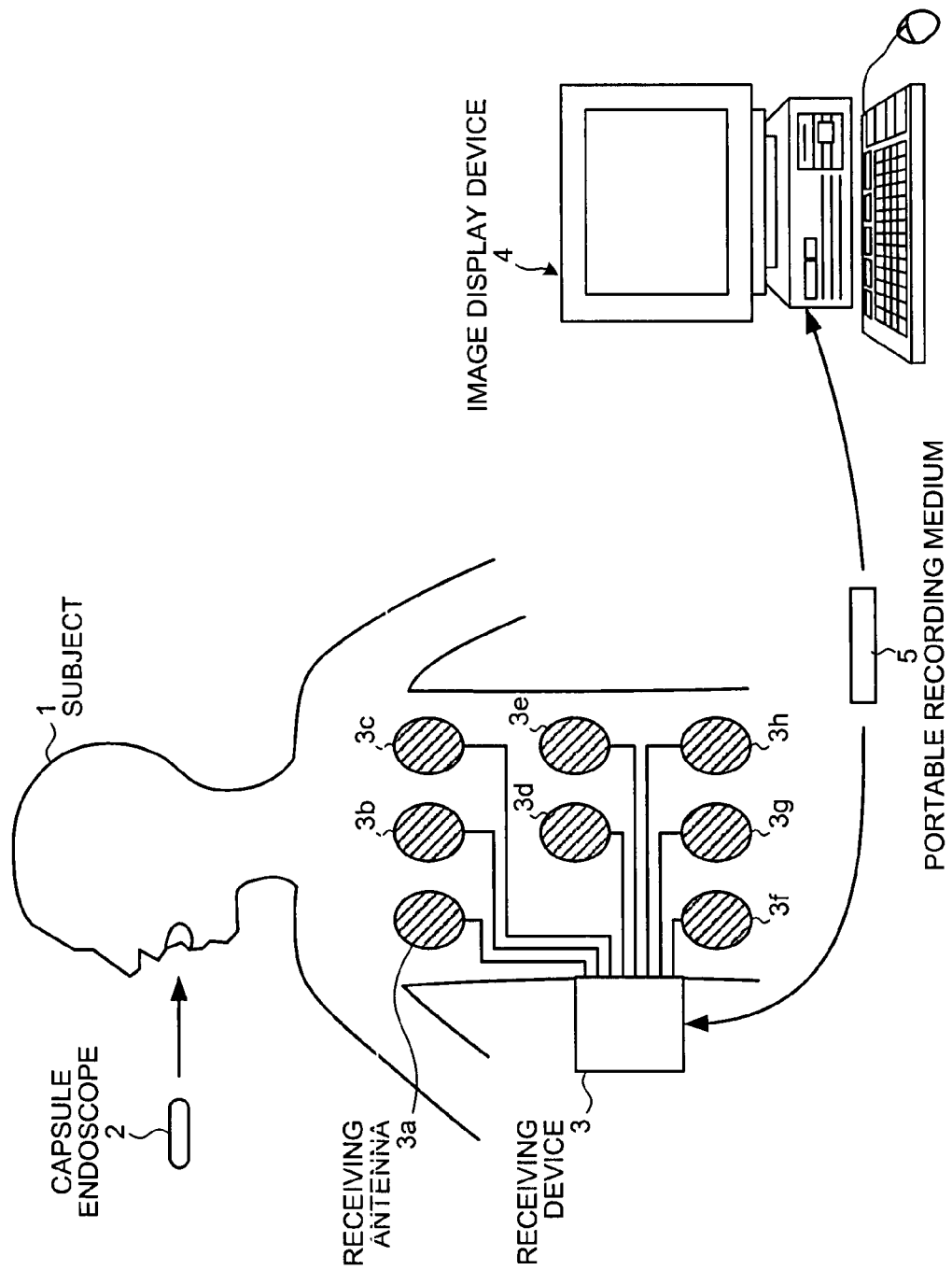
FIG. 1 is a schematic view exemplifying a configuration example of an in-vivo information acquiring system having an image display device according to a first embodiment of the present invention.

Suitable embodiments of the image display device according to the present invention will be described below in detail with reference to drawings. However, the present invention is not limited by preferred embodiments shown below.
First Embodiment FIG. 1 is a schematic view exemplifying a configuration example of an in-vivo information acquiring system having an image display device according to a first embodiment of the present invention. As shown in FIG. 1, the in-vivo information acquiring system according to the first embodiment of the present invention comprises a capsule endoscope 2 for picking up images inside a subject 1, a receiving device 3 for receiving images inside the subject 1 picked up by the capsule endoscope 2, an image display device 4 for displaying an image inside the subject 1 received by the receiving device 3, and a portable recording medium 5 for exchanging data between the receiving device 3 and image display device 4.

The capsule endoscope 2 is used to pick up images inside a subject (more specifically, images inside organs). The capsule endoscope 2 has an imaging function, after being introduced into the subject 1, to successively pick up images inside the subject 1 in a time series and a radio communication function to transmit all in vivo images AI to the external receiving device 3 by radio. More specifically, after being swallowed by the subject 1, the capsule endoscope 2 moves through organs of the subject 1 due to peristaltic movement or the like of organs of the subject 1. At the same time, the capsule endoscope 2 sequentially picks up images inside the subject 1 at predetermined intervals, for example, of 0.5 seconds and sequentially transmits radio signals including images picked up inside the subject 1 to the receiving device 3.

The receiving device 3 has a plurality of receiving antennas 3a to 3h, for example, spread out over a body surface of the subject 1 and connected to the receiving device 3 to receive radio signals from the capsule endoscope 2 via any of the plurality of receiving antennas 3a to 3h. Then, the receiving device 3 acquires all in vivo images AI based on radio signals received from the capsule endoscope 2. The portable recording medium 5 is also detachably inserted into the receiving device 3 to store all of the images picked up inside the subject 1 by the capsule endoscope 2, which are referred to as "all in vivo images AI". In this case, the receiving device 3 stores in the portable recording medium 5 time information showing an imaging time or receiving time of each image contained in all in vivo images AI in association with time information with the received image.

The receiving antennas 3a to 3h are realized, for example, by using a loop antenna and receive radio signals transmitted by the capsule endoscope 2. As shown in FIG. 1, the receiving antennas 3a to 3h are spread out at predetermined locations on the body surface of the subject 1, for example, locations corresponding to a passage route (that is, the digestive tract) of the capsule endoscope 2 inside the subject 1. The receiving antennas 3a to 3h may also be spread out at predetermined position on a jacket to be worn by the subject 1. In this case, the receiving antennas 3a to 3h are spread out at predetermined locations on the body surface of the subject 1 corresponding to the passage route of the capsule endoscope 2 inside the subject 1 when the subject 1 wears the jacket. At least one such antenna needs to be arranged for the subject 1 and its number is not particularly limited to 8.

The portable recording medium 5 is a recording medium that can be carried such as CompactFlash (registered trademark). The portable recording medium 5 has a structure so that the portable recording medium 5 can be inserted/detached into/from the receiving device 3 and image display device 4 and, when inserted, data can be output and recorded. More specifically, when inserted in the receiving device 3, the portable recording medium 5 sequentially stores various kinds of data on one or more sets of all in vivo images AI received by the receiving device 3 and time information of each image. When inserted in the image display device 4, on the other hand, the portable recording medium 5 outputs stored data concerning all in vivo images and time information of each image to the image display device 4. Data stored in the portable recording medium 5 is captured in this way by the image display device 4. Also, patient information or the like about the subject 1 into which the capsule endoscope 2 is introduced is written into the portable recording medium 5 by the image display device 4.

The image display device 4 is used to display images inside the subject 1 picked up by the capsule endoscope 2. More specifically, the image display device 4 has a structure like a workstation so that various kinds of data concerning, for example, all in vivo images AI are acquired by capturing the stored data in the portable recording medium 5 to display each image contained in all in vivo images AI. The image display device 4 has a processing function to enable a user such as a physician or nurse to diagnose the subject 1 by observing (examining) images inside the subject 1. In this case, the user causes the image display device 4 to successively display images inside the subject 1 to observe (examine) in-vivo regions such as esophagus, stomach, small intestine, and large intestine before diagnosing the subject 1 based on the observation (examination).

Figure 2:
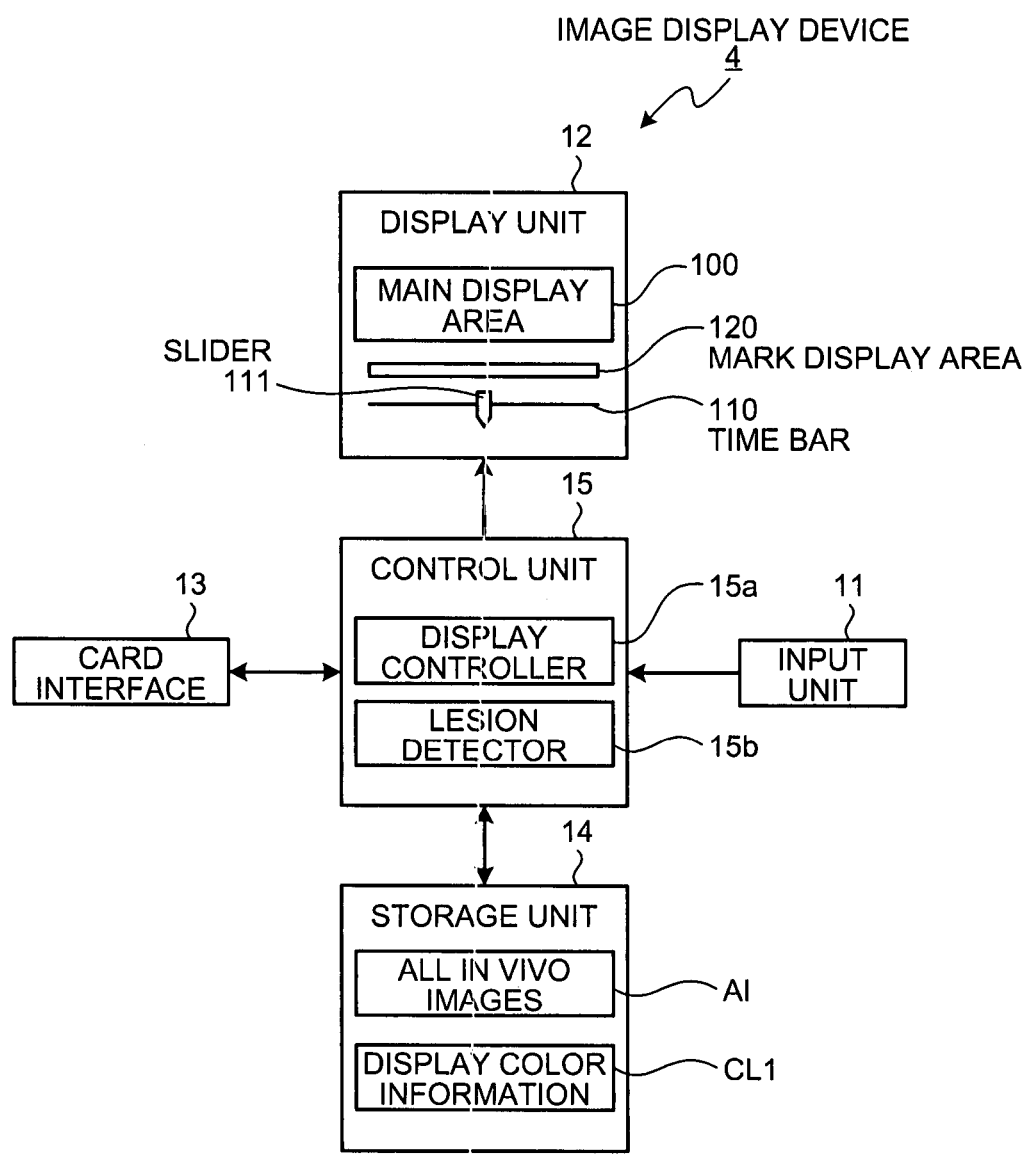
FIG. 2 is a block diagram schematically showing a configuration example of the image display device according to the first embodiment of the present invention.

Next, the configuration of the image display device 4 according to the first embodiment of the present invention will be described. FIG. 2 is a block diagram schematically showing a configuration example of the image display device 4 according to the first embodiment of the present invention. As shown in FIG. 2, the image display device 4 according to the first embodiment comprises an input unit 11 for inputting various kinds of information, a display unit 12 for displaying images inside the subject 1, GUI (Graphical User Interface) and the like in a screen, and a card interface (I/F) 13 for reading stored data (groups of images inside the subject 1 and the like) in the portable recording medium 5. The image display device 4 also comprises a storage unit 14 for storing various kinds of data concerning all in vivo images AI and a control unit 15 for controlling each component of the image display device 4.

The input unit 11 is realized using an input device such as a keyboard and mouse and inputs various kinds of information into the control unit 15 through an input operation by a user. For example, the input unit 11 inputs various kinds of instruction information giving instructions to the control unit 15 and patient information about the subject 1 into the control unit 15. Patient information input by the input unit 11 includes, for example, a patient name, sex, birth date, and patient ID of the subject 1.

The display unit 12 is realized using a display monitor that can display images such as a CRT display monitor and liquid crystal display monitor and displays various kinds of information instructed by the control unit 15 to display. More specifically, the display unit 12 displays various kinds of information used for observation and diagnosis of the subject 1 such as images picked up inside the subject 1 by the capsule endoscope 2. The display unit 12 also displays GUI relating to the display of each image contained in all in vivo images AI. The display unit 12 described above has a main display area 100 in which each image contained in all in vivo images AI. The display unit 12 also comprises a time bar 110 showing a temporal position (time position) of each image contained in all in vivo images AI and a slider 111 showing the time position of a current in vivo image currently displayed in the main display area 100. Further, the display unit 12 comprises a mark display area 120 in which a lesion mark is displayed at a time position of each of lesion images contained in all in vivo images AI.

The aforementioned portable recording medium 5 is detachably inserted into the card interface 13, which reads stored data in the portable recording medium 5 and transmits the obtained stored data to the control unit 15. The card interface 13 also writes information instructed by the control unit 15, for example, patient information of the subject 1, into the inserted portable recording medium 5.

The storage unit 14 is realized using a large-capacity recording medium such RAM, EEPROM, and hard disk and stores various kinds of data instructed by the control unit 15 to write and transmits stored data instructed by the control unit 15 to read to the control unit 15. The storage unit 14 described above stores all in vivo images AI, display color information CL1 for setting the display color of the lesion mark displayed by the mark display area 120 of the display unit 12 and the display color of the slider 111, and patient information of the subject 1. In this case, time information such as the imaging time or receiving time is associated with each image in all in vivo images AI stored in the storage unit 14.

The control unit 15 controls each component of the image display device 4. More specifically, the control unit 15 controls each of the input unit 11, display unit 12, card interface 13, and storage unit 14, and also controls input/output of information between such components. The control unit 15 described above acquires all in vivo images AI and time information associated with each image in all in vivo images AI from the portable recording medium 5 inserted in the card interface 13. The control unit 15 stores all in vivo images AI and time information after associating the time information with each image in the storage unit 14. Based on instruction information input by the input unit 11, the control unit 15 causes the display unit 12 to display in the main display area 100 each image contained in the group of images inside the subject 1.

The control unit 15 described above has a display controller 15a and a lesion detector 15b. The display controller 15a performs control to display each image contained in all in vivo images AI stored in the storage unit 14 in the main display area 100 of the display unit 12. If, in this case, any lesion image is contained in all in vivo images AI, the display controller 15a performs control to display such a lesion image inside the subject 1 in the main display area 100 of the display unit 12. The display controller 15a also causes the mark display area 120 of the display unit 12 to display a lesion mark indicating the time position of the lesion image in all in vivo images AI. In this case, the display controller 15a performs control to display the lesion mark in the lesion color set by the display color information CL1 stored in the storage unit 14.

Based on the display color information CL1 stored in the storage unit 14, the display controller 15a also controls the display color of the slider 111 in the display unit 12. More specifically, if the image currently displayed in the main display area 100 is a normal organ image of the subject 1 (that is, an image inside the subject 1 without lesion), the display controller 15a performs control to display the slider 111 indicating the time position of the currently displayed image in a default color. If, on the other hand, the image currently displayed in the main display area 100 is a lesion image of the subject 1, the display controller 15a performs control to change the display color of the slider 111 indicating the time position of the lesion image from the default color to lesion color.

The lesion image here means an image inside the subject 1 containing a lesion site such as bleeding as a photographic object. The default color of the aforementioned slider 111 is a color (such as gray) initially set as the display color of the slider 111, and the lesion color of the aforementioned slider 111 and lesion mark is a color corresponding to a lesion indicated by a lesion image inside the subject 1 and is different from the default color. If, for example, the lesion image is an image of a bleeding site (hereinafter referred to as a bleeding image), red is set as the lesion color corresponding to the bleeding site, which is a kind of lesion. The default color and the lesion color described above are set by the display color information CL1 stored in the storage unit 14.

The lesion detector 15b detects lesion images contained in all in vivo images AI. More specifically, the lesion detector 15b detects color information of an image to be processed contained in all in vivo images AI and, based on color information of the detected image, determines whether the image to be processed is a lesion image. Color information of images detected by the lesion detector 15b includes, for example, an average color of an image, and values of color elements of red (R), green (G), and blue (B) of an image. If the lesion detector 15b determines that an image to be processed is a lesion image, the lesion detector 15b detects the lesion image from all in vivo images AI. The lesion detector 15b performs detection processing of such a lesion image for all images in all in vivo images AI to detect lesion images contained in all in vivo images AI. If the lesion detector 15b detects any lesion image in all in vivo images AI, the lesion detector 15b attaches a sign (lesion flag) indicating a lesion image to the detected lesion image. Lesion images to which the lesion flag is attached are stored in the storage unit 14 as a portion of all in vivo images AI.

Figure 3:
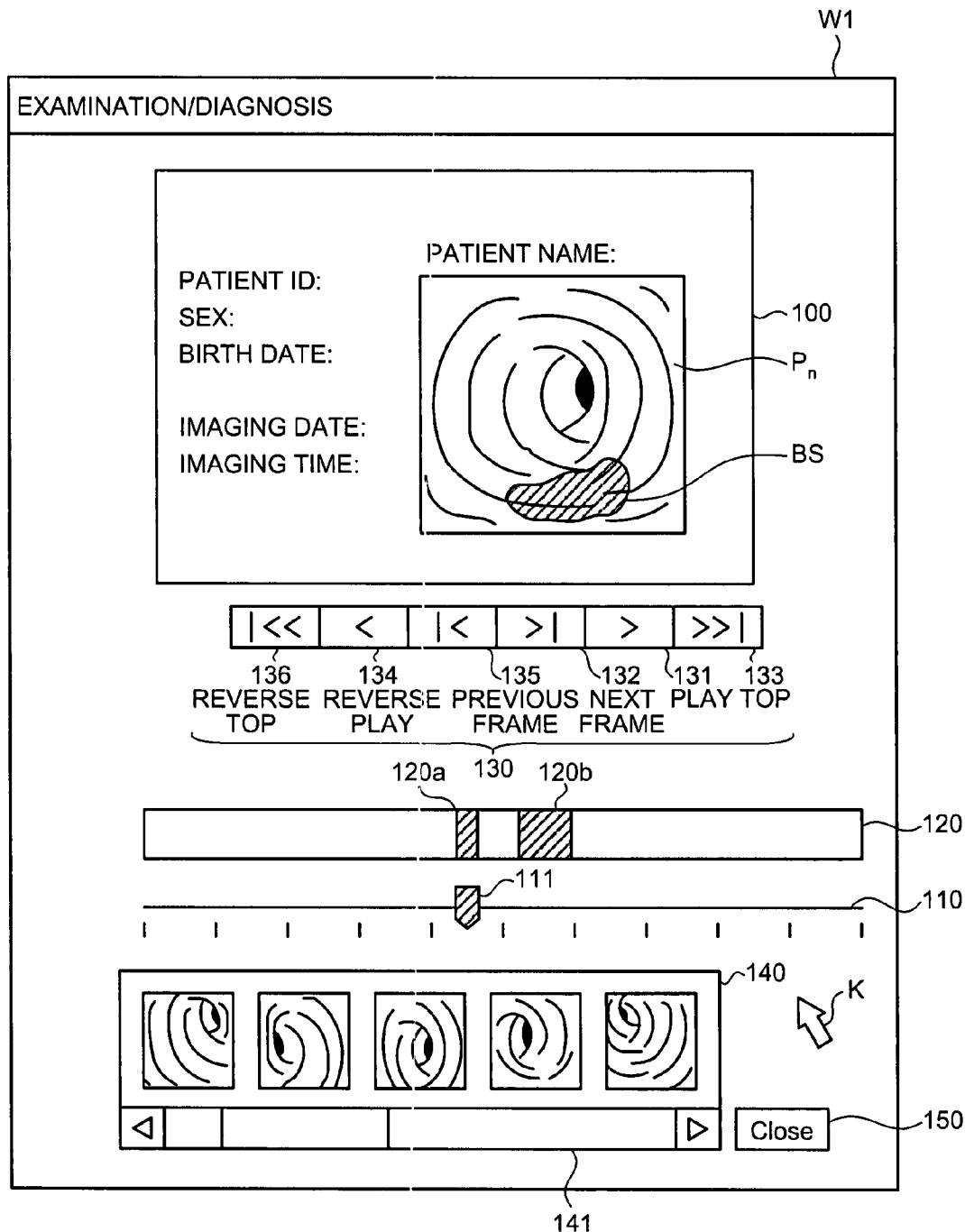
FIG. 3 is a schematic view showing a concrete example of a display mode of a display unit.

Next, the display mode of the display unit 12 will be concretely exemplified to describe an operation of the display controller 15a to control GUI displayed in the display unit 12 and a display operation of the display unit 12. FIG. 3 is a schematic view showing a concrete example of the display mode of the display unit 12. If predetermined login processing is performed by the control unit 15, the display controller 15a causes the display unit 12 to display a window W1 like one shown in FIG. 3.

As shown in FIG. 3, the aforementioned main display area 100, time bar 110, slider 111, and mark display area 120 are formed in the window W1. Also in the window W1, a display operation icon group 130 for performing various kinds of display operations when displaying an image inside the subject 1 in the main display area 100, a display sub-area 140 for displaying reduced images of desired images selected from the group of images inside the subject 1 displayed in the main display area 100, and a scroll operation unit 141 for performing a scroll operation of a plurality of reduced images displayed in the display sub-area 140 are formed. In addition, a cursor K for performing a click or drag operation of various GUIs by an operation of the input unit 11 and a Close icon 150 for closing the window W1 are formed in the window W1.

The main display area 100 is an image display area for displaying each image contained in all in vivo images AI to be processed for display. Based on instruction information input by the input unit 11, the display controller 15a performs control to display each image in all in vivo images AI in the main display area 100. The main display area 100 displays an image $P_n$ (frame number n=1, 2, 3, ... ) in all in vivo images AI through control of the display controller 15a. The display controller 15a also performs control to display in the main display area 100 the imaging date and imaging time of the image (for example, the image $P_n$) currently displayed in the main display area 100 and patient information (patient name, patient ID, sex, and birth date) of the subject 1.

The time bar 110 and slider 111 are GUIs for indicating the time position of the image currently displayed in the main display area 100. More specifically, the time bar 110 is an elongated image component on which all in vivo images AI are mapped in a time series order with both ends thereof set for the first and the second picked-up in vivo images. Thus, the time bar 110 serves as a time scale covering from the pick up time of the first image to the pick up time of the last image. Each of all in vivo images AI can be expressed as a position on the time bar 110 which position corresponds to the position, in time series, of the in vivo image in all in vivo images AI. In this document, such the position on the time bar 110 of each in vivo image is referred to as "the time position" on the time bar 110. The slider 111 indicates the time position of the image currently displayed in the main display area 100 on the time bar 110. The slider 111 moves along the time bar 110 to indicate the time position on the time bar 110 corresponding to the image currently displayed in the main display area 100. Movement of the slider 111 is controlled by the display controller 15a. That is, the display controller 15a controls movement of the slider 111 on the time bar 110 and display switching of the image currently displayed in the main display area 100 (image inside the subject 1) so that the slider 111 always indicates the time position of the image currently displayed in the main display area 100.

As described above, the mark display area 120 is a horizontally long display area in which a lesion mark for each of lesion images contained in all in vivo image AI is displayed at a position (or time position) along the time scale which position corresponds to the time position of the lesion image in all in vivo images AI. More specifically, the mark display area 120 is formed like a bar along the aforementioned time bar 110. The display controller 15a displays a lesion mark for each of lesion images contained in all in vivo images AI in a predetermined lesion color. In case of an example shown in FIG. 3, two lesion mark groups are shown in the mark display area 120, which means that there are two lesion sites in the subject 1. In this case, the display controller 15a displays a lesion mark for each of lesion images picked up for each of the two lesion sites inside the subject in a predetermined lesion color, e.g., in red. In this case, each lesion mark is displayed at a position along the time scale of the mark display area 120 which position corresponds to a time position of the corresponding lesion image in all in vivo image AI.

Here, if the image currently displayed in the main display area 100 (the image $P_n$ inside the subject 1) is a bleeding image containing a bleeding site BL as a photographic object, the slider 111 moves to a position of the lesion mark 120a indicating the time position of the bleeding image and the display color thereof changes from the default color to the lesion color. In this case, both the lesion mark 120a indicating the time position of the bleeding image and the slider 111 are in the lesion color (for example, red) corresponding to the bleeding site and thus are displayed in the same color. The slider 111 that changes its display color (an example of the display mode), as described above, indicates the time position of each image containing a lesion image in all in vivo images AI along the time bar 110 and also functions as a time position display means having the display color (the default color or lesion color) indicating whether the image currently displayed in the main display area 100 is a lesion image. Meanwhile, information indicated by the display color of the slider 111 (that is, information indicating whether the image currently displayed in the main display area 100 is a lesion image) is information about the display of a lesion image displayed in the main display area 100.

The display operation icon group 130 is GUI for performing display operations when displaying in the main display area 100 each image contained in all in vivo images AI. The display operation icon group 130 includes, for example, a play icon 131, next frame icon 132, top search icon 133, reverse play icon 134, previous frame icon 135, and reverse top search icon 136. The input unit 11 inputs display instruction information corresponding to a desired icon into the control unit 15 by performing a click operation of the desired icon from the display operation icon group 130. Based on the display instruction information input by the input unit 11, the display controller 15a performs control to display the image $P_n$ in all in vivo images AI in the main display area 100.

More specifically, when a click operation of the play icon 131 is performed, the image $P_n$ in all in vivo images AI is made to be successively displayed in the main display area 100 by the display controller 15a in a forward direction of the time series and, when a click operation of the next frame icon 132 is performed, one frame of the image $P_n$ in all in vivo images AI is made to be displayed in the main display area 100 in the forward direction of the time series each time the click operation is performed. When a click operation of the reverse play icon 134 is performed, the image $P_n$ in all in vivo images AI is made to be successively displayed in the main display area 100 by the display controller 15a in a backward direction of the time series and, when a click operation of the previous frame icon 135 is performed, one frame of the image $P_n$ in all in vivo images AI is made to be displayed in the main display area 100 in the backward direction of the time series each time the click operation is performed.

When, a click operation of the top search icon 133 is performed, on the other hand, the end image in all in vivo images AI is made to be displayed in the main display area 100 by the display controller 15a. When a click operation of the reverse top search icon 136 is performed, the first image in all in vivo images AI is made to be displayed in the main display area 100 by the display controller 15a.

Figure 4:
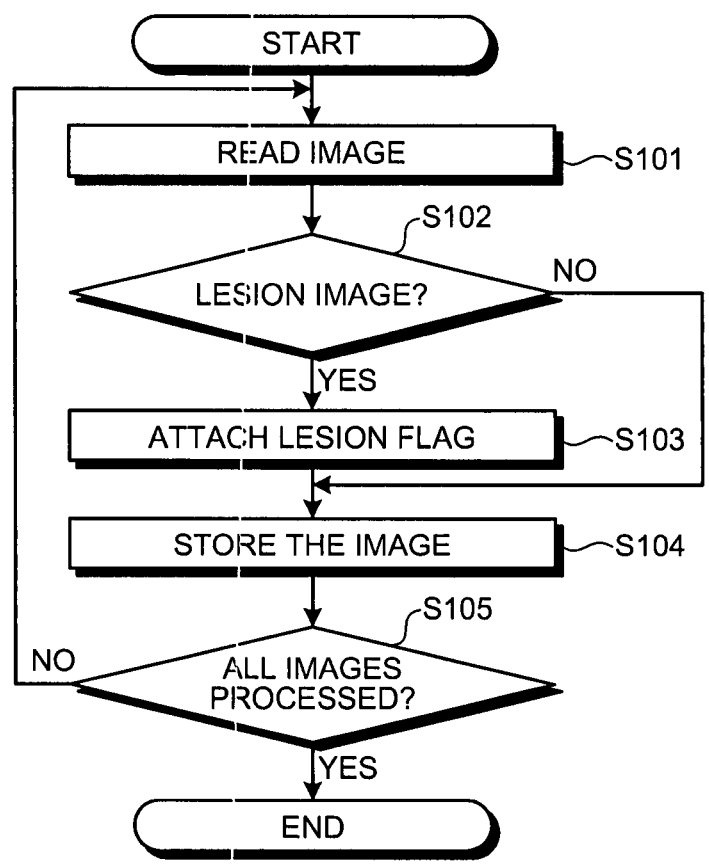
FIG. 4 is a flow chart exemplifying a processing procedure of a control unit for detecting a lesion image contained in an image group inside a subject.

Next, an operation of the control unit 15 to detect any lesion image contained in all in vivo images AI will be described. FIG. 4 is a flow chart exemplifying a processing procedure of the control unit 15 for detecting a lesion image contained in all in vivo images AI. The control unit 15 captures all in vivo images AI from the portable recording medium 5 inserted in the card interface 13 and also detects color information of each image in all in vivo images AI. If, based on the detected color information, a lesion image (for example, a bleeding image) is detected, the control unit 15 attaches a lesion flag to the lesion image. In this case, the control unit 15 stores all in vivo images AI containing the lesion image with the attached lesion flag in the storage unit 14.

More specifically, as shown in FIG. 4, the control unit 15 reads an image to be processed from among all in vivo images AI stored in the portable recording medium 5 inserted in the card interface 13 (step S101). In this case, the control unit 15 successively reads the image $P_n$ (frame number n=1, 2, 3, . . . ) from all in vivo images AI, for example, in a time series.

Next, the control unit 15 determines whether the image inside the subject 1 read as an image to be processed is a lesion image (step S102). In this case, the lesion detector 15b detects color information of the image inside the subject 1 to be processed and, based on the detected color information, determines whether the image is a lesion image. More specifically, if the lesion detector 15b detects an average color of the image as the color information and the detected average color of the image closely resembles that of a lesion image, the lesion detector 15b determines that the image to be processed is a lesion image inside the subject 1. Also, if the lesion detector 15b detects values of RGB color elements forming the image as the color information and each detected color element value of RGB is within a range of each color element value of a lesion image, the lesion detector 15b determines that the image to be processed is a lesion image inside the subject 1. In this manner, the lesion detector 15b detects lesion images (for example, bleeding images) contained in all in vivo images AI.

When the image to be processed is determined to be a lesion image (step 102, Yes), the control unit 15 attaches a lesion flag to the lesion image inside the subject 1 (step S103). In this case, if, for example, the detected lesion image is a bleeding image, the lesion detector 15b attaches a lesion flag indicating a bleeding image to the lesion image inside the subject 1.

Next, the control unit 15 stores the lesion image inside the subject 1 with the attached lesion flag in the storage unit 14 (step S104). In this case, the lesion image inside the subject 1 with the attached lesion flag is stored in the storage unit 14 as part of all in vivo images AI.

Subsequently, the control unit 15 determines whether processing of all images contained in all in vivo images AI has been performed (step S105). More specifically, if any image inside the subject 1 that has not been read remains in the portable recording medium 5 inserted in the card interface 13 or any image inside the subject 1 that has not been stored in the storage unit 14 remains in the portable recording medium 5, the control unit 15 determines that processing of all in vivo images AI has not been completed (step S105, No) and returns to the aforementioned step S101 to repeat the processing procedure of step S101 and thereafter.

The control unit 15 performs the processing procedure of the aforementioned steps S101 to S105 for each image contained in all in vivo images AI repeatedly and stores all in vivo images AI containing any lesion image with the attached lesion flag in the storage unit 14.

If, on the other hand, all images in all in vivo images AI have been read from the portable recording medium 5 inserted in the card interface 13 or all images in all in vivo images AI stored in the portable recording medium 5 have been stored in the storage unit 14, the control unit 15 determines that processing of all images in all in vivo images AI has been completed (step S105, Yes) and terminates detection processing of lesion images in all in vivo images AI.

Meanwhile, if the control unit 15 determines that an image to be processed is not a lesion image in the aforementioned step S102 (step S102, No), the control unit 15 proceeds to the aforementioned step S104 to repeat the processing procedure of step S104 and thereafter. In this case, the lesion detector 15b does not attach any lesion flag to the image inside the subject 1 that is not a lesion image (that is, a normal organ image). That is, the image inside the subject 1 that is not a lesion image is stored in the storage unit 14 as part of all in vivo images AI without a lesion flag being attached.

Figure 5:
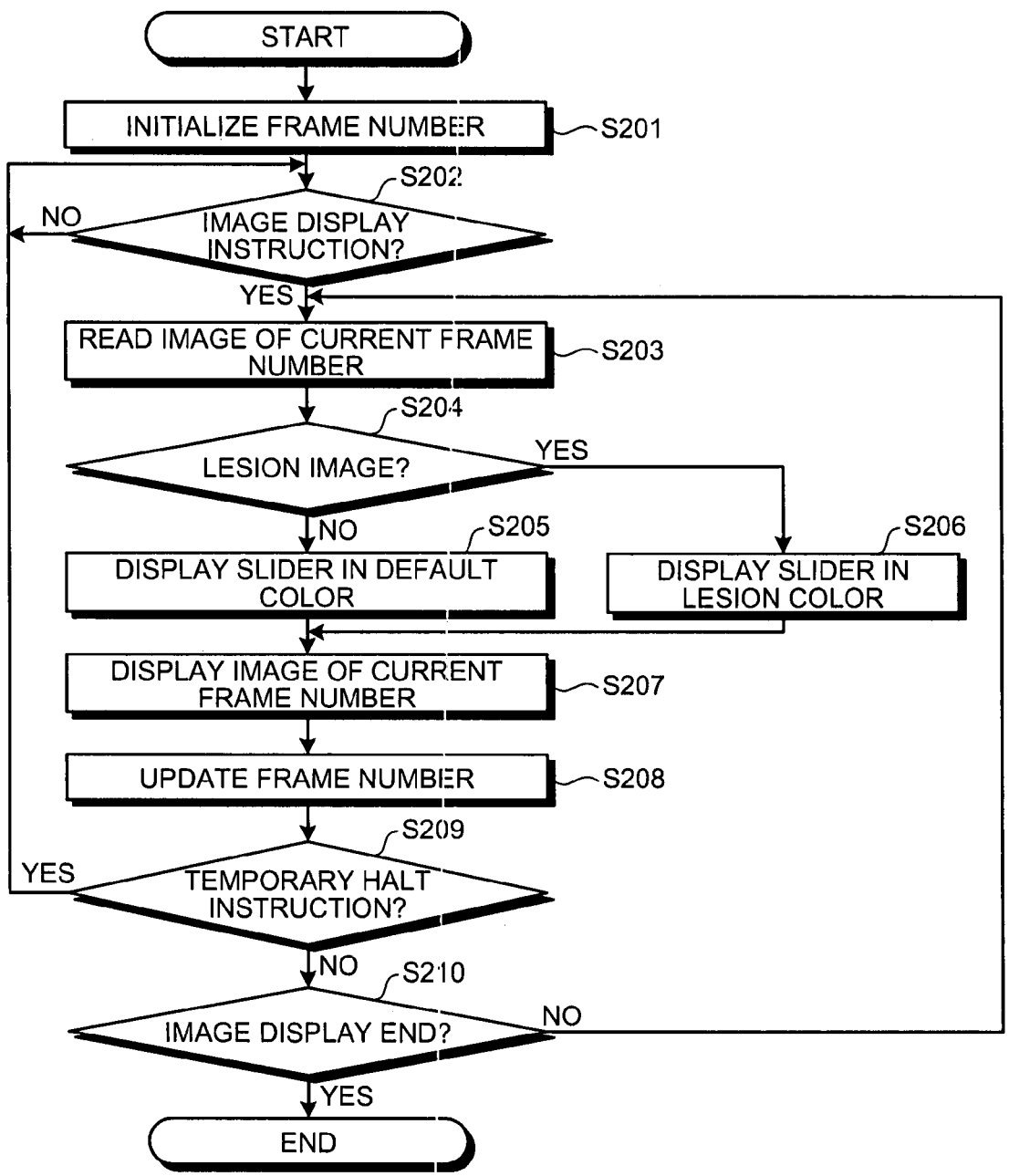
FIG. 5 is a flow chart illustrating the processing procedure of the control unit of the image display device according to the first embodiment.

Next, operations of the control unit 15 to perform control to display in the main display area 100 each image contained in all in vivo images AI and to control the display color of the slider 111 indicating the time position of the image currently displayed in the main display area 100 will be described. FIG. 5 is a flow chart illustrating the processing procedure of the control unit 15 of the image display device 4 according to the first embodiment.

As shown in FIG. 5, while the display unit 12 is caused to display the aforementioned window W1 (See FIG. 3), the control unit 15 initializes the frame number n of all in vivo images AI to be displayed in the main display area 100 of the window W (step S201). In this case, the control unit 15 initializes the frame number n (for example, n=1) to identify the image to be subject to display processing for displaying in the main display area 100 from among images contained in all in vivo images AI.

Next, the control unit 15 determines whether there is any image display instruction for the main display area 100 (step S202). More specifically, the input unit 11 inputs display instruction information corresponding to any of icons contained in the aforementioned display operation icon group 130 (for example, the play icon 131, next frame icon 132, reverse play icon 134, or previous frame icon 135) into the control unit 15. If no such display instruction information is input by the input unit 11, the display controller 15a determines that there is no image display instruction for the main display area 100 (step S202, No) and repeats this step S202. That is, the display controller 15a repeats this step S202 until such display instruction information is input by the input unit 11.

If such display instruction information is input by the input unit 11, on the other hand, the control unit 15 determines that there are image display instructions for the main display area 100 (step S202, Yes) and reads the image of the current frame number, which is an image inside the subject 1 to be processed for display (step S203). In this case, the control unit 15 reads the image of the current frame number from all in vivo images AI stored in the storage unit 14.

Next, the control unit 15 determines whether the read image of the current frame number (that is, the image inside the subject 1 to be processed for display) is a lesion image (step S204). In this case, the control unit 15 determines whether a lesion flag is attached to the image of the current frame number and, if no lesion flag is attached, determines that the image of the current frame number is not a lesion image.

If the image of the current frame number is determined not to be a lesion image (step S204, No), the control unit 15 performs control to display the slider 111 indicating the time position of the image of the current frame number, that is, an image containing no lesion site as a photographic object (normal organ image) in the default color (step S205). In this case, the display controller 15a causes the slider 111 to move to the time position on the time bar 110 corresponding to the image of the current frame number, which is a normal organ image, and performs control to display the slider 111 indicating the time position of the image of the current frame number, which is the aforementioned normal organ image, in the default color.

If, in step S204, a lesion flag is attached to the image of the current frame number, on the other hand, the display controller 15a determines that the image of the current frame number is a lesion image. If the image of the current frame number is determined to be a lesion image (step S204, Yes), the control unit 15 performs control to display the slider 111 indicating the time position of the image of the current frame number, that is, the lesion image in the lesion color (step S206). In this case, the display controller 15a causes the slider 111 to move to the time position on the time bar 110 corresponding to the image of the current frame number, which is a lesion image, and performs control to display the slider 111 indicating the time position of the image of the current frame number, which is the aforementioned lesion image, in the lesion color.

Subsequently, the control unit 15 performs control to display the image of the current frame number in the main display area 100 (step S207). Meanwhile, the frame number of the image displayed in the main display area 100 (that is, the current frame number) in step S207 is the frame number initialized in the aforementioned step S201 or the frame number updated in step S208 described later.

If, in step S207, the image of the current frame number is not a lesion image (that is, a normal organ image), the normal organ image of the current frame number is made to be displayed in the main display area 100 by the display controller 15a. In this case, the normal organ image inside the subject 1 is displayed in the main display area 100 and also the slider 111 indicating the time position of the normal organ image inside the subject 1 currently displayed in the main display area 100 is displayed in the default color.

If, on the other hand, the image of the current frame number is a lesion image, the lesion image of the current frame number is made to be displayed in the main display area 100 by the display controller 15a. In this case, the lesion image inside the subject 1 is displayed in the main display area 100 and also the slider 111 indicating the time position of the lesion image inside the subject 1 currently displayed in the main display area 100 is displayed in the lesion color. Here, the lesion color of the slider 111 is a color corresponding to the lesion indicated by the lesion image, which is the image currently displayed in the main display area 100, and is the same as the lesion color of the lesion mark (for example, the lesion mark 120a) in the mark display area 120 indicating the time position of the lesion image.

Next, the control unit 15 updates the frame number of all in vivo images AI to be processed for display (step S208). In this case, for example, by adding +1 to the frame number n of the image inside the subject 1 currently displayed in the main display area 100, the display controller 15a updates the frame number n of all in vivo images AI to be processed for display.

Subsequently, the control unit 15 determines whether there is any temporary halt instruction of the image inside the subject 1 currently displayed in the main display area 100 (step S209). More specifically, if display instruction information corresponding to the aforementioned next frame icon 132 or previous frame icon 135 is input by the input unit 11, the control unit 15 determines that there is a temporary halt instruction (step S209, Yes). In this case, the control unit 15 returns to the aforementioned step S202 to repeat step S202 and thereafter.

If, on the other hand, no display instruction information corresponding to the next frame icon 132 or previous frame icon 135 is input, the control unit 15 determines that there is no temporary halt instruction (step S209, No) and determines whether image display processing to display in the main display area 100 an image contained in all in vivo images AI has terminated (step S210).

More specifically, if the frame number n updated in the aforementioned step S208 exceeds the number of frames of all in vivo images AI to be processed for display, the control unit 15 determines that image display processing of all in vivo images AI has terminated (step S210, Yes) and terminates the image display processing of all in vivo images AI. If, on the other hand, the frame number n updated in the aforementioned step S208 is equal to or less than the number of frames of all in vivo images AI to be processed for display, the control unit 15 determines that image display processing of all in vivo images AI has not terminated (step S210, No) and returns to the aforementioned step S203 to repeat step S203 and thereafter.

Figure 6:
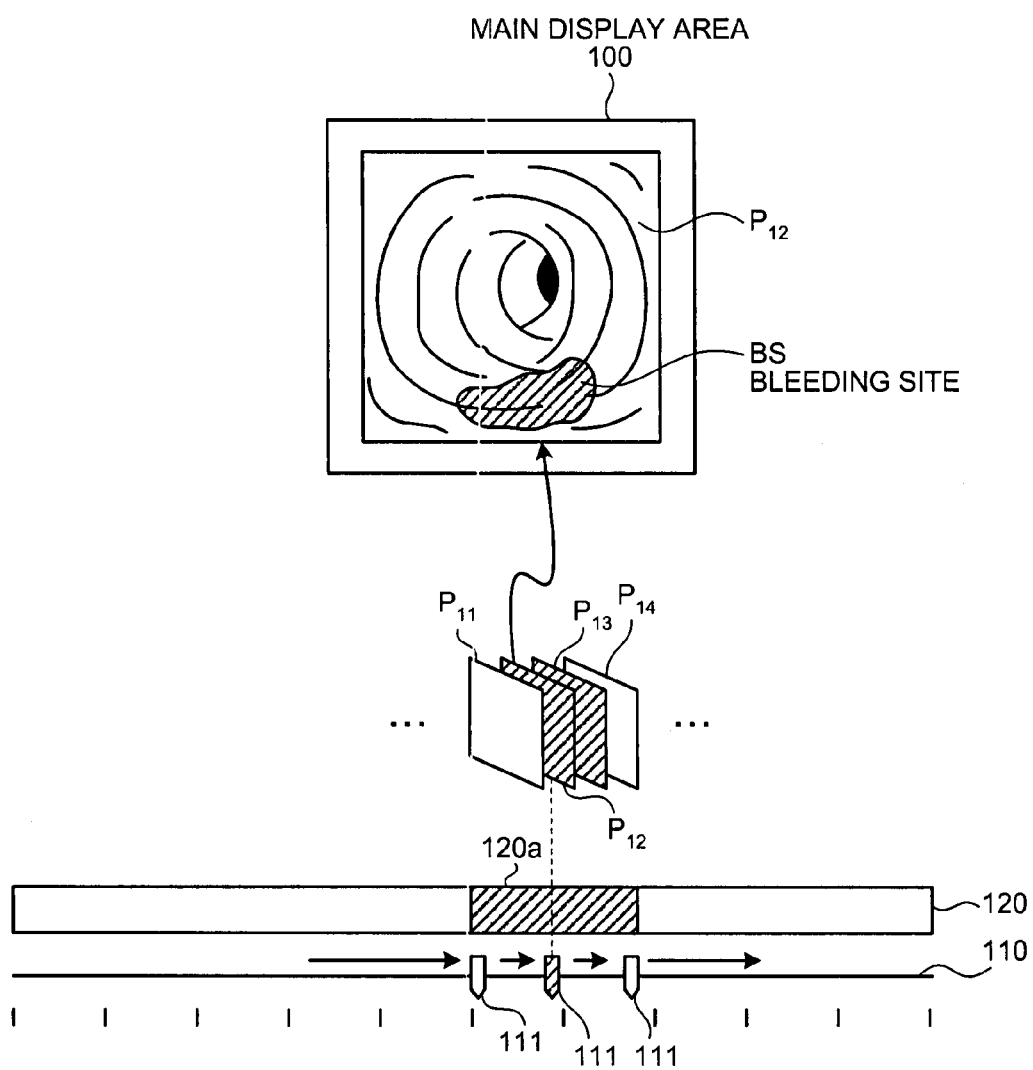
FIG. 6 is a schematic view illustrating an operation of the control unit changing a display color of a slider to a lesion color corresponding to a bleeding site.

Next, a case in which a lesion image containing a bleeding site, which is an example of lesion, as a photographic object (that is, a bleeding image) is displayed in the main display area 100 will be exemplified to concretely describe an operation of the control unit 15 that performs control to change the display color of the slider 111 indicating the time position of the bleeding image from the default color to the lesion color. FIG. 6 is a schematic view illustrating an operation of the control unit 15 for changing the display color of the slider 111 indicating the time position of the currently displayed bleeding image to a lesion color corresponding to a bleeding site.

Before making each image contained in all in vivo images AI to be displayed in the main display area 100, the control unit 15 causes the mark display area 120 to display a lesion mark indicating the time position of a bleeding image contained in all in vivo images AI. More specifically, if, for example, bleeding images $P_{12}$ and $P_{13}$ contained in all in vivo images AI are detected, the control unit 15 causes the mark display area 120 to display the lesion mark 120a indicating the time positions of the bleeding images $P_{12}$ and $P_{13}$. In this case, the display controller 15a performs control to display the lesion mark 120a in the lesion color (for example, red) corresponding to the bleeding site shown in the bleeding images $P_{12}$ and $P_{13}$.

The lesion mark 120a is displayed, as shown in FIG. 6, for example, in a bar form at the time position in the mark display area 120 corresponding to the bleeding images $P_{12}$ and $P_{13}$. The lesion mark 120a displayed in a bar form represents a partial image group containing the $P_{12}$ and $P_{13}$ among all in vivo images AI. Such a partial image group contains, for example, the bleeding images $P_{12}$ and $P_{13}$ and images $P_{11}$ and $P_{14}$. The images $P_{11}$ and $P_{14}$ inside the subject 1 are images near the frame numbers of the bleeding images $P_{12}$ and $P_{13}$ and in which normal organ interiors are picked up.

Subsequently, based on display instruction information input by the input unit 11, the control unit 15 performs control to display in the main display area 100 the image $P_n$ (n=1, 2, 3, . . . ) contained in the group of images inside the subject 1 and also causes the slider 111 to move along the time bar 110 to indicate the time position of the image currently displayed in the main display area 100. In this case, if the image currently displayed in the main display area 100 is not a lesion image, the control unit 15 performs control to display the slider 111 indicating the time position of the currently displayed image in the default color and, if the image currently displayed in the main display area 100 is a lesion image, the control unit 15 performs control to display the slider 111 indicating the time position of the lesion image in the lesion color.

More specifically, as shown in FIG. 6, if the image currently displayed in the main display area 100 is the image $P_{11}$ or $P_{14}$, the control unit 15 performs control to display the slider 111 in the default color even if the slider 111 is positioned within the display range of the lesion mark 120a. If, on the other hand, the image currently displayed in the main display area 100 is the bleeding image $P_{12}$ or $P_{13}$, the control unit 15 performs control to change the default color of the slider 111 positioned within the display range of the lesion mark 120a to the lesion color corresponding to the bleeding site. In this case, the control unit 15 changes the lesion color of the slider 111 indicating the time position of the bleeding image $P_{12}$ or $P_{13}$ to that (for example, red) of the lesion mark 120a.

Through control of the display color of the slider 111 by the control unit 15, as described above, the slider 111 can not only indicate the time position of the currently displayed image in all in vivo images AI, but also display whether the currently displayed image is a lesion image such as a bleeding image by its display color (the default color or lesion color). The slider 111 described above is displayed apart from the image currently displayed in the main display area 100. Thus, the slider 111 does not disturb observation of the image currently displayed in the main display area 100 even if its display color changes to the lesion color or default color.

Therefore, a user such as a physician and nurse can observe the image currently displayed in the main display area 100 without being disturbed by change in display color of the slider 111 and also understand easily that the currently displayed image is a lesion image by visually confirming the lesion color of the slider 111. As a result, while the slider 111 is positioned within the display range of the lesion mark displayed by the mark display area 120, the user can easily identify lesion images such as bleeding images from among a partial image group inside the subject 1 successively displayed in the main display area 100.

More specifically, while the slider 111 is positioned within the display range of the lesion mark 120a displayed in a bar form, the user can easily identify the bleeding images $P_{12}$ and $P_{13}$ from among the partial image group (each image whose frame number is n=11 to 14) inside the subject 1 successively displayed in the main display area 100. Accordingly, the bleeding images $P_{12}$ and $P_{13}$ can easily be displayed in the main display area 100 and also the bleeding site BL inside the subject 1 contained as a photographic object of the bleeding images $P_{12}$ and $P_{13}$ can easily be observed.

As has been described, in the first embodiment of the present invention, the image display device is configured in such ways that each image contained in a group of images inside a subject is displayed in a main display area, a time position of an image currently displayed in the main display area is indicated by a slider moving on a time bar indicating the time position of each image in the group of images and, if the image currently displayed in the main display area is a lesion image, the default color of the slider is changed to a lesion color. Thus, by visually confirming the display color (the lesion color or default color) of the slider, whether the currently displayed image in the main display area is a lesion image can easily be determined. As a result, an image display device that enables easy identification of lesion images of bleeding sites and the like inside the subject from among a group of images successively displayed in the main display area without disturbing observation of images inside the subject displayed in the main display area can be realized.

By using an image display device according to the first embodiment of the present invention, lesion images such as bleeding images can easily be detected from a group of images inside a subject so that such lesion images inside the subject can easily be observed.

Second Embodiment

Next, a second embodiment of the present invention will be described. In the first embodiment described above, one kind of lesion images (for example, bleeding images) contained in all in vivo images AI is detected, but in the second embodiment, multiple kinds of lesion images contained in all in vivo images AI are detected and a different lesion color of the slider 111 is used for each lesion indicated by multiple kinds of lesion images. Bleeding images in which a bleeding site inside the subject 1 is picked up and fading images in which a fading site inside the subject 1 is picked up are exemplified below as multiple kinds of lesion images contained in all in vivo images AI.

Figure 7:
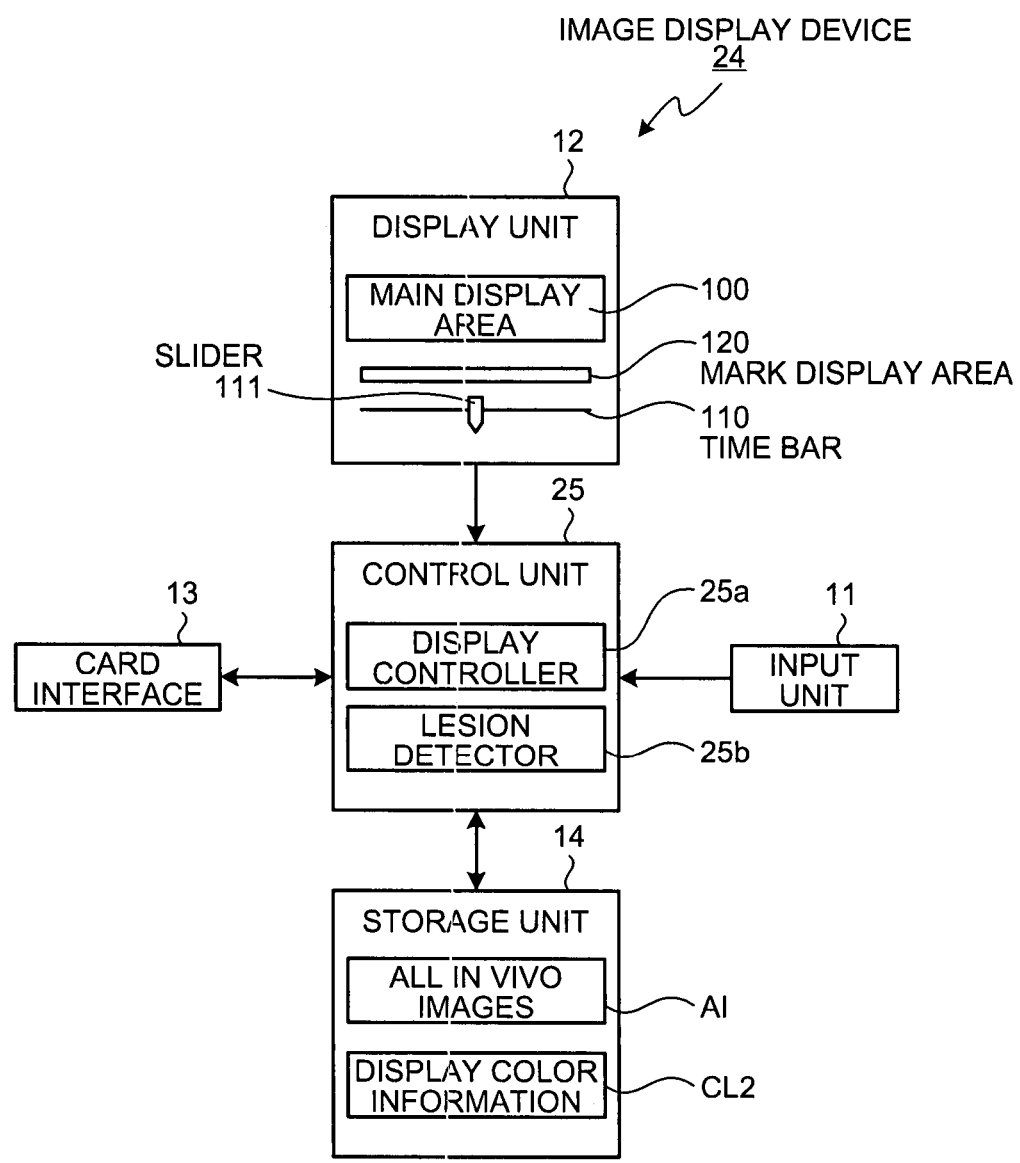
FIG. 7 is a block diagram schematically showing a configuration example of an image display device according to a second embodiment of the present invention.

FIG. 7 is a block diagram schematically showing a configuration example of an image display device according to the second embodiment of the present invention. As shown in FIG. 7, an image display device 24 according to the second embodiment has a control unit 25, instead of the control unit 15 of the image display device 4 according to the aforementioned first embodiment. In the image display device 24, the mark display area 120 in the display unit 12 displays a plurality of lesion marks each indicating each time position of multiple kinds of lesion images. The storage unit 14 stores display color information CL2 instead of the aforementioned display color information CL1. An in-vivo information acquiring system according to the second embodiment of the present invention has the image display device 24 instead of the image display device 4 in the in-vivo information acquiring system according to the aforementioned first embodiment (See FIG. 1). Other components are the same as those of the first embodiment and the same numeral is attached to the same component.

The storage unit 14 stores, as described above, the display color information CL2 instead of the display color information CL1. The display color information CL2 is used to set a plurality of lesion colors corresponding to a plurality of lesions and the aforementioned default color. A plurality of lesion colors set by the display color information CL2 include, for example, a lesion color corresponding to a bleeding site (hereinafter referred to as a bleeding lesion color) and that corresponding to a fading site (hereinafter referred to as a fading lesion color). Display colors (the default color and a plurality of lesion colors) set by the display color information CL2 are used as display colors of lesion marks in the aforementioned mark display area 120 and as display colors of the slider 111.

Approximately similarly to the control unit 15 of the image display device 4 according to the aforementioned first embodiment, the control unit 25 controls each of the input unit 11, display unit 12, card interface 13, and storage unit 14, and also controls input/output of information between such components. Also, the control unit 25 acquires all in vivo images AI from the portable recording medium 5 inserted in the card interface 13 to detect multiple kinds of lesions (for example, bleeding images and fading images) contained in all in vivo images AI. In this case, the control unit 25 performs control to display in the main display area 100 each image in all in vivo images AI containing multiple kinds of lesion images and controls the lesion color of the slider 111 and that of the lesion mark to have a different color for each kind of lesion images (that is, for each kind of lesion indicated by lesion images). The control unit 25 described above has a display controller 25a instead of the display controller 15a of the control unit 15 in the aforementioned first embodiment and a lesion detector 25b instead of the lesion detector 15b.

The display controller 25a has a function approximately similar to that of the aforementioned display controller 15a of the control unit 15. More specifically, the display controller 25a performs control to display in the main display area 100 each image in all in vivo images AI containing, for example, bleeding images and fading images and, at the same time, causes the slider 111 to move along the time bar 110 so that the slider 111 indicates the time position of the image currently displayed in the main display area 100. If the image currently displayed in the main display area 100 is an image other than a lesion image (that is, a normal organ image), the display controller 25a performs control to display the slider 111 indicating the time position of the currently displayed image in the default color. If, on the other hand, the image currently displayed in the main display area 100 is a bleeding image, the display controller 25a performs control to change the display color of the slider 111 indicating the time position of the bleeding image to the lesion color of bleeding and, if the image currently displayed in the main display area 100 is a fading image, the display controller 25a performs control to change the display color of the slider 111 indicating the time position of the fading image to the lesion color of fading.

The display controller 25a also causes the mark display area 120 to display a plurality of lesion marks indicating each time position of multiple kinds of lesion images (for example, bleeding images and fading images) contained in all in vivo images AI. More specifically, the display controller 25a performs control to display the lesion marks indicating the time positions of bleeding images inside the subject 1 in the lesion color of bleeding and the lesion marks indicating the time positions of fading images inside the subject 1 in the lesion color of fading. In this case, the lesion marks for such bleeding images are displayed in the lesion color of bleeding (for example, red) at the time position in the mark display area 120 corresponding to the bleeding images inside the subject 1. The lesion marks for such fading images are displayed in the lesion color of fading (for example, white) at the time position in the mark display area 120 corresponding to the fading images inside the subject 1.

Meanwhile, the aforementioned default color, lesion color of bleeding, and lesion color of fading are set by the display color information CL2 stored in the storage unit 14. In this case, the default color, lesion color of bleeding, and lesion color of fading are set to different colors, for example, gray, red, and white respectively.

Approximately similarly to the aforementioned lesion detector 15b of the control unit 15, the lesion detector 25b detects color information of an image contained in all in vivo images AI and, based on the detected color information, determines whether the image to be processed is a lesion image. In this case, the lesion detector 25b detects multiple kinds of lesion images contained in all in vivo images AI. Multiple kinds of lesion images detected by the lesion detector 25b include, for example, bleeding images and fading images inside the subject 1. The lesion detector 25b attaches a lesion flag that is different for each lesion to the bleeding images and fading images. The bleeding images and fading images to which a lesion flag that is different for each lesion is attached are stored in the storage unit 14 as a part of all in viva images AI.

Figure 8:
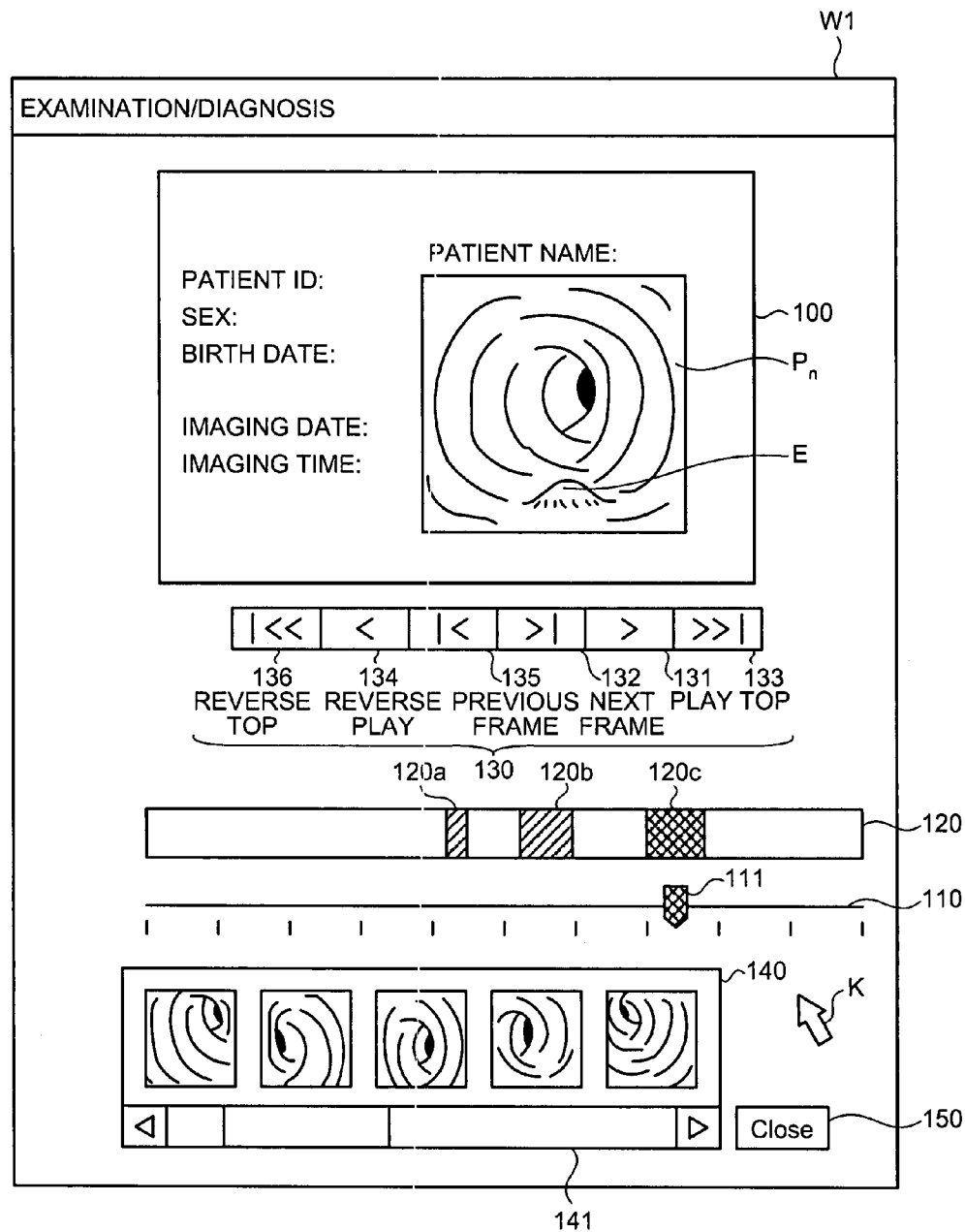
FIG. 8 is a schematic view showing an exemplary screen image of the control unit in which a plurality of lesion marks are displayed in respective lesion colors different by kinds of lesions.

Next, the display mode of the display unit 12 will be concretely exemplified to describe an operation of the display controller 25a to control GUI displayed in the display unit 12 and a display operation of the display unit 12. FIG. 8 is a schematic view exemplifying the display mode of the control unit 12 displaying a plurality of lesion marks in lesion colors that are different for each lesion. As is shown in FIG. 8, in the window W1 displayed in the display unit 12 of the image display device 24, multiple kinds of lesion marks, for example, the lesion marks 120a and 120b indicating each time position of a plurality of bleeding images and a lesion mark 120c indicating the time position of a fading image are displayed by the mark display area 120. Multiple kinds of lesion images inside the subject 1 are displayed in the main display area 100 and include, for example, bleeding images containing the bleeding site BL inside the subject 1 as a photographic object and a fading image containing a fading site E inside the subject 1 as a photographic object. Other display modes of the window W1 are the same as those of the aforementioned first embodiment.

As shown in FIG. 8, the mark display area 120 displays the lesion marks 120a, 120b, and 120c in the lesion color that is different for each lesion. In this case, the display controller 25a performs control to display the lesion marks 120a and 120b in the lesion color of bleeding (for example, red) at each time position in the mark display area 120 corresponding to each of a plurality of bleeding images contained in all in vivo images AI. The display controller 25a also performs control to display the lesion mark 120c in the lesion color of fading (for example, white) at the time position in the mark display area 120 corresponding to the fading image contained in all in vivo images AI. The mark display area 120 that displays a plurality of lesion marks in the lesion color different for each lesion (an example of the display mode), as described above, shows the time positions of a plurality of lesion images in all in vivo images AI along the time bar 110 and also functions as a time position display means having a display mode indicating the kind of lesion indicated by the lesion image displayed in the main display area 100. Information indicated by the lesion color of each lesion mark displayed by the mark display area 120 (that is, information indicating the kind of lesion indicated by each lesion image displayed in the main display area 100) is information about the display of a lesion image displayed in the main display area 100.

The slider 111 moves on the time bar 110 to indicate the time position of the image currently displayed in the main display area 100 and also displays one of the default color, lesion color of bleeding and lesion color of fading. In this case, if the image currently displayed in the main display area 100 is an image other than a lesion image (normal organ image), the display controller 25a sets the display color of the slider 111 to the default color; if the image currently displayed in the main display area 100 is a bleeding image, the display controller 25a sets the display color of the slider 111 to the lesion color (lesion color of bleeding) that is the same as that of the lesion marks 120a and 120b; and, if the image currently displayed in the main display area 100 is a fading image, the display controller 25a sets the display color of the slider 111 to the lesion color (lesion color of fading) that is the same as that of the lesion mark 120c.

Figure 9:
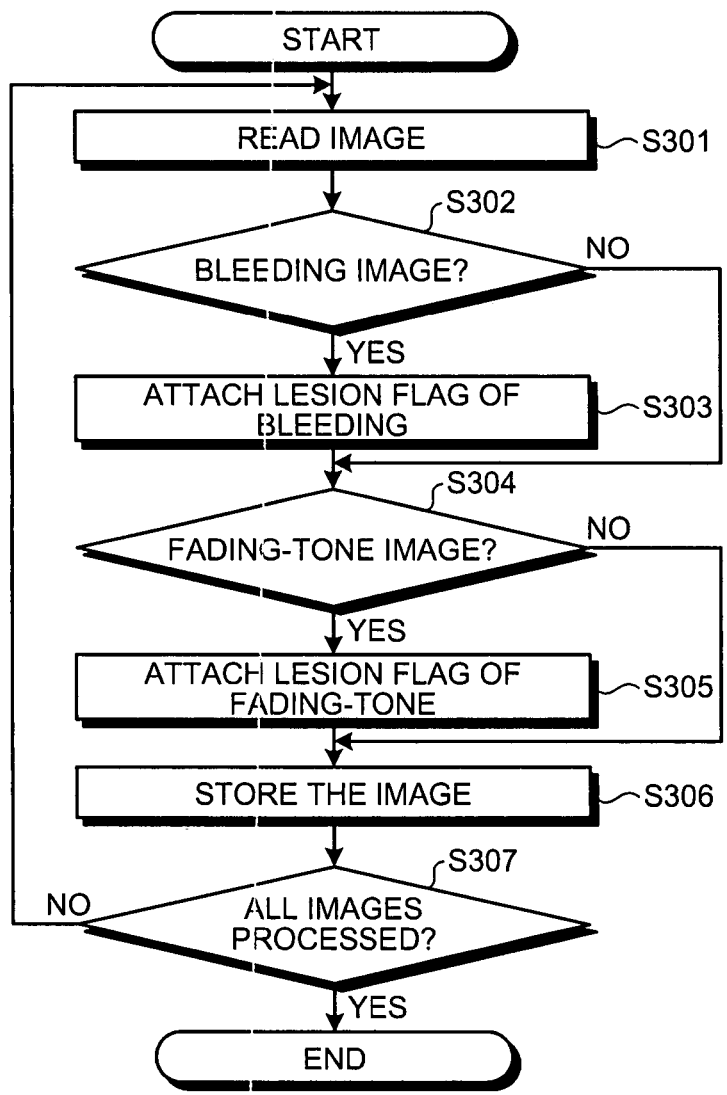
FIG. 9 is a flow chart exemplifying the processing procedure of the control unit for detecting multiple kinds of lesion images contained in the image group inside the subject.

Next, an operation of the control unit 25 for detecting any bleeding image and fading image contained in all in vivo images AI will be described. FIG. 9 is a flow chart exemplifying the processing procedure of the control unit 25 for detecting multiple kinds of lesion images contained in all in vivo images AI. The control unit 25 captures all in vivo images AI from the portable recording medium 5 inserted in the card interface 13 and also detects bleeding images and fading images contained in all in vivo images AI. In this case, the control unit 25 stores all in vivo images AI containing such bleeding images or fading images in the storage unit 14.

More specifically, as shown in FIG. 9, the control unit 25 reads, like the aforementioned step S101, an image to be processed from among all in vivo images AI stored in the portable recording medium 5 inserted in the card interface 13 (step S301)

Next, the control unit 25 determines whether the image inside the subject 1 read as an image to be processed is a bleeding image (step S302). In this case, the lesion detector 25b detects color information of the image inside the subject 1 to be processed and, based on the detected color information, determines whether the image is a bleeding image. More specifically, if the lesion detector 25b detects an average color of the image as the color information and the detected average color of the image closely resembles that of a bleeding image, the lesion detector 25b determines that the image to be processed is a bleeding image inside the subject 1. Also, if the lesion detector 25b detects values of RGB color elements forming the image as the color information and each detected color element value of RGB is within the range of each color element value of a bleeding image, the lesion detector 25b determines that the image to be processed is a bleeding image inside the subject 1. In this manner, the lesion detector 25b detects bleeding images contained in all in vivo images AI.

When the image to be processed is determined to be a bleeding image (step 302, Yes), the control unit 25 attaches a lesion flag to the bleeding image inside the subject 1 (step S303). In this case, the lesion detector 25b attaches a lesion flag of bleeding indicating that the image is a bleeding image to the bleeding image inside the subject 1.

Next, the control unit 25 determines whether the image to be processed is a fading image (step S304). In this case, the lesion detector 25b detects color information of the image inside the subject 1 to be processed and, based on the detected color information, determines whether the image is a fading image. More specifically, if the lesion detector 25b detects an average color of the image as the color information and the detected average color of the image closely resembles that of a fading image, the lesion detector 25b determines that the image to be processed is a fading image inside the subject 1. Also, if the lesion detector 25b detects values of RGB color elements forming the image as the color information and each detected color element value of RGB is within the range of each color element value of a fading image, the lesion detector 25b determines that the image to be processed is a fading image inside the subject 1. In this manner, the lesion detector 25b detects fading images contained in all in vivo images AI.

When the image to be processed is determined to be a fading image (step 304, Yes), the control unit 25 attaches a lesion flag to the fading image inside the subject 1 (step S305). In this case, the lesion detector 25b attaches a lesion flag of fading indicating that the image is a fading image to the fading image inside the subject 1.

Next, the control unit 25 stores the bleeding image with the attached lesion flag of bleeding or the fading image with the attached lesion flag of fading in the storage unit 14 (step S306). In this case, the bleeding image or fading image is stored in the storage unit 14 as part of all in vivo images AI.

Subsequently, like the aforementioned step S105, the control unit 25 determines whether processing of all images contained in all in vivo images AI has been performed (step S307). If the control unit 25 determines that processing of all in vivo images AI has not been completed (step S307, No), the control unit 25 returns to the aforementioned step S301 to repeat the processing procedure of step S301 and thereafter. If, on the other hand, the control unit 25 determines that processing of all images contained in all in vivo images AI has been completed (step S307, Yes), the control unit 25 terminates detection processing of multiple kinds of lesion images contained in all in vivo images AI.

The control unit 25 performs the processing procedure of the aforementioned steps S301 to S307 for each image contained in all in vivo images AI repeatedly and stores all in vivo images AI containing any bleeding image or fading image in the storage unit 14.

Meanwhile, if the control unit 25 determines that an image to be processed is not a bleeding image in the aforementioned step S302 (step S302, No), the control unit 25 proceeds to the aforementioned step S304 to repeat the processing procedure of step S304 and thereafter. In this case, the lesion detector 25b does not attach any lesion flag of bleeding to the image inside the subject 1 that is not a bleeding image.

Also, if the control unit 25 determines that an image to be processed is not a fading image in the aforementioned step S304 (step S304, No), the control unit 25 proceeds to the aforementioned step S306 to repeat the processing procedure of step S306 and thereafter. In this case, the lesion detector 25b does not attach any lesion flag of fading to the image inside the subject 1 that is not a fading image.

As described above, a lesion flag of bleeding is attached to bleeding images inside the subject 1 and a lesion flag of fading is attached to fading images inside the subject 1. On the other hand, neither lesion flag of bleeding nor lesion flag of fading is attached to images inside the subject 1 that are neither bleeding images nor fading images (that is, normal organ images). Such bleeding images, fading images, and normal organ images are stored in the storage unit 14 as all in vivo images AI.

Figure 10:
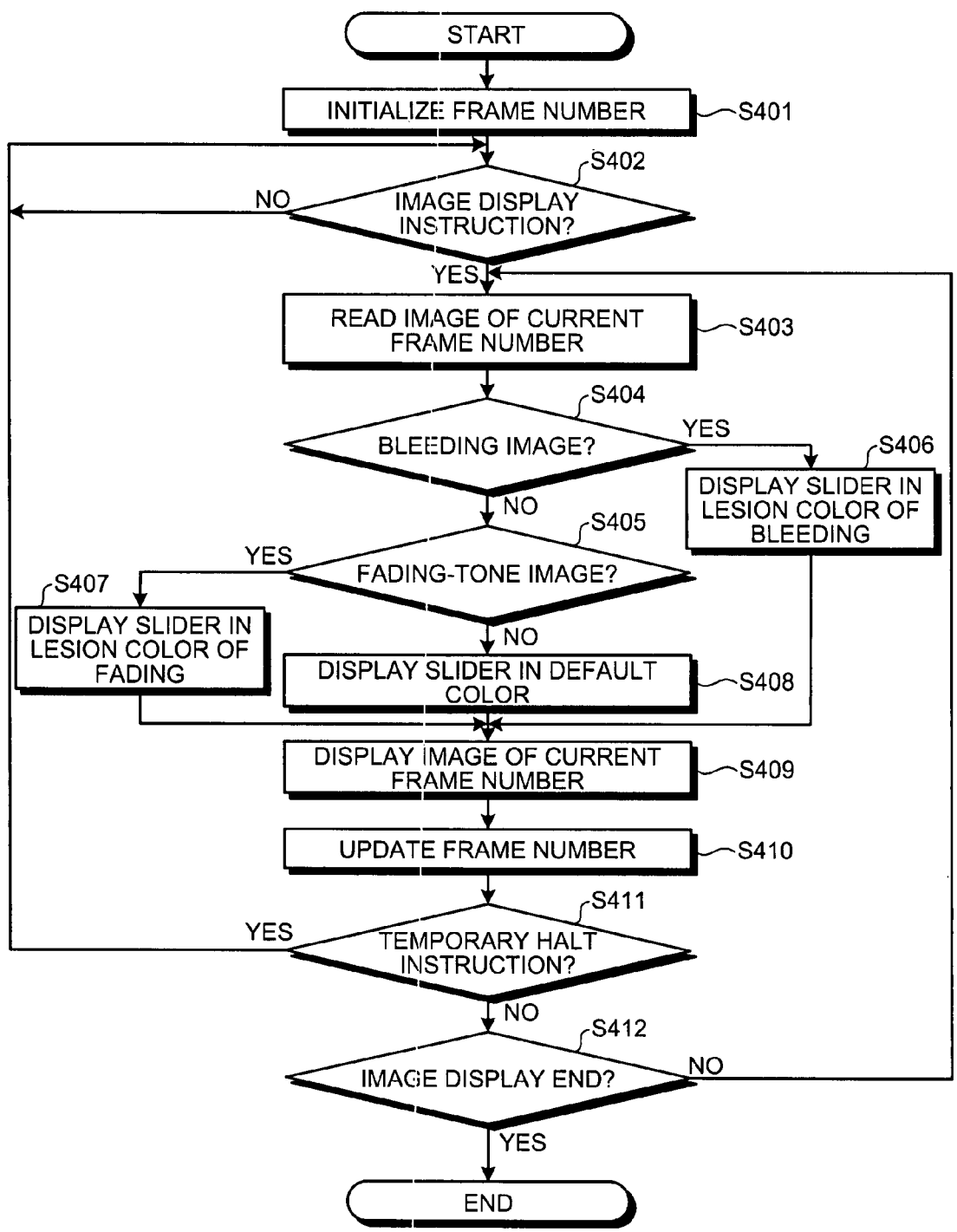
FIG. 10 is a flow chart illustrating the processing procedure of the control unit of the image display device according to the second embodiment.

Next, operations of the control unit 25 to perform control to display in the main display area 100 each image contained in all in vivo images AI and to control the display color of the slider 111 indicating the time position of the image currently displayed in the main display area 100 will be described. FIG. 10 is a flow chart illustrating the processing procedure of the control unit 25 of the image display device 24 according to the second embodiment.

Approximately similarly to the aforementioned control unit 15 of the image display device 4 according to the aforementioned first embodiment, the control unit 25 performs control to display in the main display area 100 each image contained in all in vivo images AI and also controls the display color of the slider 111 indicating the time position of the image currently displayed in the main display area 100. In this case, if the currently displayed image is an image other than a lesion image, the control unit 25 sets the display color of the slider 111 to the default color; if the currently displayed image is a bleeding image, the control unit 25 sets the display color of the slider 111 to the lesion color of bleeding; and if the currently displayed image is a fading image, the control unit 25 sets the display color of the slider 111 to the lesion color of fading.

That is, as shown in FIG. 10, the control unit 25 performs a processing procedure similar to that of the aforementioned steps S201 to S203 (See FIG. 5), initializes the frame number n of all in vivo images AI, determines whether there is any image display instruction, and, if there is an image display instruction, reads the image of the current frame number in all in vivo images AI (steps S401 to S403).

Next, the control unit 25 determines whether the read image of the current frame number (that is, the image inside the subject 1 to be processed for display) is a bleeding image (step S404). In this case, the control unit 25 determines whether a lesion flag of bleeding is attached to the image of the current frame number and, if no lesion flag of bleeding is attached, determines that the image of the current frame number is not a bleeding image.

If the image of the current frame number is determined not to be a bleeding image, as described above (step S404, No), the control unit 25 determines whether the image of the current frame number is a fading image (step S405). In this case, the control unit 25 determines whether a lesion flag of fading is attached to the image of the current frame number and, if no lesion flag of fading is attached, determines that the image of the current frame number is not a fading image.

If the image of the current frame number (image already determined not to be a bleeding image) is determined not to be a fading image (step S405, No), the control unit 25 performs control to display the slider 111 indicating the time position of the image of the current frame number, that is, a normal organ image that is neither bleeding image nor fading image in the default color (step S408).

If, on the other hand, a lesion flag of bleeding is attached to the image of the current frame number in step S404, the display controller 25*a* determines that the image of the current frame number is a bleeding image. If the image of the current frame number is determined to be a bleeding image, as described above (step S404, Yes), the control unit 25 performs control to display the slider 111 indicating the time position of the image of the current frame number, that is, the bleeding image in the lesion color of bleeding (step S406). In this case, the display controller 25*a* causes the slider 111 to move to the time position on the time bar 110 corresponding to the image of the current frame number, which is a bleeding image, and performs control to display the slider 111 indicating the time position of the image of the current frame number, which is the aforementioned bleeding image, in the lesion color of bleeding (for example, red).

If a lesion flag of fading is attached to the image of the current frame number in step S405, the display controller 25*a* determines that the image of the current frame number is a fading image. If the image of the current frame number is determined to be a fading image, as described above (step S405, Yes), the control unit 25 performs control to display the slider 111 indicating the time position of the image of the current frame number, that is, the fading image in the lesion color of fading (step S407). In this case, the display controller 25*a* causes the slider 111 to move to the time position on the time bar 110 corresponding to the image of the current frame number, which is a fading image, and performs control to display the slider 111 indicating the time position of the image of the current frame number, which is the aforementioned fading image, in the lesion color of fading (for example, white).

Subsequently, the control unit 25 performs control to display the image of the current frame number in the main display area 100 (step S409). Meanwhile, the frame number of the image displayed in the main display area 100 (that is, the current frame number) in step S409 is the frame number initialized in the aforementioned step S401 or the frame number updated in step S410 described later.

If, in step S409, the image of the current frame number is a normal organ image, the normal organ image of the current frame number is made to be displayed in the main display area 100 by the display controller 25*a*. In this case, the normal organ image inside the subject 1 is displayed in the main display area 100 and also the slider 111 indicating the time position of the normal organ image inside the subject 1 currently displayed in the main display area 100 is displayed in the default color.

If the image of the current frame number is a bleeding image, on the other hand, the bleeding image of the current frame number is made to be displayed in the main display area 100 by the display controller 25*a*. In this case, the bleeding image inside the subject 1 is displayed in the main display area 100 and also the slider 111 indicating the time position of the bleeding image inside the subject 1 currently displayed in the main display area 100 is displayed in the lesion color of bleeding. Here, the lesion color of bleeding displayed in the slider 111 is a color corresponding to the lesion indicated by the bleeding image (that is, a bleeding site), which is the currently displayed image in the main display area 100, and is the same color as the lesion color of a lesion mark (for example, the lesion mark 120*a*) in the mark display area 120 indicating the time position of the bleeding image.

If the image of the current frame number is a fading image, the fading image of the current frame number is made to be displayed in the main display area 100 by the display controller 25*a*. In this case, the fading image inside the subject 1 is displayed in the main display area 100 and also the slider 111 indicating the time position of the fading image inside the subject 1 currently displayed in the main display area 100 is displayed in the lesion color of fading. Here, the lesion color of fading displayed in the slider 111 is a color corresponding to the lesion indicated by the fading image (that is, a fading site), which is the currently displayed image in the main display area 100, and is the same color as the lesion color of a lesion mark (for example, the lesion mark 120*c*) in the mark display area 120 indicating the time position of the fading image.

Subsequently, like the aforementioned step S208, the control unit 25 updates the frame number n of all in vivo images AI to be processed for display (step S410). Then, like the aforementioned step S209, the control unit 25 determines whether there is any temporary halt instruction of the image displayed in the main display area 100 (step S411) and, if there is a temporary halt instruction (step S411, Yes), the control unit 25 returns to step S402 to repeat the processing procedure of step S402 and thereafter.

If, on the other hand, there is no temporary halt instruction (step S411, No), like the aforementioned step S210, the control unit 25 determines whether image display processing to display in the main display area 100 images contained in all in vivo images AI has terminated (step S412). If the control unit 25 determines that image display processing has not terminated (step S412, No), the control unit 25 returns to step S403 to repeat the processing procedure of step S403 and thereafter and, if the control unit 25 determines that image display processing has terminated (step S412, Yes), the control unit 25 terminates image display processing of images inside the subject 1.

Figure 11:
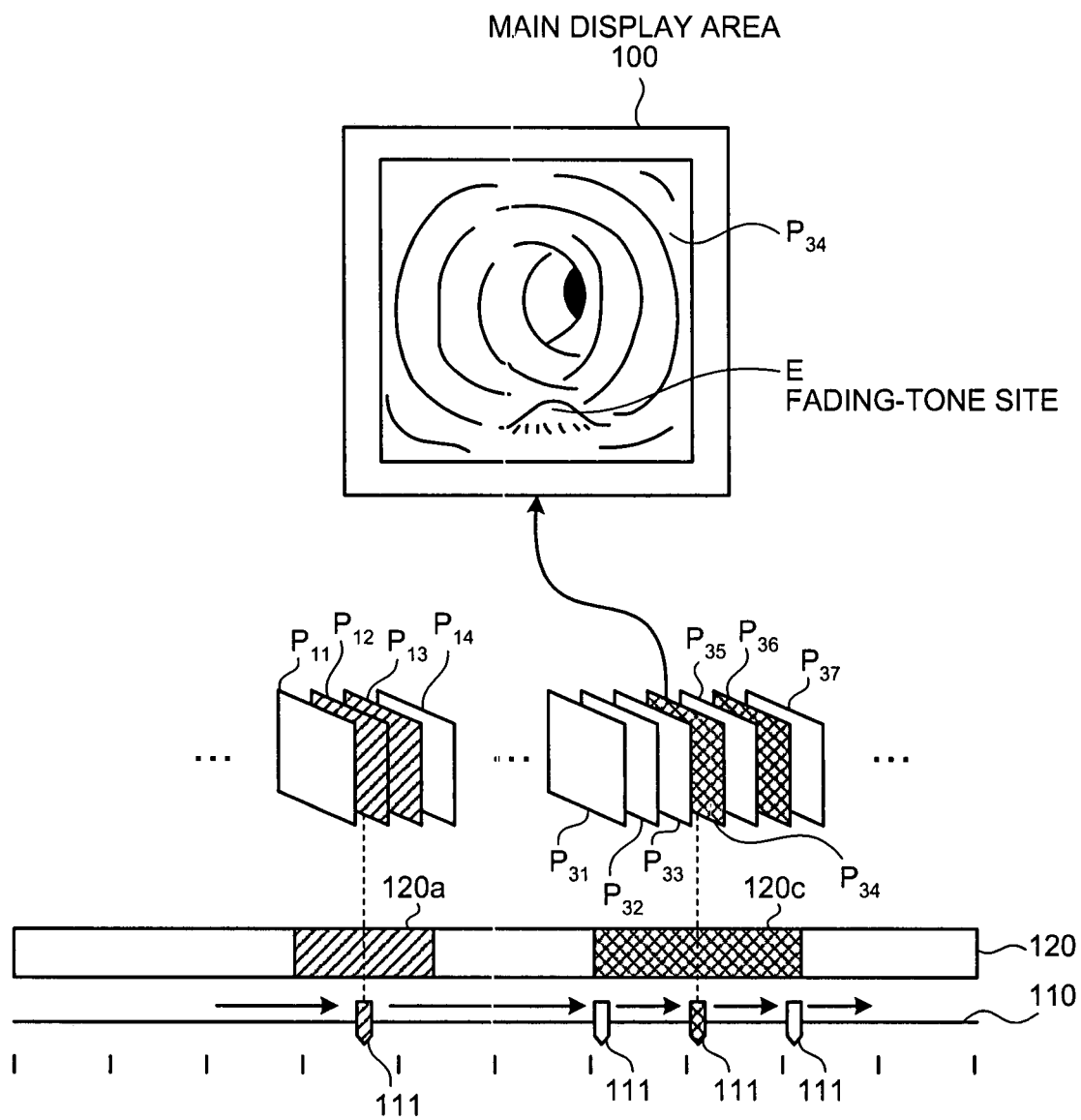
FIG. 11 is a schematic view illustrating an operation of the control unit changing the display color of the slider to the lesion color of bleeding or fading.

Next, a case in which a bleeding site and fading image, which are an example of multiple kinds of lesion images, are displayed in the main display area 100 will be exemplified to concretely describe an operation of the control unit 25 that performs control to change the display color of the slider 111 indicating the time position of a bleeding image to the lesion color of bleeding and to change the display color of the slider 111 indicating the time position of a fading image to the lesion color of fading. FIG. 11 is a schematic view illustrating an operation of the control unit 25 changing the display color of the slider 111 to the lesion color of bleeding or fading depending on a bleeding image or fading image currently displayed.

Before making each image contained in all in vivo images AI to be displayed in the main display area 100, the control unit 25 causes the mark display area 120 to display a lesion mark indicating the time position of a bleeding image contained in all in vivo images AI and that indicating the time position of a fading image contained in all in vivo images AI.

More specifically, if, for example, fading images $P_{34}$ and $P_{36}$ contained in all in vivo images AI are detected, the control unit 25 causes the mark display area 120 to display the lesion mark 120c indicating the time positions of the fading images $P_{34}$ and $P_{36}$. In this case, the display controller 25a performs control to display the lesion mark 120c in the lesion color (for example, white) corresponding to a fading site shown in the fading images $P_{34}$ and $P_{36}$. Also, like the aforementioned first embodiment, the display controller 25a causes the mark display area 120 to display the lesion mark 120a indicating the time positions of the bleeding images $P_{12}$ and $P_{13}$ inside the subject 1 in the lesion color of bleeding (for example, red).

The lesion marks 120a and 120c are displayed, as shown in FIG. 6, for example, at the time positions in the mark display area 120 corresponding to the bleeding images $P_{12}$ and $P_{13}$ and at the time positions in the mark display area 120 corresponding to the fading images $P_{34}$ and $P_{36}$ in a bar form respectively. As described above, the lesion mark 120a in a bar form represents a partial image group containing the images $P_{11}$ and $P_{14}$ and the bleeding images $P_{12}$ and $P_{13}$ inside the subject 1. The lesion mark 120c in a bar form, on the other hand, represents a partial image group containing the fading images $P_{34}$ and $P_{36}$ from among all in vivo images AI. Such a partial image group includes, for example, the fading images $P_{34}$ and $P_{36}$ and images $P_{31}$, $P_{32}$, $P_{33}$, $P_{35}$, and $P_{37}$. The images $P_{31}$, $P_{32}$, $P_{33}$, $P_{35}$, and $P_{37}$ inside the subject 1 are images near the frame numbers of the fading images $P_{34}$ and $P_{36}$ and in which normal organ interiors are picked up.

Subsequently, based on display instruction information input by the input unit 11, the control unit 25 performs control to display in the main display area 100 the image $P_n$ (n=1, 2, 3, ...) contained in the group of images inside the subject 1 and also causes the slider 111 to move along the time bar 110 to indicate the time position of the image currently displayed in the main display area 100. In this case, if the image currently displayed in the main display area 100 is not a lesion image, the control unit 25 performs control to display the slider 111 indicating the time position of the currently displayed image in the default color. If, on the other hand, the image currently displayed in the main display area 100 is a bleeding image, the control unit 25 performs control to display the slider 111 indicating the time position of the bleeding image in the lesion color of bleeding and, if the image currently displayed in the main display area 100 is a fading image, the control unit 25 performs control to display the slider 111 indicating the time position of the fading image in the lesion color of fading.

More specifically, as shown in FIG. 11, if the image currently displayed in the main display area 100 is the bleeding image $P_{12}$ or $P_{13}$, the control unit 25 performs control to change the default color of the slider 111 positioned within the display range of the lesion mark 120a to the lesion color of bleeding. In this case, the control unit 25 changes the display color of the slider 111 indicating the time positions of the bleeding image $P_{12}$ or $P_{13}$ to the lesion color of bleeding (for example, red), which is the same color as that of the lesion mark 120a. If the image currently displayed in the main display area 100 is a normal organ image like $P_{11}$ and $P_{14}$, the control unit 25 sets the display color of the slider 111 to the default color even if the slider 111 is positioned within the display range the lesion mark 120a.

Also, if the image currently displayed in the main display area 100 is a normal organ image like $P_{31}$, $P_{32}$, $P_{33}$, $P_{35}$, and $P_{37}$, the control unit 25 sets the display color of the slider 111 to the default color even if the slider 111 is positioned within the display range of the lesion mark 120c. If, on the other hand, the image currently displayed in the main display area 100 is the fading image $P_{34}$ or $P_{36}$, the control unit 25 performs control to change the default color of the slider 111 positioned within the display range of the lesion mark 120c to the lesion color of fading. In this case, the control unit 25 changes the display color of the slider 111 indicating the time positions of the fading images $P_{34}$ and $P_{36}$ to the lesion color of fading (for example, white), which is the same color as that of the lesion mark 120c.

Through control of the display color of the slider 111 by the control unit 25, as described above, the slider 111 can not only indicate the time position of the currently displayed image in all in vivo images AI, but also display whether the currently displayed image is a lesion image by its display color (for example, the default color, lesion color of bleeding, or lesion color of fading) and further whether the lesion image is a bleeding image or fading image. The slider 111 described above is displayed apart from the image currently displayed in the main display area 100. Thus, the slider 111 does not disturb observation of the image currently displayed in the main display area 100 even if its display color changes to multiple kinds of lesion colors or the default color.

Therefore, a user such as a physician and nurse can observe the image currently displayed in the main display area 100 without being disturbed by change in display color of the slider 111 and also understand easily that, by visually confirming the lesion color of the slider 111, the currently displayed image is a lesion image and, in that case, the kind of lesion (a bleeding site or fading site) indicated by the lesion image. As a result, while the slider 111 is positioned within the display range of the lesion mark displayed by the mark display area 120, the user can easily search for and display lesion images from among a partial image group inside the subject 1 successively displayed in the main display area 100 and easily identify the kind of lesion (a bleeding site or fading site) indicated by the lesion image even if multiple kinds of lesion images are contained in all in vivo images AI.

More specifically, while the slider 111 is positioned within the display range of the lesion mark 120a displayed in a bar form, the user can easily identify the bleeding images $P_{12}$ and $P_{13}$ from among the partial image group (each image whose frame number is n=11 to 14) inside the subject 1 successively displayed in the main display area 100. Accordingly, the bleeding images $P_{12}$ and $P_{13}$ can easily be displayed in the main display area 100 and also the bleeding site BL inside the subject 1 contained as a photographic object of the bleeding images $P_{12}$ and $P_{13}$ can easily be observed.

Also, while the slider 111 is positioned within the display range of the lesion mark 120c displayed in a bar form, the user can easily identify the fading images $P_{34}$ and $P_{36}$ from among the partial image group (each image whose frame number is n=31 to 37) inside the subject 1 successively displayed in the main display area 100. Accordingly, the fading images $P_{34}$ and $P_{36}$ can easily be displayed in the main display area 100 and also the fading site E inside the subject 1 contained as a photographic object of the fading images $P_{34}$ and $P_{36}$ can easily be observed.

As has been described, in the second embodiment of the present invention, the image display device is configured in such ways that, in addition to the functions of the aforementioned first embodiment, multiple kinds of lesion images contained in a group of images inside a subject are detected and a plurality of lesion marks indicating each time position of such multiple kinds of lesion images are displayed in a lesion color that is different for each kind of lesion. Also, a slider indicating the time position of the image currently displayed in a main display area is displayed in a default color and, if the image currently displayed in the main display area is one of the multiple kinds of lesion images, the default color of the slider is changed to the lesion color that is different for each kind of lesion image. Thus, by visually confirming the display color (the lesion color or default color) of the slider, whether the currently displayed image in the main display area is a lesion image can easily be determined and also the kind of lesion indicated by the lesion image can easily be determined even if multiple kinds of lesion images are contained in the group of images inside the subject to be processed for display. As a result, operation effects of the aforementioned first embodiment can be gained and also the kind of multiple kinds of lesion images contained in the group of images inside the subject can easily be identified so that an image display device that can easily display a desired lesion image from among the group of images inside the subject can be realized.

In an image display device according to the second embodiment of the present invention, even if multiple kinds of lesion images are mixed in a group of images inside a subject, lesion images in which a desired lesion (for example, a bleeding site and fading site) is picked up can be searched for and displayed from such multiple kinds of lesion images. As a result, multiple kinds of lesion images contained in the group of images inside the subject can easily be observed.

Third Embodiment

Next, a third embodiment of the present invention will be described. In the aforementioned second embodiment, multiple kinds of lesion images contained in all in vivo images AI are detected and the slider 111 is displayed in the lesion color that is different for each lesion indicated by each of the multiple kinds of lesion images, but in the third embodiment, an image display device is configured in such ways that desired lesions can further be selected from the multiple kinds of lesions indicated by the multiple kinds of lesion images to display the lesion colors of the lesion marks and the slider 111 corresponding to the selected desired lesions.

Figure 12:
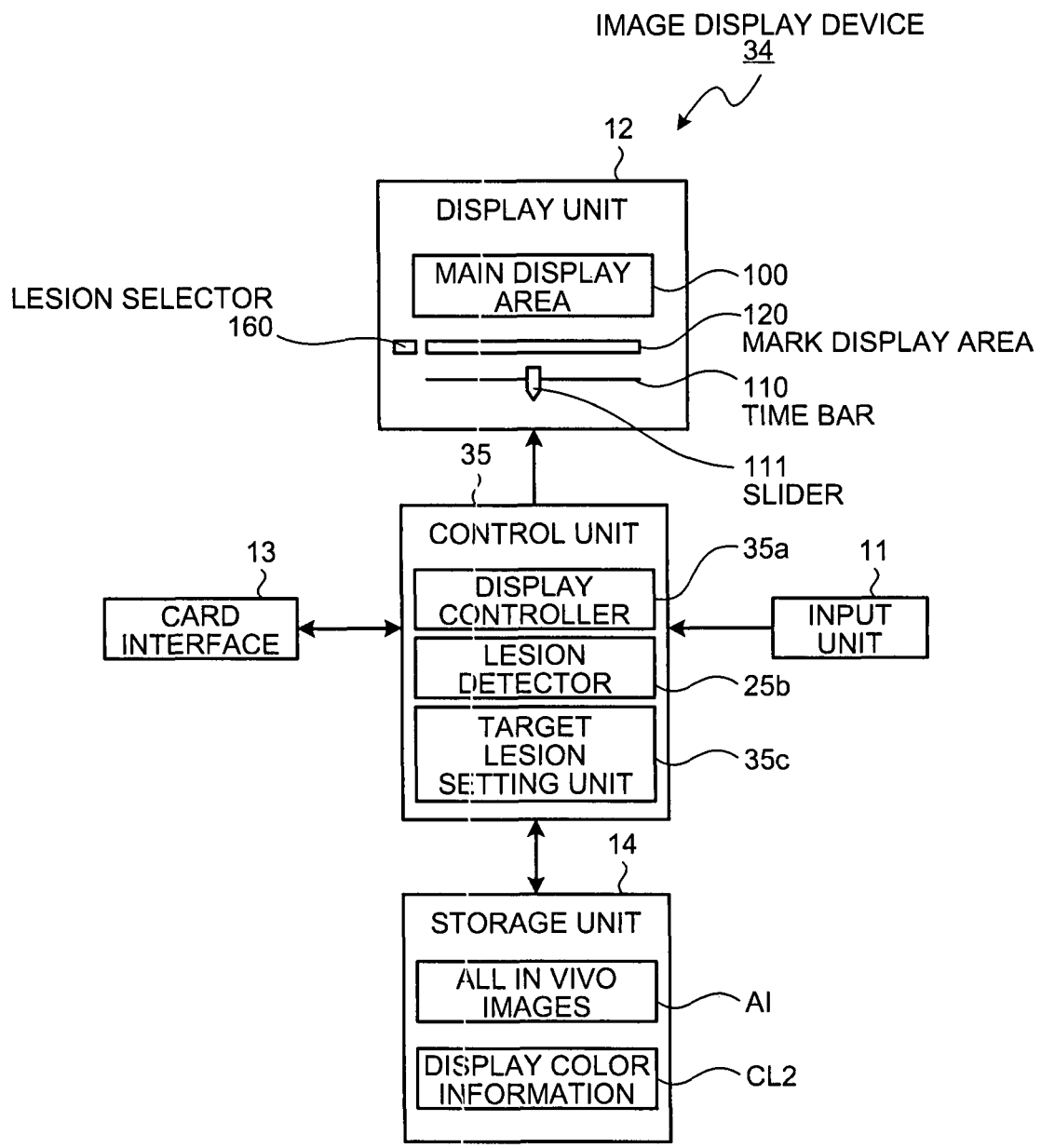
FIG. 12 is a block diagram schematically showing a configuration example of an image display device according to a third embodiment of the present invention.

FIG. 12 is a block diagram schematically showing a configuration example of an image display device according to the third embodiment of the present invention. As shown in FIG. 12, an image display device 34 according to the third embodiment has a control unit 35 instead of the control unit 25 of the image display device 24 according to the aforementioned second embodiment. In the image display device 34, the display unit 12 further displays a lesion selector 160, which is a GUI for selecting desired lesions. An in-vivo information acquiring system according to the third embodiment of the present invention has the image display device 34 instead of the image display device 24 in the in-vivo information acquiring system according to the aforementioned second embodiment. Other components are the same as those of the second embodiment and the same numeral is attached to the same component.

Approximately similarly to the control unit 25 of the image display device 24 according to the aforementioned second embodiment, the control unit 35 controls each of the input unit 11, display unit 12, card interface 13, and storage unit 14, and also controls input/output of information between such components. In addition to the control function described above, the control unit 35 controls the mark control unit 120 to display only lesion marks in the lesion color corresponding to lesions selected by the lesion selector 160 displayed in the display unit 12. When a lesion image containing a lesion selected by the lesion selector 160 as a photographic object is displayed in the main display area 100, the control unit 35 performs control to display the slider 111 in the lesion color corresponding to the selected lesion. The control unit 35 described above has the aforementioned lesion detector 25b and a display controller 35a instead of the display controller 25a of the control unit 25 in the second embodiment. Further, the control unit 35 has a target lesion setting unit 35c for setting a lesion selected by the lesion selector 160 as a lesion to be processed (target lesion).

The display controller 35a has a function approximately similar to that of the aforementioned display controller 25a of the control unit 25. More specifically, the display controller 35a performs control to display in the main display area 100 each image in all in vivo images AI containing, for example, bleeding images and fading images and, at the same time, causes the slider 111 to move along the time bar 110 so that the slider 111 indicates the time position of the image currently displayed in the main display area 100. If the image currently displayed in the main display area 100 is an image other than a lesion image (that is, a normal organ image), the display controller 35a performs control to display the slider 111 indicating the time position of the currently displayed image in the default color. If, on the other hand, a bleeding site is set as a target lesion by the target lesion setting unit 35c and the image currently displayed in the main display area 100 is a bleeding image, the display controller 35a performs control to change the display color of the slider 111 indicating the time position of the bleeding image to the lesion color of bleeding. If a fading site is set as a target lesion by the target lesion setting unit 35c and the image currently displayed in the main display area 100 is a fading image, the display controller 35a performs control to change the display color of the slider 111 indicating the time position of the fading image to the lesion color of fading.

The display controller 35a also causes the mark display area 120 to display, among a plurality of lesion marks corresponding to each of multiple kinds of lesion images (for example, bleeding images and fading images) contained in all in vivo images AI, one or more lesion marks corresponding to one or more lesions set by the target lesion setting unit 35c as target lesions. More specifically, if a bleeding site is set by the target lesion setting unit 35c as a target lesion, the display controller 35a controls the mark display area 120 to display lesion marks indicating the time positions of bleeding images in all in vivo images AI detected by the lesion detector 25b in the lesion color of bleeding. If, on the other hand, a fading site is set by the target lesion setting unit 35c as a target lesion, the display controller 35a controls the mark display area 120 to display legion marks indicating the time positions of fading images in all in vivo images AI detected by the lesion detector 25b in the lesion color of fading. Also, if a bleeding site and fading site are set by the target lesion setting unit 35c as target lesions, the display controller 35a controls the mark display area 120 to display lesion marks indicating the time positions of bleeding images in all in vivo images AI detected by the lesion detector 25b in the lesion color of bleeding and legion marks indicating the time positions of fading images in all in vivo images AI in the lesion color of fading.

The target lesion setting unit 35c sets one or more lesions selected by the lesion selector 160, which is a GUI displayed in the display unit 12, as target lesions. Such target lesions set by the target lesion setting unit 35c are display processing target lesions corresponding to lesion marks displayed by the mark display area 120 and also display processing target lesions corresponding to the lesion color displayed in the slider 111 when the image currently displayed in the main display area 100 is a lesion. More specifically, if a bleeding site is selected by the lesion selector 160, the target lesion setting unit 35c sets the bleeding site as a target lesion and, if a fading site is selected by the lesion selector 160, the target lesion setting unit 35c sets the fading site as a target lesion. If a bleeding site and a fading site are selected by the lesion selector 160, the target lesion setting unit 35c sets the bleeding site and fading site as target lesions.

Figure 13:
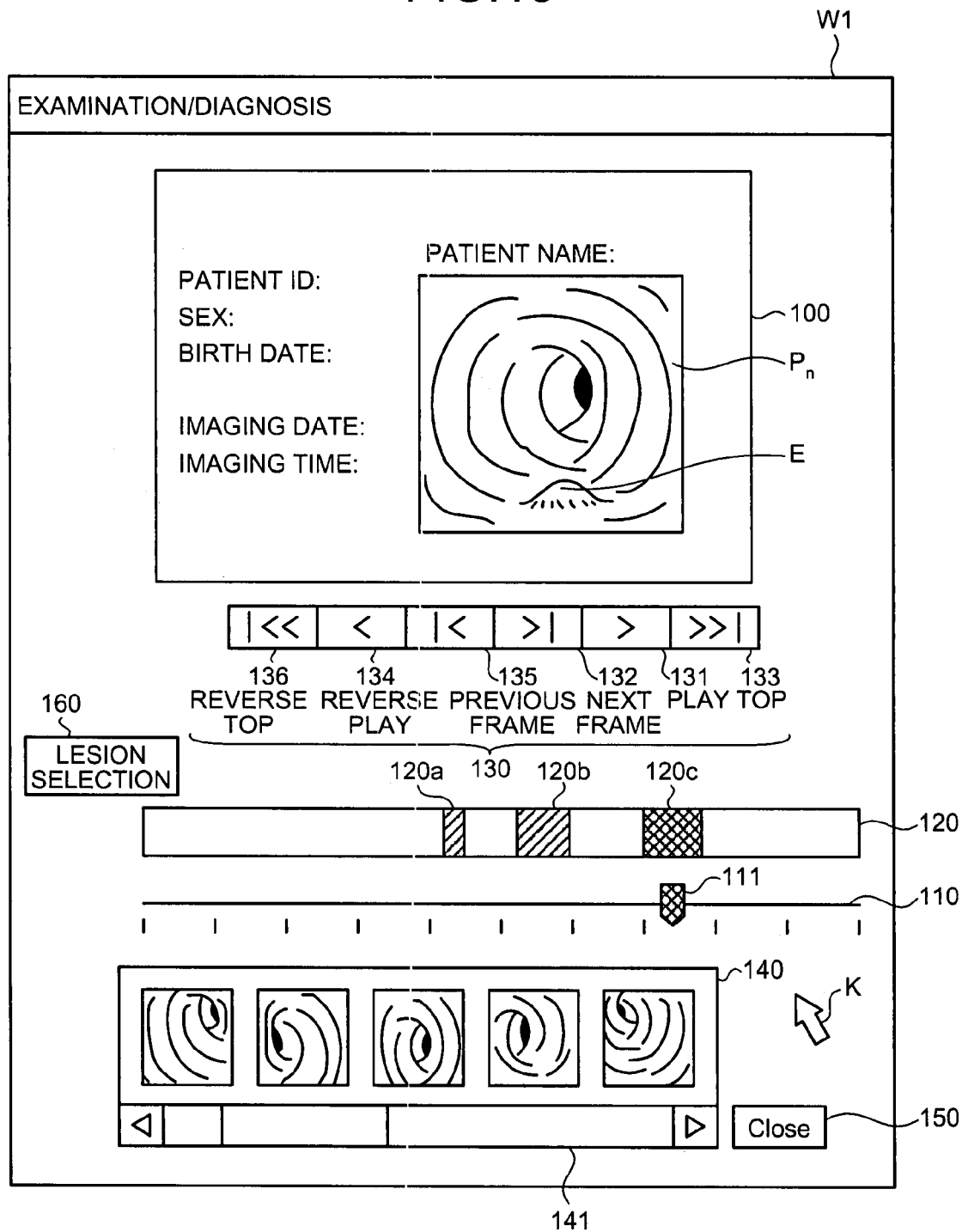
FIG. 13 is a schematic view exemplifying the display mode of the display unit further displaying a lesion selector, which is a GUI for selecting a desired lesion.

Next, the display mode of the display unit 12 will be concretely exemplified to describe an operation of the display controller 35a to control GUI displayed in the display unit 12 and a display operation of the display unit 12. FIG. 13 is a schematic view exemplifying the display mode of the control unit 12 further displaying the lesion selector (shown as "LESION SELECTION") 160, which is a GUI for selecting a desired lesion.

As shown in FIG. 13, the lesion selector 160, which is a GUI for selecting a desired lesion, is additionally formed in the window W1 displayed in the display unit 12 of the image display device 34. If the image currently displayed in the main display area 100 is a lesion image and the lesion indicated by the lesion image is a lesion selected by the lesion selector 160, the slider 111 displays the lesion color corresponding to the selected lesion. If the lesion indicated by the lesion image is not a lesion selected by the lesion selector 160, the slider 111 displays the default color even if the currently displayed image is a lesion image. The mark display area 120 displays one or more lesion marks corresponding to lesions selected by the lesion selector 160, for example, the aforementioned lesion marks 120a, 120b, and 120c. Other display modes of the window W1 are the same as those of the aforementioned second embodiment.

As described above, the lesion selector 160 is a GUI to select desired lesions from among multiple kinds of lesions (for example, a bleeding site and fading site) and is displayed in the display unit 12, for example, as a push button. The lesion selector 160 described above makes a selection of one or more desired lesions through a click operation or the like using the input unit 11. More specifically, the lesion selector 160 opens a predetermined selection menu through a click operation or the like using the input unit 11 to select one or more lesions from multiple kinds of lesions listed in the selection menu. One or more lesions selected by the lesion selector 160 are set by the aforementioned target lesion setting unit 35c as one or more target lesions.

Figure 14:
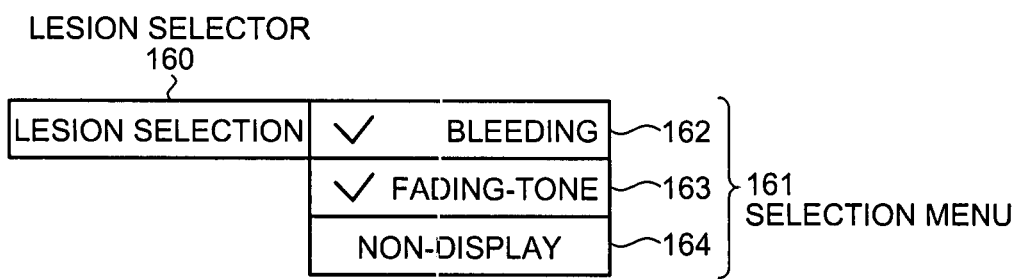
FIG. 14 is a schematic view showing a concrete example of a selection menu shown by the lesion selector.

FIG. 14 is a schematic view showing a concrete example of the selection menu shown by the lesion selector 160. As shown in FIG. 14, the lesion selector 160 opens a selection menu 161 listing, for example, bleeding (site) and fading (site) as lesions. The selection menu 161 contains a bleeding selector 162 for selecting a bleeding site as a processing target lesion and a fading selector 163 for selecting a fading site as a processing target lesion.

More specifically, the bleeding selector 162 selects a bleeding site as a desired lesion through a click operation or the like using the input unit 11 and displays a mark (for example, a ∨ mark shown in FIG. 14) indicating that the bleeding site has been selected. In this case, the input unit 11 inputs selection information that a bleeding site will be selected into the control unit 35. Based on the selection information of the bleeding site input by the input unit 11, the aforementioned target lesion setting unit 35c sets the bleeding site as a target lesion.

The fading selector 163 selects a fading site as a desired lesion through a click operation or the like using the input unit 11 and displays a mark (for example, the ∨ mark shown in FIG. 14) indicating that the fading site has been selected. In this case, the input unit 11 inputs selection information that a fading site will be selected into the control unit 35. Based on the selection information of the fading site input by the input unit 11, the aforementioned target lesion setting unit 35c sets the fading site as a target lesion.

As shown in FIG. 14, the selection menu 161 further contains a non-display selector 164. The non-display selector 164 selects a state in which no lesion mark of any lesion such as a bleeding site and fading site is displayed. More specifically, the non-display selector 164 selects a non-display state of lesion marks through a click operation or the like using the input unit 11 and displays a mark (for example, the ∨ mark) indicating that the non-display state has been selected. In this case, the input unit 11 inputs selection information that a non-display state will be selected into the control unit 35. Based on the selection information of the non-display state input by the input unit 11, the display controller 35a performs control not to display any lesion mark (for example, the lesion marks 120a, 120b, and 120c shown in FIG. 13) of lesion. Through control of the display controller 35a, no lesion mark is displayed in the mark display area 120 even if a lesion image is detected in all in vivo images AI by the aforementioned lesion detector 25b. Meanwhile, based on the selection information of the non-display state input by the input unit 11, the display controller 35a may control the display unit 12 not to display the mark display area 120, thereby preventing displaying of any lesion mark of lesion.

Figure 15:
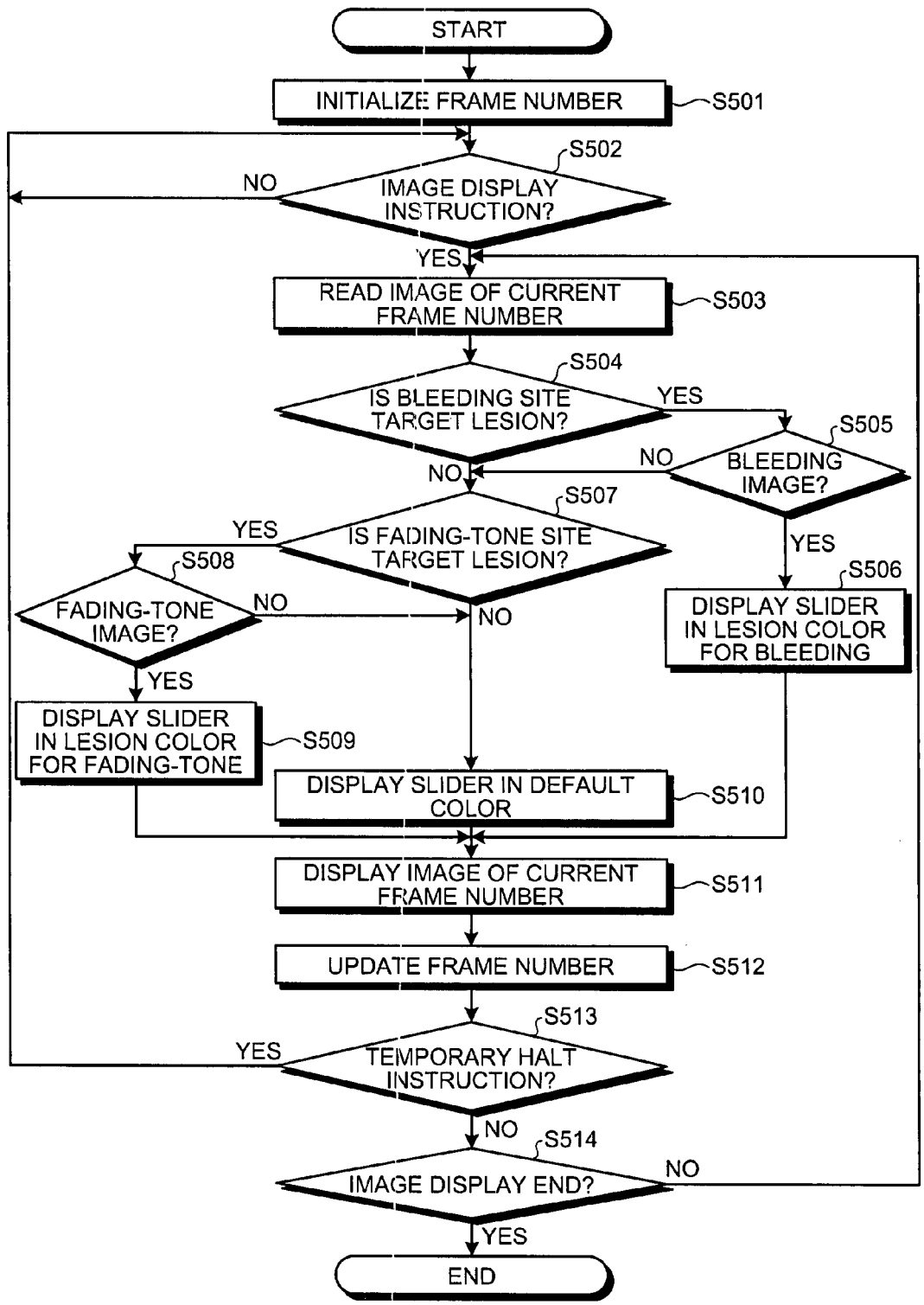
FIG. 15 is a flow chart illustrating the processing procedure of the control unit of the image display device according to the third embodiment.

Next, operations of the control unit 35 to perform control to display in the main display area 100 each image contained in all in vivo images AI and to control the display color of the slider 111 indicating the time position of the image currently displayed in the main display area 100 will be described. FIG. 15 is a flow chart illustrating the processing procedure of the control unit 35 of the image display device 34 according to the third embodiment.

Approximately similarly to the aforementioned control unit 25 of the image display device 24 according to aforementioned the second embodiment, the control unit 35 performs control to display in the main display area 100 each image contained in all in vivo images AI and also controls the display color of the slider 111 indicating the time position of the image currently displayed in the main display area 100. In this case, if the currently displayed image is an image other than a lesion image, the control unit 35 sets the display color of the slider 111 to the default color. If, while the bleeding site is set as a target lesion, the currently displayed image is a bleeding image, the control unit 35 sets the display color of the slider 111 to the lesion color of bleeding. If, while the fading site is set as a target lesion, the currently displayed image is a fading image, the control unit 35 sets the display color of the slider 111 to the lesion color of fading.

That is, as shown in FIG. 15, the control unit 35 performs a processing procedure similar to that of the aforementioned steps S401 to S403 (See FIG. 10), initializes the frame number n of all in vivo images AI, determines whether there is any image display instruction, and, if there is an image display instruction, reads the image of the current frame number in all in vivo images AI (steps S501 to S503).

Next, the control unit 35 determines the lesion selected by the aforementioned lesion selector 160 (that is, a target lesion). In this case, the control unit 35 determines whether, for example, the bleeding site is a target lesion (step S504). More specifically, if the bleeding site is selected by the lesion selector 160, the target lesion setting unit 35c sets the bleeding site as a target lesion based on selection information of the bleeding site input by the input unit 11. Thus, if the target lesion setting unit 35c sets the bleeding site as a target lesion, the control unit 35 determines that the bleeding site is a target lesion (step S504, Yes) and determines whether the image of the current frame number read in step S503 (that is, the image inside the subject 1 to be processed for display) is a bleeding image (step S505). In this case, like the aforementioned step S404, if a lesion flag of bleeding is attached to the image of the current frame number, the display controller 35a determines that the image of the current frame number is a bleeding image and, if no lesion flag of bleeding is attached to the image of the current frame number, the display controller 35a determines that the image of the current frame number is not a bleeding image.

Thus, if the control unit 35 determines that the image of the current frame number is a bleeding image while the bleeding site is set as a target lesion (step S505, Yes), like the aforementioned step S406, the control unit 35 performs control to display the slider 111 indicating the time position of the image of the current frame number, that is, the bleeding image in the lesion color of bleeding (step S506). In this case, the display controller 35a causes the slider 111 to move to the time position on the time bar 110 corresponding to the image of the current frame number, which is a bleeding image, and performs control to display the slider 111 indicating the time position of the image of the current frame number, which is the aforementioned bleeding image, in the lesion color of bleeding (for example, red).

If, on the other hand, a bleeding site is not selected by the lesion selector 160, the target lesion setting unit 35c does not set the bleeding site as a target lesion. Thus, if the target lesion setting unit 35c does not set the bleeding site as a target lesion, the control unit 35 determines that the bleeding site is not a target lesion (step S504, No) and determines whether a fading site is a target lesion (step S507). More specifically, if a fading site is selected by the lesion selector 160, the target lesion setting unit 35c sets the fading site as a target lesion based on selection information of the fading site input by the input unit 11. Thus, if the target lesion setting unit 35c sets the fading site as a target lesion, the control unit 35 determines that the fading site is a target lesion (step S507, yes) and determines whether the image of the current frame number read in step S503 (that is, the image inside the subject 1 to be processed for display) is a fading image (step S508). In this case, like the aforementioned step S405, if a lesion flag of fading is attached to the image of the current frame number, the display controller 35a determines that the image of the current frame number is a fading image and, if no lesion flag of fading is attached to the image of the current frame number, the display controller 35a determines that the image of the current frame number is not a fading image.

Thus, if the control unit 35 determines that the image of the current frame number is a fading image while the fading site is set as a target lesion (step S508, Yes), like the aforementioned step S407, the control unit 35 performs control to display the slider 111 indicating the time position of the image of the current frame number, that is, the fading image in the lesion color of fading (step S509). In this case, the display controller 35a causes the slider 111 to move to the time position on the time bar 110 corresponding to the image of the current frame number, which is a fading image, and performs control to display the slider 111 indicating the time position of the image of the current frame number, which is the aforementioned fading image, in the lesion color of fading (for example, while).

If, on the other hand, a fading site is not selected by the lesion selector 160, the target lesion setting unit 35c does not set the fading site as a target lesion. Thus, if the target lesion setting unit 35c does not set the fading site as a target lesion, the control unit 35 determines that the fading site is not a target lesion (step S507, No) and, like the aforementioned step S408, performs control to display the slider 111 indicating the time position of the image of the current frame number in the default color (step S510).

If the control unit 35 determines in the aforementioned step S505 that the image of the current frame number is not a bleeding image (step S505, No), the control unit 35 proceeds to step S507 to repeat the processing procedure of step S507 and thereafter. If the control unit 35 determines in the aforementioned step S508 that the image of the current frame number is not a fading image (step S508, No), the control unit 35 proceeds to step S510 to repeat the processing procedure of step S510 and thereafter.

That is, if neither bleeding site nor fading site is a target lesion, the display controller 35a performs control in step S510 to display the slider 111 indicating the time position of the image of the current frame number in the default color (for example, gray). In this case, the display controller 35a sets the display color of the slider 111 to the default color regardless of content of the image of the current frame number (that is, regardless of a normal organ image or lesion image). If only the bleeding site of the bleeding site and fading site is set as a target lesion and the image of the current frame number is not a bleeding image, the display controller 35a performs control in step S510 to display the slider 111 indicating the time position of the image of the current frame number in the default color. In this case, the display controller 35a sets the display color of the slider 111 to the default color even if the image of the current frame number is a fading image. If only the fading site of the bleeding site and fading site is set as a target lesion and the image of the current frame number is not a fading image, the display controller 35a performs control in step S510 to display the slider 111 indicating the time position of the image of the current frame number in the default color (for example, gray). In this case, the display controller 35a sets the display color of the slider 111 to the default color even if the image of the current frame number is a bleeding image.

Subsequently, like the aforementioned step S409, the control unit 35 performs control to display the image of the current frame number in the main display area 100 (step S511). In this case, if the image of the current frame number is a normal organ image, the normal organ image of the current frame number is made to be displayed in the main display area 100 by display controller 35a; if the image of the current frame number is a bleeding image, the bleeding image of the current frame number is made to be displayed in the main display area 100; and if the image of the current frame number is a fading image, the fading image of the current frame number is made to be displayed in the main display area 100.

Meanwhile, the frame number of the image displayed in the main display area 100 (that is, the current frame number) in step S511 is the frame number initialized in the aforementioned step S501 or the frame number updated in step S512 described later.

Next, like the aforementioned step S410, the control unit 35 updates the frame number n for one of all in vivo images AI to be processed for display (step S512). Then, like the aforementioned step S411, the control unit 35 determines whether there is any temporary halt instruction of the image in the main display area 100 (step S513) and, if there is a temporary halt instruction (step S513, Yes), returns to step S502 to repeat step S502 and thereafter.

If, on the other hand, there is no temporary halt instruction (step S513, No), like the aforementioned step S412, the control unit 35 determines whether image display processing to display in the main display area 100 images contained in all in vivo images AI has terminated (step S514). If the control unit 35 determines that image display processing has not terminated (step S514, No), the control unit 35 returns to step S503 to repeat the processing procedure of step S503 and thereafter and, if the control unit 35 determines that image display processing has terminated (step S514, Yes), the control unit 35 terminates image display processing of images inside the subject 1.

Figure 16:
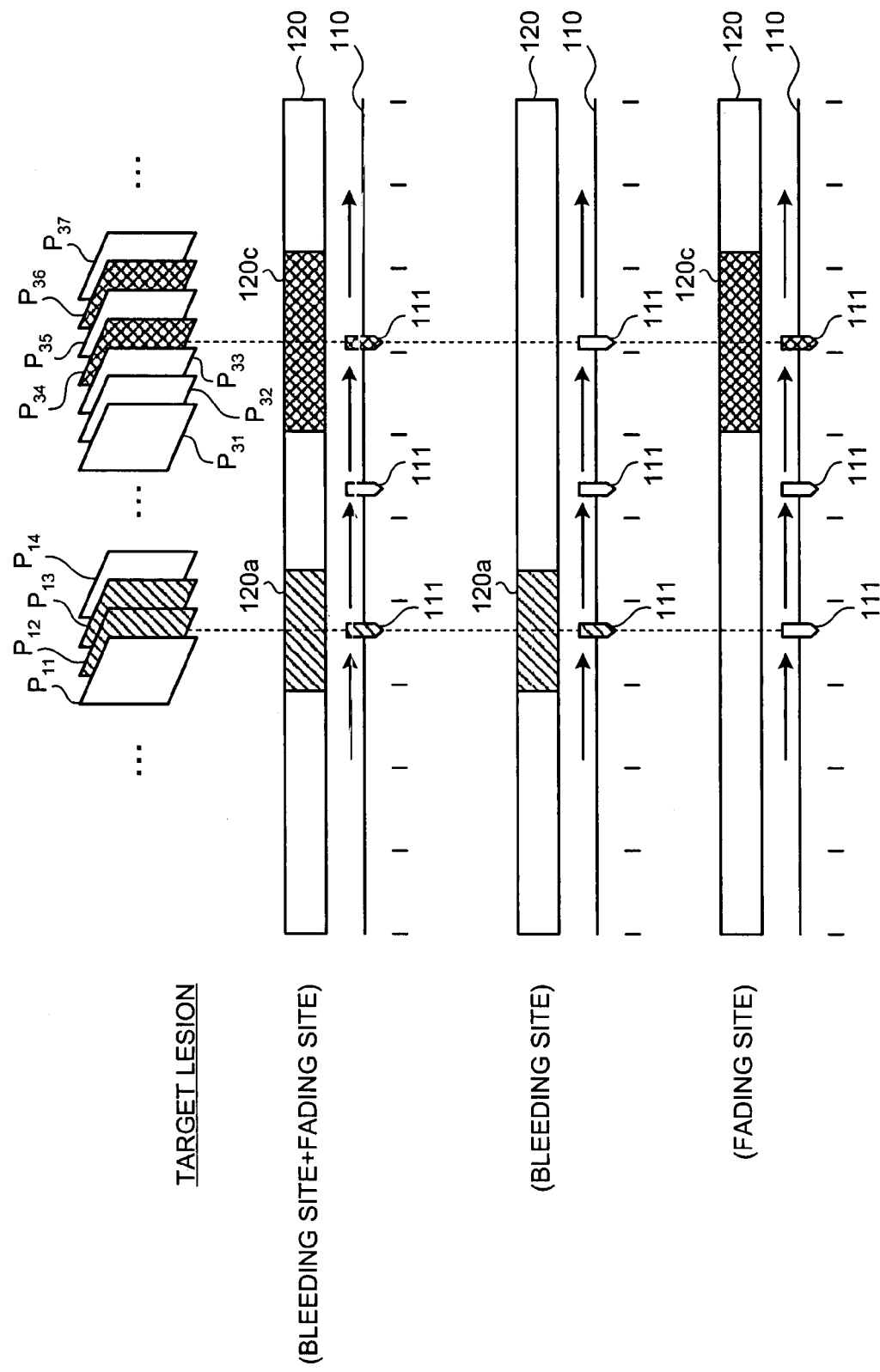
FIG. 16 is a schematic view illustrating an operation of the control unit displaying the lesion marks and slider lesion colors corresponding to target lesions.

Next, a case in which bleeding sites and fading images, which are an example of multiple kinds of lesion images, are displayed in the main display area 100 will be exemplified to concretely describe an operation of the control unit 35 that performs control to display the lesion marks and the lesion colors of the slider 111 corresponding to one or more lesions selected by the lesion selector 160, that is, one or more lesions (for example, at least one of the bleeding site and fading site) set by the target lesion setting unit 35c as target lesions. FIG. 16 is a schematic view illustrating an operation of the control unit 35 that displays the lesion marks and the lesion colors of the slider 111 corresponding to lesions set as target lesions.

First, an operation of the control unit 35 that performs control to display one or more lesion marks corresponding to one or lesions set as target lesions will concretely be described. Before making each image contained in all in vivo images AI to be displayed in the main display area 100, the control unit 35 causes the mark display area 120 to display the lesion marks corresponding to lesions set as target lesions. For example, like the aforementioned second embodiment, the control unit 35 detects the bleeding images $P_{12}$ and $P_{13}$ and fading images $P_{34}$ and $P_{36}$ contained in all in vivo images AI.

Here, if both the bleeding site and fading site are set as target lesions, as shown in FIG. 16, the control unit 35 causes the mark display area 120 to display the lesion mark 120a indicating the time positions of the bleeding images $P_{12}$ and $P_{13}$ containing a target lesion of bleeding site as a photographic object in the lesion color of bleeding (for example, red) and causes the mark display area 120 to display the lesion mark 120c indicating the time positions of the fading images $P_{34}$ and $P_{36}$ containing a target lesion of fading site as a photographic object in the lesion color of fading (for example, white).

If only the bleeding site of the bleeding site and fading site is set as a target lesion, as shown in FIG. 16, the control unit 35 causes the mark display area 120 to display the lesion mark 120a indicating the time positions of the bleeding images $P_{12}$ and $P_{13}$ containing a target lesion of bleeding site as a photographic object in the lesion color of bleeding. In contrast, the control unit 35 does not cause the mark display area 120 to display the lesion mark 120c indicating the time positions of the fading images $P_{34}$ and $P_{36}$ containing no such target lesion (bleeding site) as a photographic object.

If, on the other hand, only the fading site of the bleeding site and fading site is set as a target lesion, as shown in FIG. 16, the control unit 35 causes the mark display area 120 to display the lesion mark 120c indicating the time positions of the fading images $P_{34}$ and $P_{36}$ containing a target lesion of fading site as a photographic object in the lesion color of fading. In contrast, the control unit 35 does not cause the mark display area 120 to display the lesion mark 120a indicating the time positions of the bleeding images $P_{12}$ and $P_{13}$ containing no such target lesion (fading site) as a photographic object.

Next, an operation of the control unit 35 that performs control to display the slider 111 in the lesion color corresponding to the lesion set as a target lesion will concretely be described. Based on display instruction information input by the input unit 11, the control unit 35 performs control to display in the main display area 100 the image $P_n$ (n=1, 2, 3, . . . ) contained in the group of images inside the subject 1 and also causes the slider 111 to move along the time bar 110 to indicate the time position of the image currently displayed in the main display area 100.

Here, if both the bleeding site and fading site are set as target lesions, as already described, the control unit 35 has caused the mark display area 120 to display the bar-shaped lesion marks 120a and 120c. Meanwhile, the lesion mark 120a represents a partial image group containing the images $P_{11}$ and $P_{14}$ and the bleeding images $P_{12}$ and $P_{13}$ (that is, a partial image group of the frame number n=11 to 14) inside the subject 1. The lesion mark 120c represents a partial image group containing the fading images $P_{34}$ and $P_{36}$ and the images $P_{31}$, $P_{32}$, $P_{33}$, $P_{35}$, and $P_{37}$ (that is, a partial image group of the frame number n=31 to 37) inside the subject 1.

If the image currently displayed in the main display area 100 is a normal organ image, the control unit 35 performs control to display the slider 111 indicating the time position of the normal organ image in the default color. In contrast, if the image currently displayed in the main display area 100 is the bleeding image $P_{12}$ or $P_{13}$ while both the bleeding site and fading site are set as target lesions, the control unit 35 performs control to change the default color of the slider 111 positioned in the display range of the lesion mark 120a to the lesion color of bleeding. In this case, the control unit 35 changes the display color of the slider 111 indicating the time positions of the bleeding image $P_{12}$ or $P_{13}$ corresponding to such a target lesion to the lesion color of bleeding (for example, red), which is the same color as that of the lesion mark 120a.

If the image currently displayed in the main display area 100 is the fading image $P_{34}$ or $P_{36}$ while both the bleeding site and fading site are set as target lesions, the control unit 35 performs control to change the default color of the slider 111 positioned in the display range of the lesion mark 120c to the lesion color of fading. In this case, the control unit 35 changes the display color of the slider 111 indicating the time positions of the fading image $P_{34}$ or $P_{36}$ corresponding to such a target lesion to the lesion color of fading (for example, white), which is the same color as that of the lesion mark 120c.

If the image currently displayed in the main display area 100 is a normal organ image like $P_{11}$ and $P_{14}$, the control unit 35 sets the display color of the slider 111 to the default color even if the slider 111 is positioned within the display range of the lesion mark 120a. Similarly, if the image currently displayed in the main display area 100 is a normal organ image like $P_{31}$, $P_{32}$, $P_{33}$, $P_{35}$ and $P_{37}$, the control unit 35 sets the display color of the slider 111 to the default color even if the slider 111 is positioned within the display range of the lesion mark 120c.

If only the bleeding site of the bleeding site and fading site is set as a target lesion, as shown in FIG. 16, the control unit 35 has caused the mark display area 120 to display the bar-shaped lesion mark 120a and does not cause the mark display area 120 to display the lesion mark 120c. If the image currently displayed in the main display area 100 is a normal organ image, the control unit 35 performs control to display the slider 111 indicating the time position of the normal organ image in the default color regardless of the position on the time bar 110.

If the image currently displayed in the main display area 100 is the bleeding image $P_{12}$ or $P_{13}$ while only the bleeding site is set as a target lesion, just like when both the bleeding site and fading site are set as target lesions, the control unit 35 performs control to change the default color of the slider 111 positioned within the display range of the lesion mark 120a to the lesion color of bleeding. In contrast, since only the bleeding site, instead of the fading site, is set as a target lesion, the display color of the slider 111 indicating the time position of the fading image $P_{34}$ or $P_{36}$ is set to the default color even if the image currently displayed in the main display area 100 is the fading image $P_{34}$ or $P_{36}$. That is, when only the bleeding site is set as a target lesion, the control unit 35 displays only the slider 111 in a state of indicating the time position of a bleeding image containing a target lesion of bleeding site as a photographic object in the lesion color of bleeding and displays the slider 111 in other states in the default color.

If, on the other hand, only the fading site of the bleeding site and fading site is set as a target lesion, as shown in FIG. 16, the control unit 35 has caused the mark display area 120 to display the bar-shaped lesion mark 120c and does not cause the mark display area 120 to display the lesion mark 120a. If the image currently displayed in the main display area 100 is a normal organ image, the control unit 35 performs control to display the slider 111 indicating the time position of the normal organ image in the default color regardless of the position on the time bar 110.

If the image currently displayed in the main display area 100 is the fading image $P_{34}$ or $P_{36}$ while only the fading site is set as a target lesion, just like when both the bleeding site and fading site are set as target lesions, the control unit 35 performs control to change the default color of the slider 111 positioned within the display range of the lesion mark 120c to the lesion color of fading. In contrast, since only the fading site, instead of the bleeding site, is set as a target lesion, the display color of the slider 111 indicating the time position of the bleeding image $P_{12}$ or $P_{13}$ is set to the default color even if the image currently displayed in the main display area 100 is the bleeding image $P_{12}$ or $P_{13}$. That is, when only the fading site is set as a target lesion, the control unit 35 displays only the slider 111 in a state of indicating the time position of a fading image containing a target lesion of fading site as a photographic object in the lesion color of fading and displays the slider 111 in other states in the default color.

Through control of the display of lesion marks by the control unit 35, as described above, the mark display area 120 can display only lesion marks corresponding to desired lesions selected by the lesion selector 160. Thus, the time positions of lesion images in which desired lesions (for example, a bleeding site and fading site) are picked up can be indicated from among all in vivo images AI in which multiple kinds of lesion images are mixed. As a result, the time positions of desired lesion images to be observed can easily be confirmed without being confused by lesion marks indicating the time positions of other lesion images even if multiple kinds of lesion images are mixed in all in vivo images AI.

Also, through control of the display color of the slider 111 by the control unit 35, as described above, the slider 111 can display whether the image currently displayed in the main display area 100 is a lesion image via its display color without disturbing observation of the currently displayed image and also which of a bleeding image and fading image the lesion image is like the aforementioned second embodiment.

Further, since the slider 111 displays the lesion color corresponding to a lesion of a lesion image only when the lesion image indicating a desired lesion selected by the lesion selector 160 is displayed in the main display area 100, whether the image currently displayed in the main display area 100 is a desired lesion image to be observed can easily be indicated. As a result, that a desired lesion image to be observed is currently displayed in the main display area 100 can easily be indicated even if multiple kinds of lesion images are mixed in all in vivo images AI.

Therefore, a user such as a physician and nurse can observe the image currently displayed in the main display area 100 without being disturbed by change in display color of the slider 111 and also understand easily that, by visually confirming the lesion color of the slider 111, the currently displayed image is a desired lesion image to be observed and, in that case, the kind of lesion (a bleeding site or fading site) indicated by the lesion image. As a result, the user can easily search for and display desired lesion images to be observed from among all in vivo images AI successively displayed in the main display area 100 even if multiple kinds of lesion images are contained in all in vivo images AI and also easily identify the kind of lesion (a bleeding site or fading site) indicated by the lesion image, allowing efficient observation of the desired lesion images.

As has been described, in the third embodiment of the present invention, the image display device is configured in such ways that, in addition to the functions of the aforementioned second embodiment, one or more desired lesion images are selected from multiple kinds of lesions, lesions marks indicating time positions of lesion images in which the selected lesions (target lesions) are picked up are displayed and, if the image currently displayed in the main display area is one of lesion images of the target lesions, the display color of a slider indicating the time positions of lesion images of the target lesions is displayed in a lesion color corresponding to each of the target lesions. Thus, even if multiple kinds of lesion images are contained in a group of images inside a subject to be processed for display, the time positions of desired lesion images among the multiple kinds of lesion images can easily be displayed and whether the image displayed in the main display area is a desired lesion image can easily be determined. As a result, operation effects of the aforementioned second embodiment can be gained and also desired lesion images to be observed can be selected from among multiple kinds of lesion images contained in a group of images inside a subject so that an image display device that allows easy observation of a selected desired lesion image can be realized.

Fourth Embodiment

Next, a fourth embodiment of the present invention will be described. In the aforementioned third embodiment, desired lesions are selected from multiple kinds of lesions, and lesion marks and lesion colors of the slider 111 corresponding to the selected desired lesions are displayed. In the fourth embodiment, further a display mode of the image for the main display area 100 is selected so that all in vivo images AI is displayed in the main display area 100 in the selected display mode.

Figure 17:
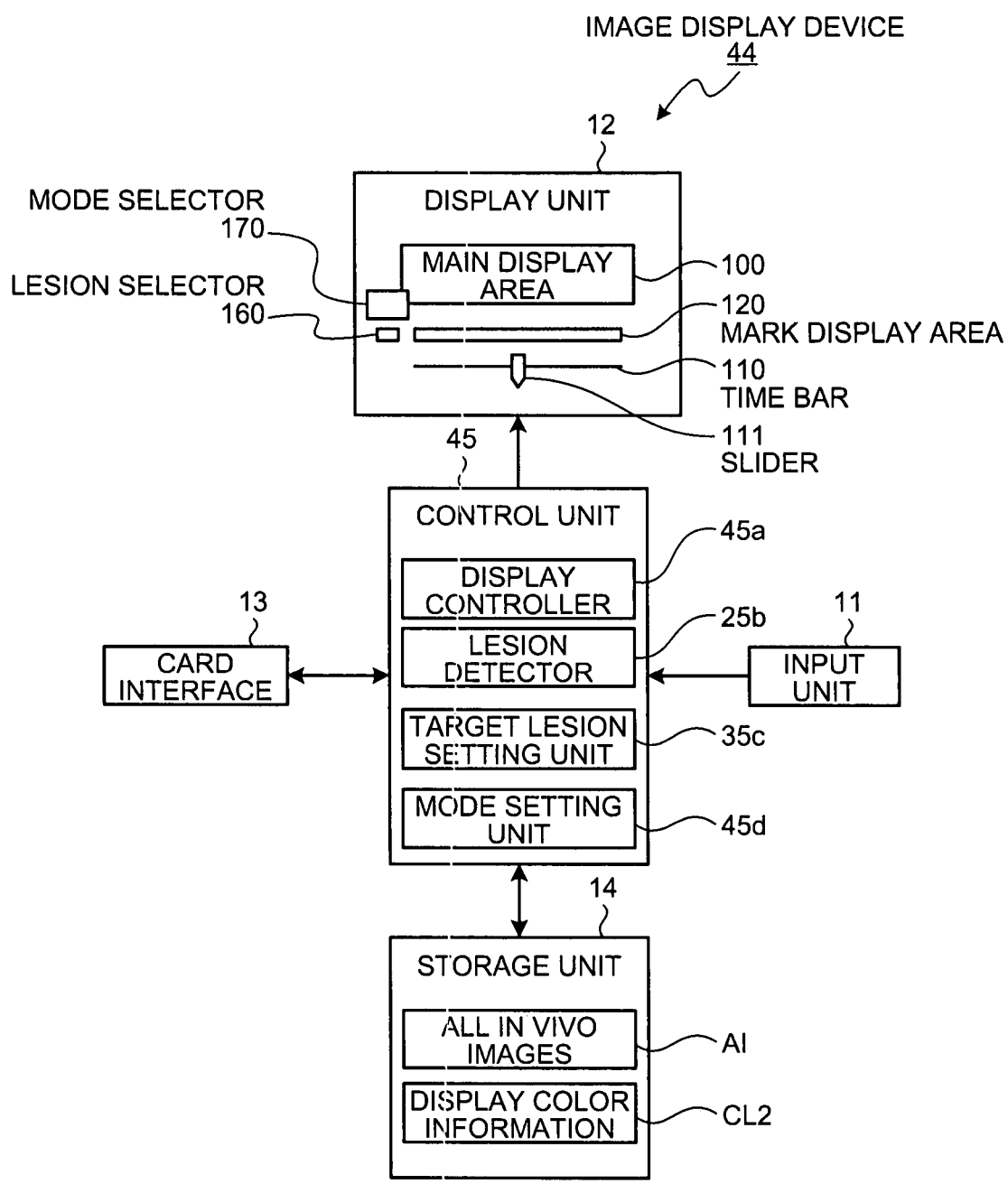
FIG. 17 is a block diagram schematically showing a configuration example of an image display device according to a fourth embodiment of the present invention.

FIG. 17 is a block diagram schematically showing a configuration example of an image display device according to the fourth embodiment of the present invention. As shown in FIG. 17, an image display device 44 according to the fourth embodiment has a control unit 45 instead of the control unit 35 of the image display device 34 according to the aforementioned third embodiment. In the image display device 44, the display unit 12 further displays a mode selector 170, which is a GUI for selecting the display mode of the image for the main display area 100. An in-vivo information acquiring system according to the fourth embodiment of the present invention has the image display device 44 instead of the image display device 34 in the in-vivo information acquiring system according to the aforementioned third embodiment. Other components are the same as those of the third embodiment and the same numeral is attached to the same component.

Approximately similarly to the control unit 35 of the image display device 34 according to the aforementioned third embodiment, the control unit 45 controls each of the input unit 11, display unit 12, card interface 13, and storage unit 14, and also controls input/output of information between such components. The control unit 45 also has a target lesion setting function similar to that of the aforementioned control unit 35 and a display control function of lesion marks and display color of the slider 111 corresponding to the target lesions. In addition to the functions described above, the control unit 45 sets the display mode of images selected by the mode selector 170 displayed in the display unit 12 and performs image display control of the set display mode. The control unit 45 described above has the aforementioned lesion detector 25b and target lesion setting unit 35c and also has a display controller 45a instead of the display controller 35a of the control unit 25 in the third embodiment. Further, the control unit 45 has a mode setting unit 45d that sets the display mode selected by the mode selector 170 as the display mode of images for the main display area 100.

Like the aforementioned display controller 35a of the control unit 35, the display controller 45a has the display control function of lesion marks of the target lesions and that of the display color of the slider 111 of the target lesion. Further, the display controller 45a performs image display control based on the display mode of images set by the mode setting unit 45d. The display mode of images set by the mode setting unit 45d includes a normal play mode in which all in vivo images AI to be processed for display is displayed and a lesion play mode in which lesion images corresponding to the target lesions among all in vivo images AI are displayed. If the normal play mode is set by the mode setting unit 45d, the display controller 45a performs control, based on the normal play mode, to display in the main display area 100 each image contained in all in vivo images AI. If, on the other hand, the lesion play mode is set by the mode setting unit 45d, the display controller 45a performs control, based on the lesion play mode, to extract lesion images corresponding to the target lesions from multiple kinds of lesion images contained in all in vivo images AI and display the extracted lesion images in the main display area 100.

The mode setting unit 45d sets the display mode selected by the mode selector 170 displayed in the display unit 12 as the display mode of images for the main display area 100. In this case, the mode setting unit 45d sets either the aforementioned normal display mode or lesion display mode as the display mode of images for the main display area 100.

Figure 18:
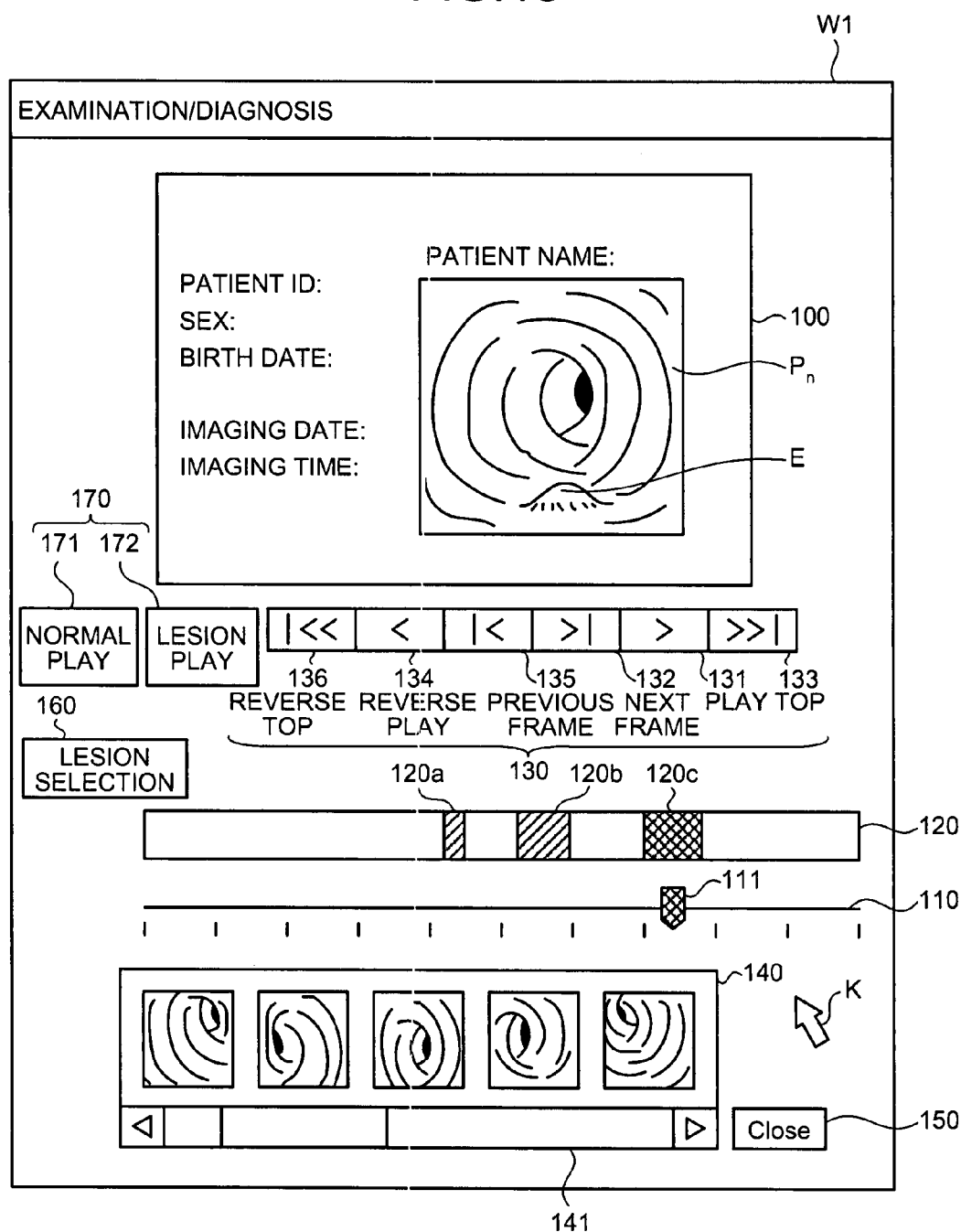
FIG. 18 is a schematic view exemplifying the display mode of the control unit further displaying a mode selector, which is a GUI for selecting a display mode of images.

Next, the display mode of the display unit 12 will be concretely exemplified to describe an operation of the display controller 45a to control GUI displayed in the display unit 12 and a display operation of the display unit 12. FIG. 18 is a schematic view exemplifying the display mode of the display unit 12 further displaying the mode selector 170, which is a GUI for selecting a display mode of images for the main display area 100.

As shown in FIG. 18, the mode selector 170, which is a GUI for selecting either the normal play mode or lesion play mode, is additionally formed in the window W1 displayed in the display unit 12 of the image display device 44. If the normal play mode is selected by the mode selector 170, each image contained in all in vivo images AI is displayed in the main display area 100 of the window W1 and, if the lesion play mode is selected by the mode selector 170, lesion images corresponding to the target lesions among multiple kinds of lesion images contained in all in vivo images AI are displayed. Other display modes of the window W1 are the same as those of the aforementioned third embodiment.

The mode selector 170 has a normal play selector 171, which is a GUI for selecting the normal play mode, and a lesion play selector 172, which is a GUI for selecting the lesion play mode. The normal play selector 171 and lesion play selector 172 are displayed, for example, as push buttons in the display unit 12.

The normal play selector 171 selects the normal play mode through a click operation or the like using the input unit 11. In this case, the input unit 11 inputs selection information that the normal play mode will be selected into the control unit 45. Based on the selection information of the normal play mode input by the input unit 11, the aforementioned mode setting unit 45d sets the display mode of images for the main display area 100 to the normal play mode.

The lesion play selector 172 selects the lesion play mode through a click operation or the like using the input unit 11. In this case, the input unit 11 inputs selection information that the lesion play mode will be selected into the control unit 45. Based on the selection information of the lesion play mode input by the input unit 11, the aforementioned mode setting unit 45d sets the display mode of images for the main display area 100 to the lesion play mode.

Figure 19:
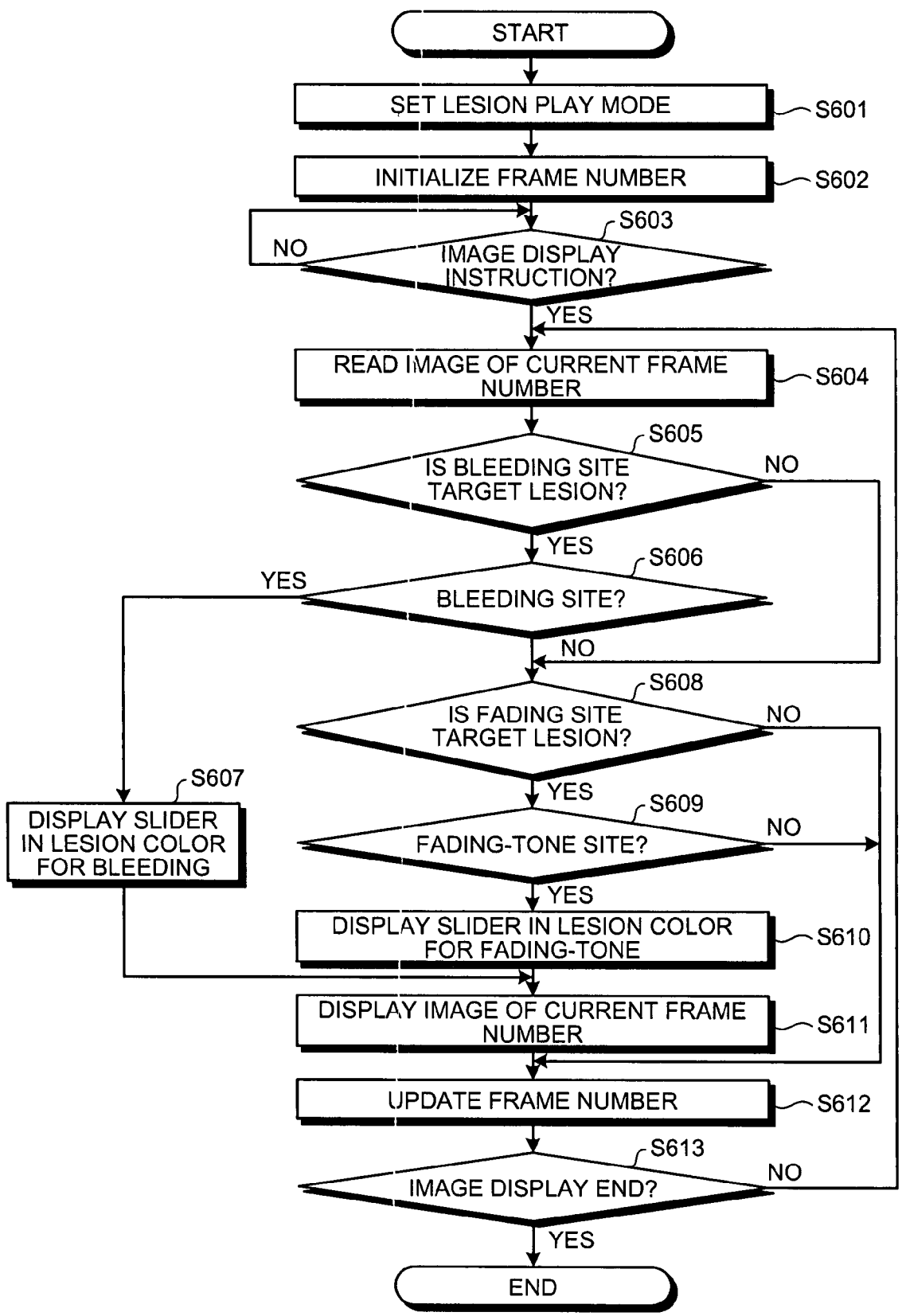
FIG. 19 is a flow chart illustrating the processing procedure of the control unit performing control to display a lesion image inside a subject in a main display area based on a lesion play mode.

Next, operations of the control unit 45 to perform control to make all in vivo images AI containing multiple kinds of lesion images (for example, bleeding images and fading images) the group of images to be processed for display and, based on the lesion play mode, to display lesion images in all in vivo images AI in the main display area 100 and also to control the display color of the slider 111 indicating the time position of the image currently displayed in the main display area 100. FIG. 19 is a flow chart illustrating the processing procedure of the control unit 45 performing control to display lesion images inside the subject 1 in the main display area 100 based on the lesion play mode.

If the lesion play mode is selected by the mode selector 170 (more specifically, the lesion play selector 172), the control unit 45 performs control, based on the lesion play mode, to display in the main display area 100 lesion images corresponding to the target lesions among multiple kinds of lesion images in all in vivo images AI and controls the display color of the slider 111 indicating the time position of the lesion image currently displayed in the main display area 100. In this case, the control unit 45 performs control to display the slider 111 indicating the time position of the lesion image in the lesion color corresponding to the target lesion.

More specifically, as shown in FIG. 19, the control unit 45 first sets the lesion play mode selected by the mode selector 170 (step S601). In this case, based on the selection information of the lesion play mode input by the input unit 11, the mode setting unit 45d sets the display mode of images for the main display area 100 to the lesion play mode.

Next, the control unit 45 performs a processing procedure similar to that of the aforementioned steps S501 to S503 (See FIG. 15), initializes the frame number n of all in vivo images AI, determines whether there is any image display instruction, and, if there is an image display instruction, reads the image of the current frame number in all in vivo images AI (steps S602 to S604).

Next, the control unit 45 determines the lesion selected by the aforementioned lesion selector 160 (that is, a target lesion). In this case, like the aforementioned step S504 for example, the control unit 45 determines whether the bleeding site is a target lesion (step S605). If the control unit 45 determines in this step S605 that the bleeding site is a target lesion (step S605, Yes), the control unit 45 determines whether the image of the current frame number read in step S604 is a bleeding image (step S606). In this case, like the aforementioned step S505, if a lesion flag of bleeding is attached to the image of the current frame number, the display controller 45a determines that the image of the current frame number is a bleeding image and, if no lesion flag of bleeding is attached to the image of the current frame number, the display controller 45a determines that the image of the current frame number is not a bleeding image.

Thus, if the control unit 45 determines that the image of the current frame number is a bleeding image while the bleeding site is set as a target lesion (step S606, Yes), like the aforementioned step S506, the control unit 45 performs control to display the slider 111 indicating the time position of the image of the current frame number, that is, the bleeding image in the lesion color of bleeding (step S607). In this case, the display controller 45a causes the slider 111 to move to the time position on the time bar 110 corresponding to the image of the current frame number, which is a bleeding image, and performs control to display the slider 111 indicating the time position of the image of the current frame number, which is the aforementioned bleeding image, in the lesion color of bleeding (for example, red).

If, on the other hand, the control unit 45 determines in this step S605 that the bleeding site is not a target region (step S605, No), like the aforementioned step S507, the control unit 45 determines whether the fading site is a target lesion (step S608). If the control unit 45 determines in this step S608 that the fading site is a target lesion (step S608, Yes), the control unit 45 determines whether the image of the current frame number read in step S604 is a fading image (step S609). In this case, like the aforementioned step S508, if a lesion flag of fading is attached to the image of the current frame number, the display controller 45a determines that the image of the current frame number is a fading image and, if no lesion flag of fading is attached to the image of the current frame number, the display controller 45a determines that the image of the current frame number is not a fading image.

Thus, if the control unit 45 determines that the image of the current frame number is a fading image while the fading site is set as a target lesion (step S609, Yes), like the aforementioned step S506, the control unit 45 performs control to display the slider 111 indicating the time position of the image of the current frame number, that is, the fading image in the lesion color of fading (step S610). In this case, the display controller 45a causes the slider 111 to move to the time position on the time bar 110 corresponding to the image of the current frame number, which is a fading image, and performs control to display the slider 111 indicating the time position of the image of the current frame number, which is the aforementioned fading image, in the lesion color of fading (for example, white).

Subsequently, the control unit 45 performs control to display the image of the current frame number, which is a lesion image corresponds to a target lesion, in the main display area 100 (step S611). More specifically, if, while both the bleeding site and fading site are set as target lesions, the image of the current frame number is a bleeding image, the bleeding image of the current frame number is made to be displayed in the main display area 100 by the display controller 45a and, if the image of the current frame number is a fading image, the fading image of the current frame number is made to be displayed in the main display area 100. If, on the other hand, while only the bleeding site of the bleeding site and fading site is set as a target lesion, the image of the current frame number is a bleeding image, the bleeding image of the current frame number is made to be displayed in the main display area 100 by the display controller 45a. If, while only the fading site of the bleeding site and fading site is set as a target lesion, the image of the current frame number is a fading image, the fading image of the current frame number is made to be displayed in the main display area 100 by the display controller 45a.

Thus, when a lesion image (a bleeding image or fading image) corresponding to a target lesion is displayed in the main display area 100, the slider 111 displays the lesion color corresponding to the lesion (that is, the target lesion) indicated by the lesion image in the main display area 100. As described above, the lesion color of the slider 111 is the same as the color of the lesion mark indicating the time position of the lesion image in the main display area 100.

Meanwhile, the frame number of the lesion image displayed in the main display area 100 (that is, the current frame number) in step S611 is the frame number initialized in the aforementioned step S602 or the frame number updated in step S612 described later.

Next, like the aforementioned step S512, the control unit 45 updates the frame number n for one of all in vivo images AI to be processed for display (step S612). Then, like the aforementioned step S514, the control unit 45 determines whether image display processing of the lesion play mode to display in the main display area 100 lesion images contained in all in vivo images AI has terminated (step S613).

If the control unit 45 determines that image display processing of the lesion play mode has not terminated (step S613, No), the control unit 45 returns to step S604 to repeat the processing procedure of step S604 and thereafter. If, on the other hand, the control unit 45 determines that image display processing of the lesion play mode has terminated (step S613, Yes), the control unit 45 terminates image display processing of the lesion play mode.

If, on the other hand, the control unit 45 determines that the image of the current frame number is not a bleeding image in step the aforementioned S606 (step S606, No), the control unit 45 proceeds to step S608 to repeat the processing procedure of step S608 and thereafter. If the control unit 45 determines that the fading site is not a target lesion in the aforementioned step S608 (step S608, No) or the image of the current frame number is not a fading image in the aforementioned step S609 (step S609, No), the control unit 45 proceeds to step S612 to repeat the processing procedure of step S612 and thereafter.

That is, if neither bleeding site nor fading site is a target lesion, the control unit 45 terminates image display process of the lesion play mode without displaying all in vivo images AI. If both the bleeding site and fading site are set as target lesions and the image of the current frame number is neither bleeding image nor fading image (for example, a normal organ image), the control unit 45 skips the aforementioned step S611 not to allow the image of the current frame number to be displayed in the main display area 100. Further, if only the bleeding site of the bleeding site and fading site is a target lesion and the image of the current frame number is not a bleeding image (for example, a normal organ image or fading image), the control unit 45 skips the aforementioned step S611 not to allow the image of the current frame number to be displayed in the main display area 100. Also, if only the fading site of the bleeding site and fading site is a target lesion and the image of the current frame number is not a fading site (for example, a normal organ image or bleeding image), the control unit 45 skips the aforementioned step S611 not to allow the image of the current frame number to be displayed in the main display area 100.

By repeating the processing procedure of the aforementioned steps S601 to S613, the control unit 45 described above can play lesion images of the target lesions among multiple kinds of lesion images contained in all in vivo images AI like pseudo motion pictures in the main display area 100.

If the normal play mode is selected by the mode selector 170 (more specifically, the normal play selector 171), the control unit 45 described above sets the display mode of images for the main display area 100 to the normal play mode, as described above, and, based on the set normal play mode, performs control to display in the main display area 100 each image contained in all in vivo images AI. In this case, the control unit 12 repeats the processing procedure of the aforementioned steps S501 to S514 to perform image display processing of the normal play mode and also to control the display color of the slider 111.

Next, all in vivo images AI containing bleeding sites and fading images, which are an example of multiple kinds of lesion images will be exemplified to describe an operation of the control unit 45 that performs control, based on the lesion play mode, to display lesion images in all in vivo images AI in the main display area 100. FIG. 20 is a schematic view illustrating an operation of the control unit 45 displaying in the main display area 100 a lesion image containing the target lesion as a photographic object from among a plurality of lesion images.

As shown in FIG. 20, the control unit 45 detects, for example, the bleeding images $P_{12}$ and $P_{13}$ and the fading images $P_{34}$ and $P_{36}$ contained in all in vivo images AI. If the lesion play mode is selected by the mode selector 170, the control unit 45 performs control to extract lesion images containing any lesion selected by the lesion selector 160 as a photographic object from all in vivo images AI and to successively display the extracted lesion images in a time series.

More specifically, if both the bleeding site and fading site are set as target lesions, as shown in FIG. 20, the control unit 45 performs control to extract the bleeding images $P_{12}$ and $P_{13}$ containing a target lesion of bleeding site as a photographic object and the fading images $P_{34}$ and $P_{36}$ containing a target lesion of fading site as a photographic object from all in vivo images AI and to successively display the extracted bleeding images $P_{12}$ and $P_{13}$ and fading images $P_{34}$ and $P_{36}$ in the main display area 100 in a time series. Through control of the control unit 45, the bleeding images $P_{12}$ and $P_{13}$ and fading images $P_{34}$ and $P_{36}$ corresponding to the target lesions are displayed successively in the main display area 100 like pseudo motion pictures.

The control unit 45 causes the slider 111 to move along the time bar 110 to successively indicate the time position of the lesion images (the bleeding images $P_{12}$ and $P_{13}$ and fading images $P_{34}$ and $P_{36}$) successively displayed in the main display area 100 and also controls the lesion color of the slider 111. More specifically, when one of the bleeding images $P_{12}$ and $P_{13}$ is displayed in the main display area 100, the control unit 45 changes the display color of the slider 111 to the lesion color of bleeding (for example, red) and when one of the fading images $P_{34}$ and $P_{36}$ is displayed in the main display area 100, the control unit 45 changes the display color of the slider 111 to the lesion color of fading (for example, white).

If, on the other hand, only the bleeding site of the bleeding site and fading site is set as a target lesion, as shown in FIG. 20, the control unit 45 performs control to extract the bleeding images $P_{12}$ and $P_{13}$ containing a target lesion of bleeding site as a photographic object and to successively display the extracted bleeding images $P_{12}$ and $P_{13}$ in the main display area 100 in a time series. Through control of the control unit 45, the bleeding images $P_{12}$ and $P_{13}$ corresponding to the target lesion are displayed successively in the main display area 100 like pseudo motion pictures.

The control unit 45 causes the slider 111 to move along the time bar 110 to successively indicate the time position of the bleeding images $P_{12}$ and $P_{13}$ successively displayed in the main display area 100 and also controls the lesion color of the slider 111. More specifically, when one of the bleeding images $P_{12}$ and $P_{13}$ is displayed in the main display area 100, the control unit 45 changes the display color of the slider 111 to the lesion color of bleeding.

If only the fading site of the bleeding site and fading site is set as a target lesion, as shown in FIG. 20, the control unit 45 performs control to extract the fading images $P_{34}$ and $P_{36}$ containing a target lesion of fading site as a photographic object and to successively display the extracted fading images $P_{34}$ and $P_{36}$ in the main display area 100 in a time series. Through control of the control unit 45, the fading images $P_{34}$ and $P_{36}$ corresponding to the target lesion are displayed successively in the main display area 100 like pseudo motion pictures.

The control unit 45 causes the slider 111 to move along the time bar 110 to successively indicate the time position of the fading images $P_{34}$ and $P_{36}$ successively displayed in the main display area 100 and also controls the lesion color of the slider 111. More specifically, when one of the fading images $P_{34}$ and $P_{36}$ is displayed in the main display area 100, the control unit 45 changes the display color of the slider 111 to the lesion color of fading.

Thus, through control of the display of lesion images of the target lesions by the control unit 45, the main display area 100 can alternatively display a lesion image containing a desired lesion selected by the lesion selector 160 as a photographic object. Thus, one or more lesion images in which a desired lesion (for example, a bleeding site and fading site) is picked up from among all in vivo images AI in which multiple kinds of lesion images are mixed can easily be displayed. As a result, even if multiple kinds of lesion images are mixed in all in vivo images AI, desired lesion images to be observed can be displayed in a time series like pseudo motion pictures.

Therefore, a user such as a physician and nurse can easily observe the desired lesion image currently displayed in the main display area 100 without being disturbed by change in display color of the slider 111 and, by visually confirming the lesion color of the slider 111, can easily determine the kind of each lesion (such as the bleeding site and fading site) indicated by each of multiple kinds of lesion images successively displayed in the main display area 100. As a result, the user can easily display desired lesion images to be observed from among all in vivo images AI in the main display area 100 in a short time even if multiple kinds of lesion images are contained in all in vivo images AI and also easily identify the kind of lesion indicated by each of such lesion images, allowing efficient observation of the desired lesion images.

As has been described, in the fourth embodiment of the present invention, the image display device is configured in such ways that, in addition to the functions of the aforementioned third embodiment, the normal play mode in which each image contained in a group of images inside a subject is displayed in a main display area and a lesion play mode in which lesion images contained in the group of images inside the subject are displayed in the main display area can alternatively be selected and, if the lesion play mode is selected, lesion images of desired lesions (target lesions) selected from multiple kinds of lesions are extracted from the group of images inside the subject and the extracted lesion images of the target lesions are successively displayed in the main display area in a time series. Thus, even if multiple kinds of lesion images are contained in the group of images inside the subject to be processed for display, a desired lesion image can alternatively be displayed from among the multiple kinds of lesion images. As a result, operation effects of the aforementioned third embodiment can be gained and also a desired lesion image can be displayed from among multiple kinds of lesion images contained in a group of images inside a subject in a short time so that an image display device that allows more efficient observation of a desired lesion image can be realized.

Fifth Embodiment

Figure 21:
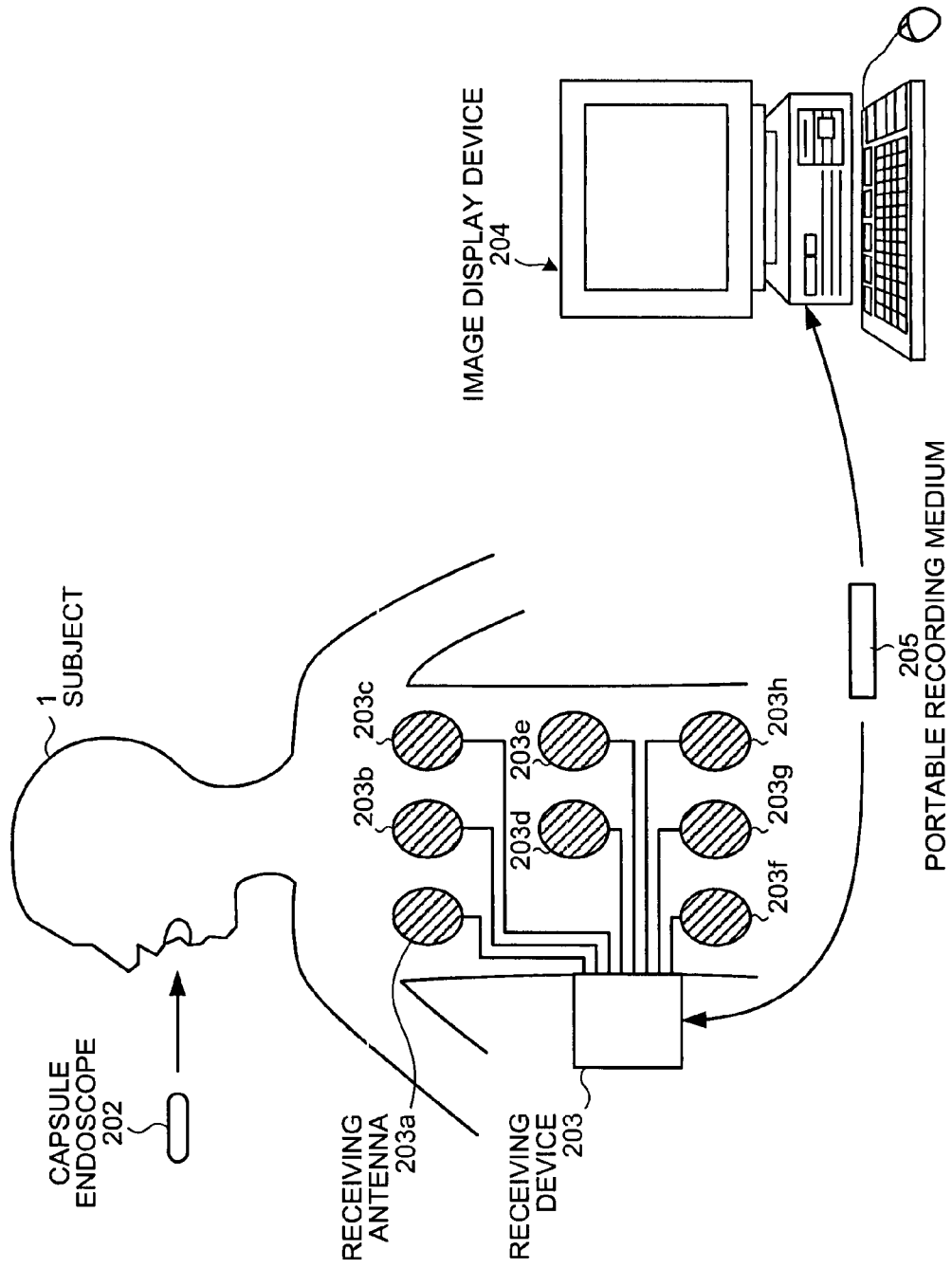
FIG. 21 is a schematic view exemplifying a configuration example of an in-vivo information acquiring system having an image display device according to a fifth embodiment of the present invention.

Next, a fifth embodiment of the present invention will be described. FIG. 21 is a schematic view exemplifying a configuration example of an in-vivo information acquiring system having an image display device according to the fifth embodiment of the present invention. As shown in FIG. 21, the in-vivo information acquiring system according to the fifth embodiment of the present invention comprises a capsule endoscope 202 for picking up images inside the subject 1, a receiving device 203 for receiving images inside the subject 1 picked up by the capsule endoscope 202, an image display device 204 for displaying an image inside the subject 1 received by the receiving device 203, and a portable recording medium 205 for exchanging data between the receiving device 203 and image display device 204.

The capsule endoscope 202 is used to pick up images inside a subject (more specifically, images inside organs). The capsule endoscope 202 has an imaging function, after being introduced into the subject 1, to successively pick up images inside the subject 1 in a time series and a radio communication function to transmit all in vivo images AI to the external receiving device 203 by radio. More specifically, after being swallowed through a month of the subject 1, the capsule endoscope 202 moves through organs of the subject 1 due to peristaltic movement or the like. At the same time, the capsule endoscope 202 sequentially picks up images inside the subject 1 at predetermined intervals, for example, of 0.5 seconds and sequentially transmits radio signals including images picked up inside the subject 1 to the receiving device 203.

The receiving device 203 has a plurality of receiving antennas 203a to 203h, for example, spread out over a body surface of the subject 1 to receive radio signals from the capsule endoscope 202 via at least one of the plurality of receiving antennas 203a to 203h. Then, the receiving device 203 acquires all in vivo images AI based on radio signals received from the capsule endoscope 202. The portable recording medium 205 is also detachably inserted into the receiving device 203 to store the group of images inside the subject 1 picked up by the capsule endoscope 202. In this case, the receiving device 203 stores in the portable recording medium 205 time information showing an imaging time or receiving time of each image contained in the group of images inside the subject 1 by associating the time information with each image in the group of images.

The receiving antennas 203a to 203h are realized, for example, by using a loop antenna and connected to the aforementioned receiving device 203. As shown in FIG. 21, the receiving antennas 203a to 203h are spread out at predetermined locations on the body surface of the subject 1, for example, locations corresponding to a passage route (that is, the digestive tract) of the capsule endoscope 202 inside the subject 1. The receiving antennas 203a to 203h described above capture radio signals from the capsule endoscope 202 introduced into organs of the subject 1 and transmit the captured radio signals to the receiving device 203. Meanwhile, the receiving antennas 203a to 203h may also be spread out over a jacket to be worn by the subject 1. In this case, the receiving antennas 203a to 203h are spread out at predetermined locations on the body surface of the subject 1 corresponding to the passage route of the capsule endoscope 202 inside the subject 1 when the subject 1 wears the jacket. At least one such antenna needs to be arranged for the subject 1 and its number is not particularly limited to 8.

The portable recording medium 205 is a recording medium that can be carried such as CompactFlash (registered trademark). The portable recording medium 205 has a structure so that the portable recording medium 205 can be inserted/detached into/from the receiving device 203 and image display device 204 and, when inserted, data can be output and recorded. More specifically, when inserted in the receiving device 203, the portable recording medium 205 sequentially stores various kinds of data such as groups of images inside the subject 1 received by the receiving device 203 and time information of each image. When inserted in the image display device 204, on the other hand, the portable recording medium 205 outputs stored data such as groups of images inside the subject 1 and time information of each image to the image display device 204. In this case, data stored in the portable recording medium 205 is captured by the image display device 204. In this way, the portable recording medium 205 exchanges data between the receiving device 203 and image display device 204. Also, patient information or the like about the subject 1 into which the capsule endoscope 202 is introduced is written into the portable recording medium 205 by the image display device 204.

The image display device 204 is used to display images inside the subject 1 picked up by the capsule endoscope 202. More specifically, the image display device 204 has a structure like a workstation so that various kinds of data such as groups of images inside the subject 1 picked up by the capsule endoscope 202 are acquired by capturing the stored data in the aforementioned portable recording medium 205 to display each image contained in the groups of images inside the subject 1. The image display device 204 has a processing function to enable a user such as a physician or nurse to diagnose the subject 1 by observing (examining) images inside the subject 1. In this case, the user causes the image display device 204 to successively display images inside the subject 1 to observe (examine) in-vivo regions such as esophagus, stomach, small intestine, and large intestine before diagnosing the subject 1 based on the observation (examination).

Figure 22:
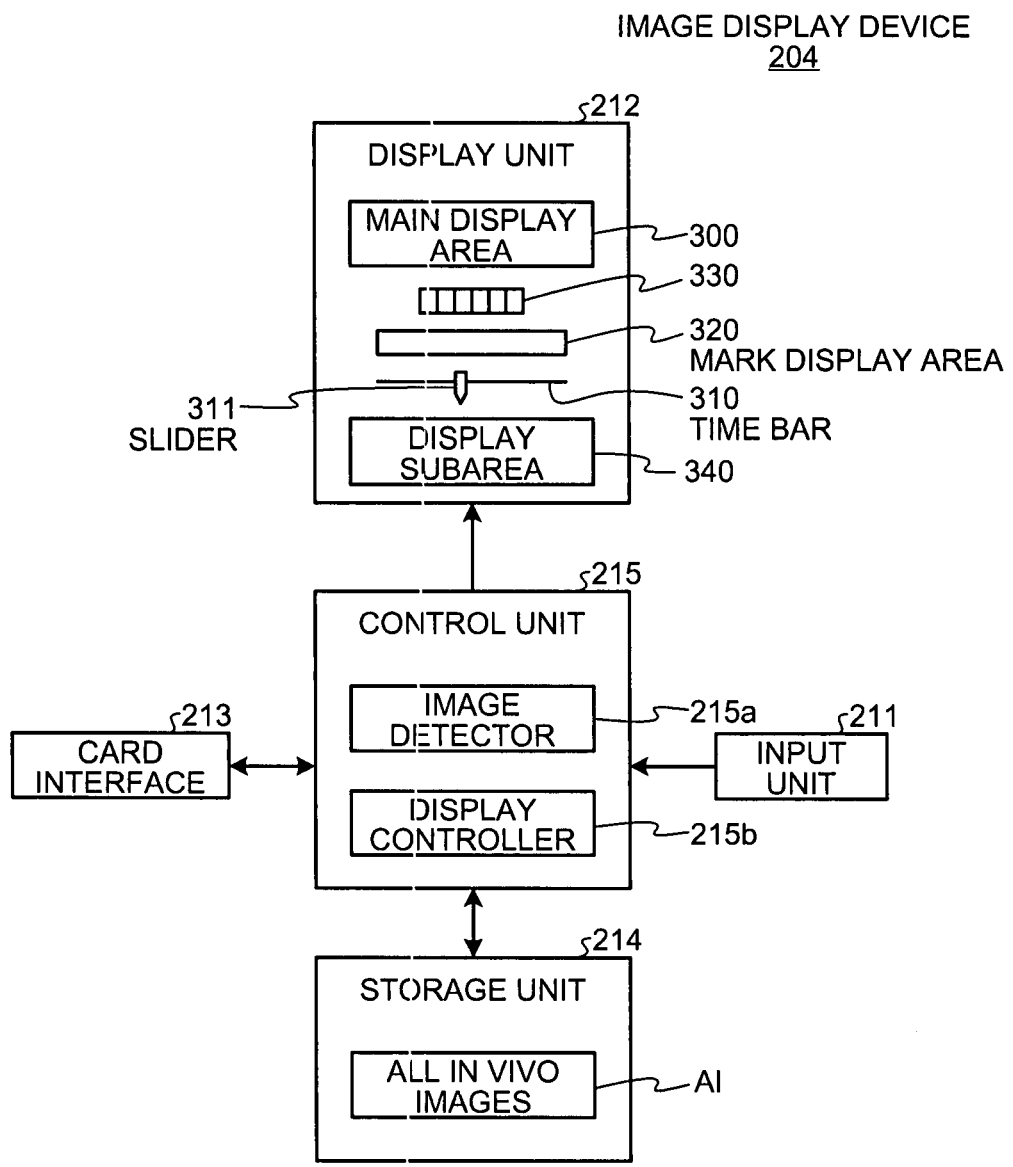
FIG. 22 is a block diagram schematically showing a configuration example of the image display device according to the fifth embodiment of the present invention.

Next, the configuration of the image display device 204 according to the fifth embodiment of the present invention will be described. FIG. 22 is a block diagram schematically showing a configuration example of the image display device 204 according to the fifth embodiment of the present invention. As shown in FIG. 22, the image display device 204 according to the fifth embodiment comprises an input unit 211 for inputting various kinds of information, a display unit 212 for displaying images inside the subject 1, GUI (Graphical User Interface) and the like in a screen, and a card interface (I/F) 213 for reading stored data (groups of images inside the subject 1 and the like) in the portable recording medium 205. The image display device 204 also comprises a storage unit 214 for storing various kinds of data such as groups of images of the subject 1 and a control unit 215 for controlling each component of the image display device 204.

The input unit 211 is realized using an input device such as a keyboard and mouse and inputs various kinds of information into the control unit 215 through an input operation by a user. For example, the input unit 211 inputs various kinds of instruction information giving instructions to the control unit 215 and patient information about the subject 1 into the control unit 215. Patient information input by the input unit 211 includes, for example, a patient name, sex, birth date, and patient ID of the subject 1.

The display unit 212 is realized using a display monitor that can display images such as a CRT display monitor and liquid crystal display monitor and displays various kinds of information instructed by the control unit 215 to display. More specifically, the display unit 212 displays various kinds of information used for observation (examination) of the subject 1 such as all in vivo images AI picked up by the capsule endoscope 202. The display unit 212 also displays various kinds of GUI for observing such all in vivo images AI. The display unit 212 described above comprises a main display area 300 for displaying each image contained in the group of images inside the subject 1, a time bar 310 showing an overall time position of each image contained in all in vivo images AI, a slider 311 showing the time position of the image (currently displayed image) inside the subject 1 currently displayed in the main display area 300, and a mark display area 320 for displaying a lesion mark showing the time position of a lesion image contained in the group of images inside the subject 1. Further, the display unit 212 comprises a display operation icon group 330 for performing various kinds of display operations when displaying an image inside the subject 1 in the main display area 300 and a display sub-area 340 for additionally displaying desired images selected from the group of images inside the subject 1 displayed in the main display area 300.

The aforementioned portable recording medium 205 is detachably inserted into the card interface 213, which reads stored data in the portable recording medium 205 and transmits the obtained stored data to the control unit 215. The card interface 213 also writes information instructed by the control unit 215, for example, patient information of the subject 1, into the inserted portable recording medium 205.

The storage unit 214 is realized using a large-capacity recording medium such as RAM, EEPROM, and hard disk and stores various kinds of data instructed to write by the control unit 215 and transmits stored data instructed to read by the control unit 215 to the control unit 215. The storage unit 214 described above stores all in vivo images AI picked up by the capsule endoscope 202, time information of each image in all in vivo images AI, and patient information of the subject 1. In this case, time information of each image stored in the storage unit 214 is attached to each piece of image data in all in vivo images AI.

The control unit 215 controls each component of the image display device 204. More specifically, the control unit 215 controls each of the input unit 211, display unit 212, card interface 213, and storage unit 214, and also controls input/output of information between such components. The control unit 215 described above acquires all in vivo images AI and time information associated with each image in all in vivo images AI from the portable recording medium 205 inserted in the card interface 213. The control unit 215 stores all in vivo images AI and time information after associating the time information with each image in the storage unit 214. Based on instruction information input by the input unit 211, the control unit 215 causes the display unit 212 to display in the main display area 300 each image contained in the group of images inside the subject 1.

The control unit 215 described above has an image detector 215a and a display controller 215b. The image detector 215a detects one or more lesion images contained in all in vivo images AI. More specifically, the image detector 215a detects color information of an image to be processed contained in all in vivo images AI and, based on the detected color information of the image, determines whether the image to be processed is a lesion image. If the image detector 215a detects that the image to be processed is a lesion image, the image detector 215a attaches a sign (lesion flag) indicating a lesion image to the image to be processed (that is, the lesion image). In this way, the image detector 215a detects any lesion image contained in all in vivo images AI. Such a lesion image with the attached lesion flag is stored in the storage unit 214 as part of all in vivo images AI. The image detector 215a performs detection processing of lesion images for all images in all in vivo images AI. Color information of images detected by the image detector 215a includes, for example, the average color of an image and values of color elements (R value, G, value, B value) of red (R), green (G), and blue (B) forming an image.

The display controller 215b performs control to display each image contained in all in vivo images AI stored in the storage unit 214 in the main display area 300 of the display unit 212. If, in this case, any lesion image is contained in all in vivo images AI, the display controller 215b performs control to display such a lesion image inside the subject 1 in the main display area 300 of the display unit 212. The display controller 215b also performs control to additionally display in the display sub-area 340 of the display unit 212 desired images selected from all in vivo images AI displayed in the main display area 300. In this case, reduced images (for example, thumbnail images) obtained by reducing the selected desired images in size are made to be displayed in the display sub-area 340 by the display controller 215b.

Also, the display controller 215b performs control to display lesion marks indicating the time positions of one or more lesion images contained in all in vivo images AI in the mark display area 320 of the display unit 12. In this case, the display controller 215b calculates the number of images per picture element of the time bar 310 based on the number of picture elements in a time axis direction of the time bar 310 formed of a plurality of picture elements and the number of images of all in vivo images AI displayed in the main display area 300 and counts the number of lesion images detected by the aforementioned image detector 215a for each continuous image group in all in vivo images AI in which images corresponding to the unit picture element are continuous. Then, the display controller 215b performs control to display in the mark display area 320 a lesion mark having a display mode corresponding to a counting result of the number of lesion images for each continuous image group, which is a continuous image group in all in vivo images AI and contains one or more lesion images. The display controller 215b described above performs control, for example, to change the display color of lesion mark in accordance with a counting result of the number of lesion images and display in the mark display area 320 a lesion mark in the display color in accordance with the number of lesion images.

In addition, the time bar 310, slider 311, and display operation icon group 330, which are various kinds of GUIs, are made to be displayed in the display unit 212 by the display controller 215b. In this case, based on time information of each image in the aforementioned all in vivo images AI, the display controller 215b performs control to display the time bar 310 indicating the overall time positions of all in vivo images AI and performs control to display the slider 311 at the time position on the time bar 310 corresponding to the image inside the subject 1 among all in vivo images AI currently displayed in the main display area 300 (that is, the currently displayed image).

Lesion images detected by the aforementioned image detector 215a are images containing a lesion site that arose inside an organ of the subject 1 as a photographic object. An example of such lesion images is a bleeding image containing a bleeding site as a photographic object.

Figure 23:
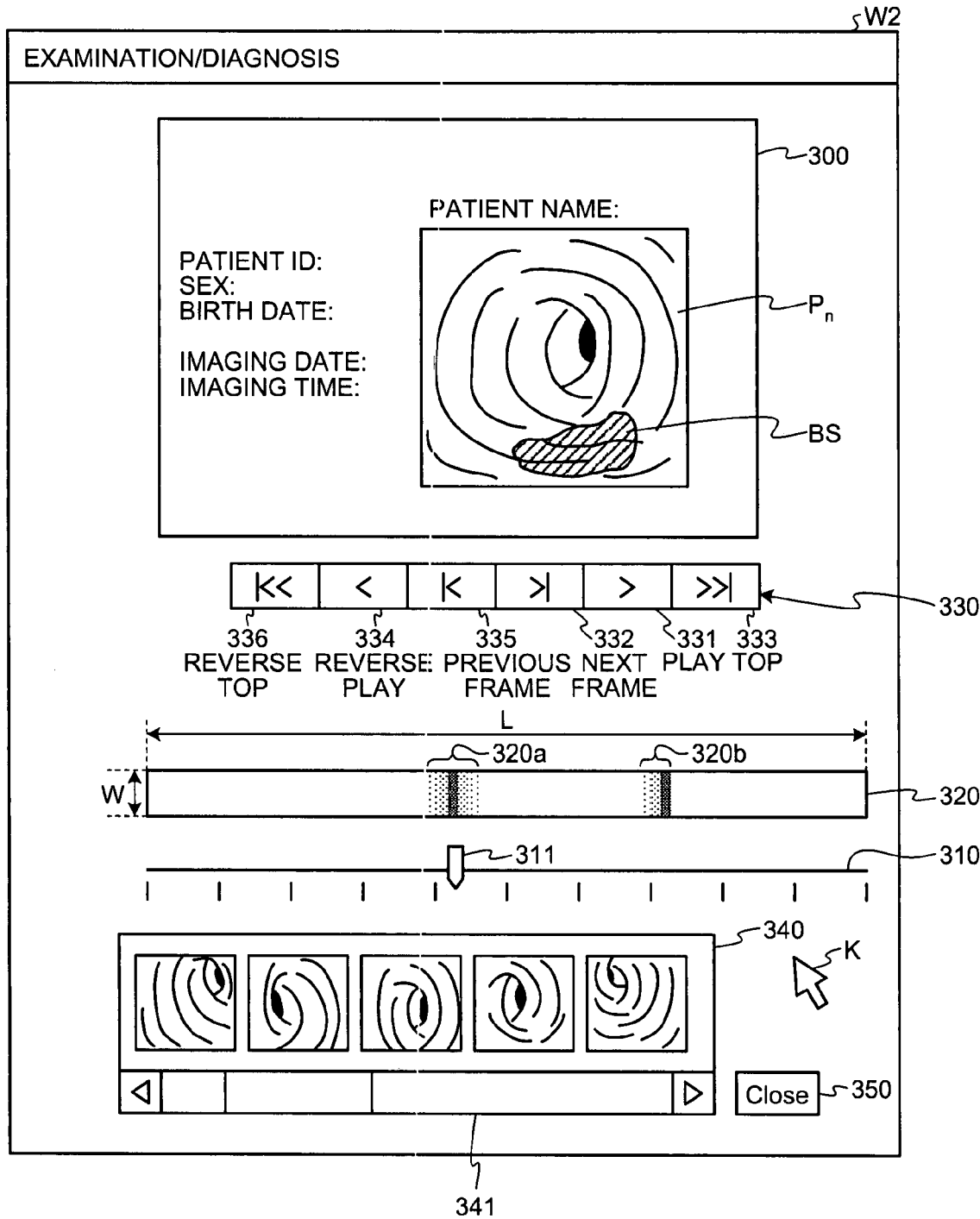
FIG. 23 is a schematic view exemplifying display content of the display unit of the image display device according to the fifth embodiment.

Next, a case in which a lesion image contained in all in vivo images AI is a bleeding image will be exemplified to concretely describe display content of the display unit 212 of the image display unit 204 according to the fifth embodiment of the present invention. FIG. 23 is a schematic view exemplifying display content of the display unit 212 of the image display device 204 according to the fifth embodiment. When predetermined login processing is performed by the control unit 215, the display controller 215b causes the display unit 212 to display a window W2 as shown in FIG. 23.

As shown in FIG. 23, the main display area 300, time bar 310, slider 311, mark display area 320, display operation icon group 330, and the display sub-area 340 are formed in the window W2. Also in the window W2, a scroll operation unit 341 for performing a scroll operation of a plurality of reduced images displayed in the display sub-area 340, a cursor K for performing a click or drag operation of various GUIs by an operation of the input unit 211 and a Close icon 350 for closing the window W2 are formed.

The main display area 300 is an image display area for displaying each image contained in all in vivo images AI to be processed for display. Based on instruction information input by the input unit 211, the display controller 215b performs control to display each image in all in vivo images AI to be processed for display in the main display area 300. The main display area 300 displays the image $P_n$ (frame number n=1, 2, 3, . . . ) in all in vivo images AI through control of the display controller 215b. The display controller 215b also performs control to display in the main display area 300 the imaging date and imaging time of the image (for example, the image $P_n$) currently displayed in the main display area 300 and patient information (patient name, patient ID, sex, and birth date) of the subject 1.

The time bar 310 and slider 311 are GUIs for indicating the time position of the image currently displayed in the main display area 300. Just like the above-described time bar 110, the time bar 310 is an elongated image component on which all in vivo images AI are mapped in a time series order with both ends thereof set for the first and the second picked-up in vivo images. Thus, the time bar 310 serves as a time scale covering from the pick up time of the first image to the pick up time of the last image. Each of all in vivo images AI can be expressed as a position on the time bar 310 which position corresponds to the position, in time series, of the in vivo image in all in vivo images AI. In this document, such the position on the time bar 310 of each in vivo image is referred to as "the time position" on the time bar 310.

Here, we assume that the length of the image constituting the time bar 310 (i.e., the longitudinal size of the time bar 310) is L pixels, which means that the time bar 310 can express L time positions. Accordingly, if the total number A of all in vivo images AI is equal to the pixel number or size L, then all in vivo images AI correspond one-to-one to all the pixels or all the time positions of the time bar 310.

If the total number A of all in vivo images AI is smaller than the pixel number L, then the mapping of all in vivo images AI on the time bar 310 is the injection, i.e., all in vivo images AI correspond one-to-one to only a pert of the pixels (or time positions) of the time bar 310. In this case, there are some pixels which do not correspond to any of all in vivo images AI in the L pixels of the time bar 310.

On the other hand, if the total number A of all in vivo images AI is larger than the pixel number L as in case detailed later, then a plurality of continuous in vivo images are assigned to each of the L pixels of the time bar 310. More specifically, L groups of continuous in vivo images into which all in vivo images AI are divided by the pixel number L correspond one-to-one to all the pixels (or time positions) of the time bar 310.

In the following description, for the sake of simplicity, we assume that the total number A of all in vivo images AI equals N times the pixel number L, i.e., A=N×L. Then, L continuous image groups into which all in vivo images AI are divided by the pixel number L correspond one-to-one to all the pixels (or time positions) of the time bar 310. An image display device 204 according to the fifth embodiment is especially advantageous to a case where the total number A of all in vivo images AI is larger than the pixel number L, and further advantageous to a case where the total in vivo image number A is N times the pixel number L.

The slider 311 moves along the time bar 310 to indicate the time position on the time bar 310 corresponding to the image currently displayed in the main display area 300. The slider 311 described above indicates the time position, on the time bar 310, of a continuous image group of N continuous in vivo images including the image currently displayed in the main display area 300. Movement of the slider 311 is controlled by the display controller 215b. The display controller 215b controls movement of the slider 311 on the time bar 310 and display switching of the image currently displayed in the main display area 300 (image inside the subject 1) so that the slider 311 indicates the time position of the image currently displayed in the main display area 300.

The mark display area 320 is an on-screen area which is the same in length as the time bar 310 and parallel to the time bar 310. More specifically, the mark display area 320 has a length of L pixels in the time axis direction and a width of W pixels in a vertical direction to the time axis. The mark display area 320 is formed of a rectangular array of L×W pixels the long side of which is aligned with the time bar 310. Accordingly, the corresponding positions of the time bar 310 and the mark display area 320 indicate an identical time position of the time scale set for the mark display area 320 and the time bar 310.

In the following description, it is assumed that the total number A of all in vivo images AI is N times the pixel length L of the mark display area 320 and/or the time bar 310. In this situation, for each time position (or each pixel) of the time bar 310, if any lesion image is included in a continuous image group of N continuous in vivo images which corresponds to the time position, then the display controller 215b displays a lesion mark quantitatively in response to the number of lesion images included in the continuous image group at a time position on the mark display area 320 corresponding to the continuous image group.

For example, the display controller 215b displays lesion mark groups 320a and 320b at the time positions of the time bar 310 corresponding to respective (two in the example of FIG. 23) bleeding image groups contained in all in vivo images AI. Each of the lesion mark groups 320a and 320b contains a plurality of lesion marks displayed corresponding to the unit picture element of the aforementioned time bar 310. The mark display area 320 displays each lesion mark in the lesion mark groups 320a and 320b per unit picture element of the time bar 310 representing a continuous image group with N images containing one or more bleeding images (that is, a continuous image group in all in vivo images AI displayed in the main display area 300). In this case, the mark display area 320 displays each lesion mark in the lesion mark groups 320a and 320b in the color (for example, red) corresponding to the lesion indicated for example by the bleeding image (that is, the bleeding site). More particularly, the mark display area 320 displays the lesion mark groups 320a and 320b in different gradations of the display color of each lesion mark (for example, red corresponding to a bleeding site) in accordance with the number of bleeding images contained in each continuous image group with N images.

The mark display area 320 having the display mode described above to display one or more lesion marks indicates the time position of each lesion image in all in vivo images AI along the time bar 310 and also functions as a time position display function indicating distribution of the numbers of lesion images in the overall time positions of all in vivo images AI (that is, the overall time positions indicated by the time bar 310). That is, the mark display area 320 displays the time positions of one or more lesion images in all in vivo images AI by one or more lesion marks exemplified by the aforementioned lesion mark groups 320a and 320b on the time bar 310 and also indicates distribution of the numbers of lesion images in the overall time positions by a display mode (for example, gradations of the display color) of such lesion marks.

Thus, if the image currently displayed in the main display area 300 (an image $P_n$ inside the subject 1) is a bleeding image containing the bleeding site BL as a photographic object while the mark display area 320 displays lesion mark groups 320a and 320b, the slider 311 moves to the position of a lesion mark in the lesion mark group 320a indicating the time position of the bleeding image, that is, the time position corresponding to the unit picture element of the time bar 310 representing the continuous image group with N images containing the bleeding image.

The display operation icon group 330 is GUI for performing display operations when displaying in the main display area 300 each image contained in all in vivo images AI. The display operation icon group 330 includes, as shown in FIG. 23, for example, a play icon 331, next frame icon 332, top search icon 333, reverse play icon 334, previous frame icon 335, and reverse top search icon 336. The play icon 331 is a GUI for playing each image in all in vivo images AI in the forward direction of a time series and the next frame icon 332 is a GUI for playing each image in all in vivo images AI on a single frame basis in the forward direction of a time series. The reverse play icon 334 is a GUI for playing each image in all in vivo images AI in the backward direction of a time series and the previous frame icon 335 is a GUI for playing each image in all in vivo images AI on a single frame basis in the backward direction of a time series. The top search icon 333 is a GUI for displaying the image picked up last and the reverse top search icon 336 is a GUI for displaying the image picked up first of all in vivo images AI.

Figure 24:
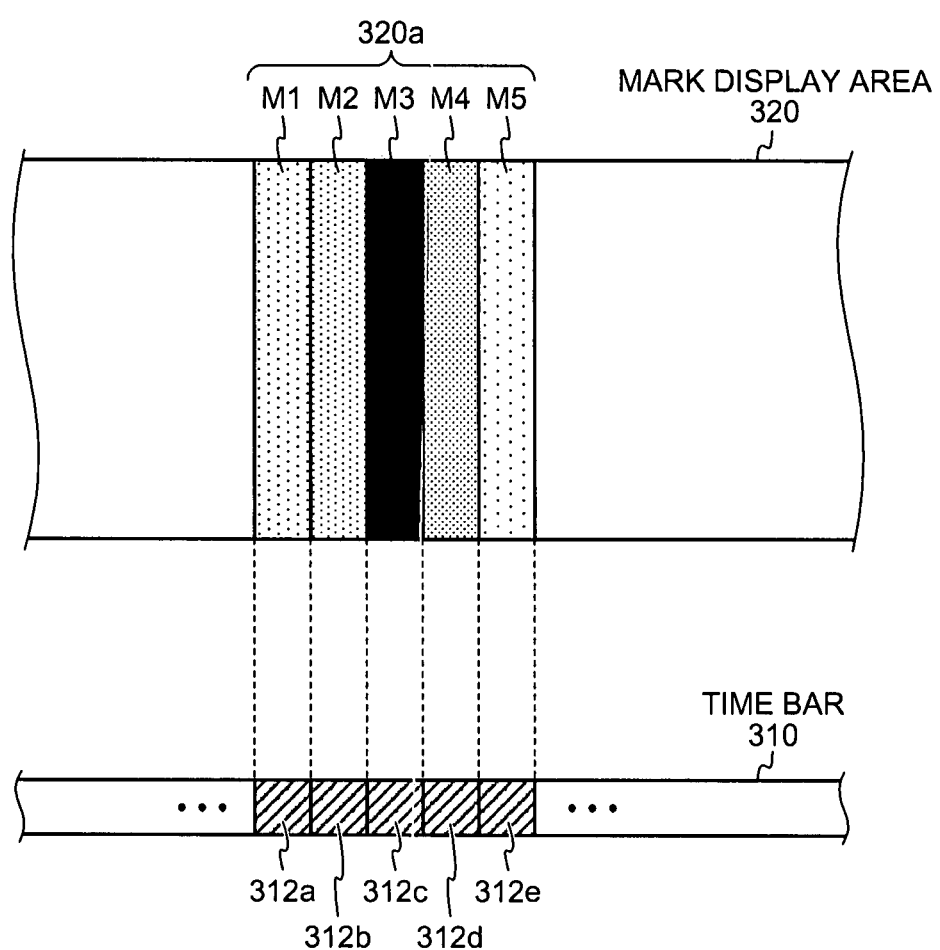
FIG. 24 is a schematic view showing a concrete example of the lesion mark which a display controller of the image display device according to the fifth embodiment causes a mark display unit to display.

Next, the lesion mark group 320a in the aforementioned mark display area 320 will be exemplified to describe in detail lesion marks displayed by the mark display area 320 based on control of the display controller 215b. FIG. 24 is a schematic view showing a concrete example of the lesion mark which the display controller 215b of the image display device 204 according to the fifth embodiment causes the mark display area 320 to display. FIG. 24 shows an enlarged view of the lesion mark group 320a displayed by the mark display area 320.

As shown in FIG. 24, the lesion mark group 320a contains, for example, five lesion marks M1 to M5 displayed along a sequence of picture elements in the time axis direction forming the time bar 310. The lesion marks M1 to M5 are displayed corresponding to unit picture elements 312a to 312e of the time bar 310 respectively. Each of the lesion marks M1 to M5 indicates the time positions of one or more lesions images contained in each continuous image group with N images in all in vivo images AI represented by the unit picture elements 312a to 312e respectively.

More specifically, the lesion marks M1 to M5 are each bar-shaped marks perpendicular to the time axis of the time bar 310 formed by a group of picture elements arranged in the time axis direction and are formed by a group of picture elements arranged one-dimensionally in a direction perpendicular to the time axis of the time bar 310. In this case, a group of picture elements forming the lesion mark M1 is arranged one-dimensionally corresponding to the unit picture element 312a of the time bar 310. Similarly, each group of picture elements corresponding to the lesion marks M2 to M5 is arranged one-dimensionally corresponding to the unit picture elements 312b to 312e of the time bar 310 respectively. The number of picture elements of each group of picture elements forming the lesion marks M1 to M5 corresponds to the width W of the aforementioned mark display area 320.

The lesion mark M1 described above represents one or more bleeding images contained in the continuous image group (the aforementioned continuous image group with N images) in all in vivo images AI represented by the unit picture element 312a of the time bar 310 and also collectively shows the time position of bleeding images in the continuous image group represented by the unit picture element 312a. Similarly, the lesion marks M2 to M5 represent one or more bleeding images contained in each continuous image group with N images represented by the unit picture elements 312b to 312e of the time bar 310 respectively and also collectively show the time positions of bleeding images in each continuous image group represented by the unit picture elements 312b to 312e respectively.

The display color of the lesion marks M1 to M5 changes depending on the number of bleeding images in each continuous image group with N images represented by the unit picture elements 312a to 312e of the time bar 310 respectively. More specifically, if the lesion marks M1 to M5 are displayed in similar colors (for example, reddish colors) corresponding to the lesion indicated by bleeding images (that is, the bleeding site), each display color of the lesion marks M1 to M5 becomes darker with an increasing number of bleeding images in each continuous image group with N images represented by the unit picture elements 312a to 312e respectively and becomes lighter with a decreasing number of bleeding images.

The lesion marks M1 to M5 described above indicate the time positions of bleeding images for each continuous image group with N images in all in vivo images AI containing one or more bleeding images and also shows distribution of the numbers of bleeding images for each continuous image group with N images by the display color thereof (for example, reddish gradations). This also applies to the lesion mark group 320*b*.

Lightness of the background of the mark display area 320 displaying such lesion marks (that is, the rectangular area specified by the length L and width W) has desirably an approximately mean value between lightness of a lesion mark and that of the background of the window W2 and the background color of the mark display area 320 is desirably a complementary color of the lesion mark. This makes the boundary between the background of the mark display area 320 and lesion marks clear, and as a result, lesion marks can be displayed by mark display area 320 in such an aspect that can easily be confirmed visually by a user such as a physician and nurse.

Figure 25:
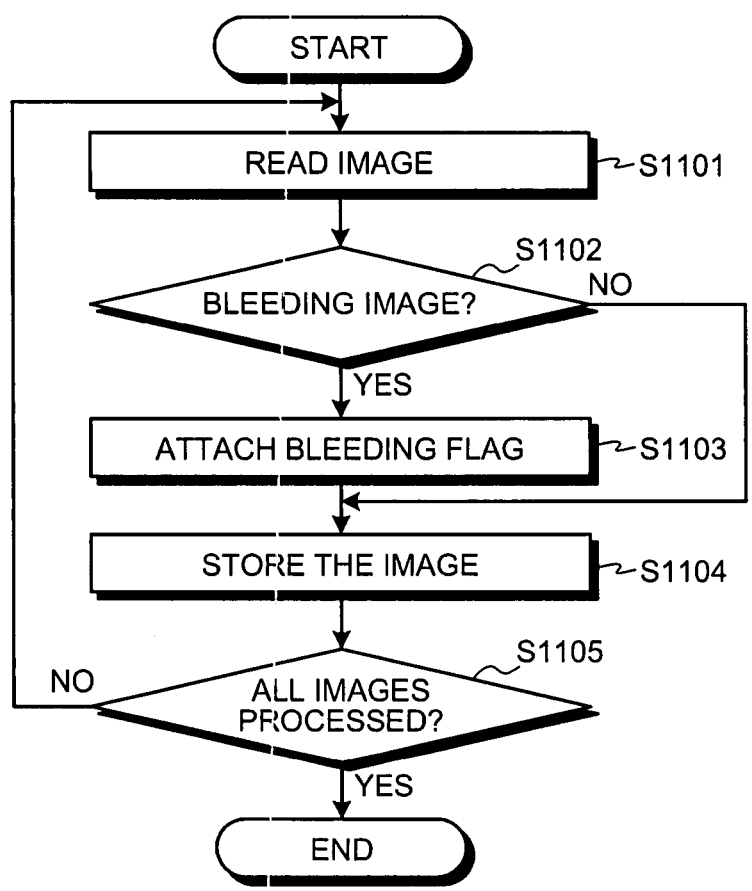
FIG. 25 is a flow chart exemplifying the processing procedure of the control unit detecting one or more bleeding images contained in a group of images inside a subject.

Next, a case in which a bleeding image as an example of a lesion image is contained in all in vivo images AI will be exemplified to describe an operation of the control unit 215 to detect the bleeding image in all in vivo images AI. FIG. 25 is a flow chart exemplifying the processing procedure of the control unit 215 detecting one or more bleeding images contained in all in vivo images AI.

As shown in FIG. 25, the control unit 215 first reads an image to be processed from among all in vivo images AI (step S1101). In this case, the control unit 215 successively reads the image $P_n$ (frame number n=1, 2, 3, . . . ) to be processed from all in vivo images AI stored in the portable recording medium 205 inserted in the card interface 213, for example, in a time series.

Next, the control unit 215 determines whether the image inside the subject 1 read as an image to be processed is a bleeding image (step S1102). In this case, the image detector 215*a* detects color information of the read image to be processed and, based on the detected color information, determines whether the image to be processed is a bleeding image. More specifically, if the image detector 215*a* detects an average color of the image as the color information of the image to be processed and the detected average color of the image closely resembles that of a bleeding image, the image detector 215*a* determines that the image to be processed is a bleeding image inside the subject 1. If, on the other hand, the image detector 215*a* detects values of RGB color elements (R value, G value, B value) forming the image as color information of the image to be processed and each detected color element value of RGB is within the range of each color element of RGB of a bleeding image, the image detector 215*a* determines that the image to be processed is a bleeding image inside the subject 1.

If the image to be processed is determined to be a bleeding image (step S1102, Yes), the control unit 215 attaches a bleeding flag to the image to be processed that has been determined to be a bleeding image (step S1103). In this case, the image detector 215*a* attaches a bleeding flag indicating a bleeding image to the image to be processed that has been determined to be a bleeding image in the aforementioned step S1102 (that is, the bleeding image inside the subject 1). In this way, the image detector 215*a* detects any bleeding image contained in all in vivo images AI. The bleeding flag attached to a bleeding image inside the subject 1 is an example of the aforementioned lesion flag and a sign indicating a bleeding image.

Next, the control unit 215 stores the image to be processed having the attached bleeding flag (that is, the bleeding image) in the storage unit 214 (step S1104). In this case, the control unit 215 stores the bleeding image having the attached bleeding flag in the storage unit 214 as part of all in vivo images AI.

Subsequently, the control unit 215 determines whether processing of all images contained in all in vivo images AI has been completed (step S1105). More specifically, if any image inside the subject 1 that has not been read remains in the portable recording medium 205 inserted in the card interface 213 or any image inside the subject 1 that has not been stored in the storage unit 214 remains in the portable recording medium 205, the control unit 215 determines that processing of all in vivo images AI has not been completed (step S1105, No) and returns to the aforementioned step S1101 to repeat the processing procedure of step S1101 and thereafter.

The control unit 215 performs the processing procedure of the aforementioned steps S1101 to S1105 for each image contained in all in vivo images AI repeatedly and stores all in vivo images AI containing any bleeding image with the attached bleeding flag in the storage unit 214.

If, on the other hand, all images in all in vivo images AI have been read from the portable recording medium 205 inserted in the card interface 213 or all images in all in vivo images AI stored in the portable recording medium 205 have been stored in the storage unit 214, the control unit 215 determines that processing of all images in all in vivo images AI has been completed (step S1205, Yes) and terminates detection processing of bleeding images in all in vivo images AI.

Meanwhile, if the control unit 215 determines that an image to be processed is not a bleeding image in the aforementioned step S1102 (step S1102, No), the control unit 215 proceeds to the aforementioned step S1104 to repeat the processing procedure of step S1104 and thereafter. In this case, the image detector 215*a* does not attach any bleeding flag to the image inside the subject 1 determined not to be a bleeding image in step S1102 (that is, a normal organ image). The control unit 215 stores the image inside the subject 1 with no attached bleeding flag, that is, the normal organ image in the storage unit 214. That is, the image inside the subject 1 that is not a bleeding image is stored in the storage unit 214 as part of all in vivo images AI without a bleeding flag being attached.

Figure 26:
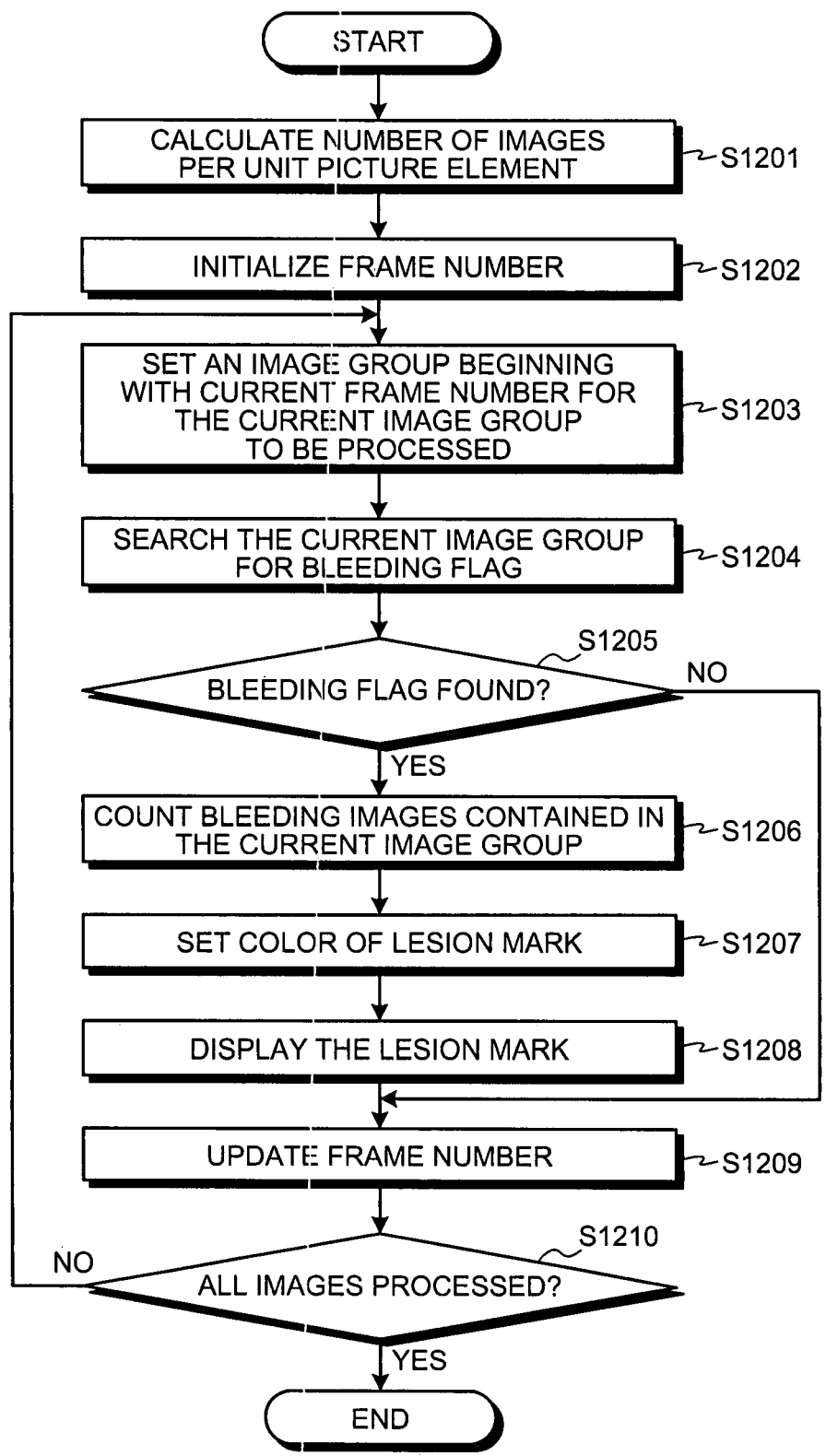
FIG. 26 is a flow chart showing an example of the processing procedure of the control unit performing control to display a lesion mark having the display color corresponding to a counting result of bleeding images.

Next, a case in which all in vivo images AI containing a bleeding image, which is an example of lesion image, will be exemplified to describe an operation of the control unit 215 that performs control to display a lesion mark indicating the time position of the bleeding image inside the subject 1. FIG. 26 is a flow chart showing an example of the processing procedure of the control unit 215 performing control to display a lesion mark having the display color corresponding to a counting result of bleeding images.

The control unit 215 counts the number of bleeding images for each continuous image group with N images in all in vivo images AI displayed in the main display area 300 and causes the mark display area 320 to display a lesion mark having a display color in accordance with a counting result of the number of bleeding images for each continuous image group with N images containing one or more bleeding images (that is, images having an attached bleeding flag) detected by the image detector 215*a*.

That is, as shown in FIG. 26, the control unit 215 first calculates the number N of images per unit picture element of the time bar 310 (step S1201). More specifically, the display controller 215*b* detects the total number A of images [frames] in all in vivo images AI displayed in the main display area 300 and the length L [picture elements] of the time bar 310. Here, the length L of the time bar 310 is the same as the number of picture elements (sequence of picture elements) forming the time bar 310. The display controller 215*b* calculates the number N of images [frames/unit picture element] per unit picture element of the time bar 310 by dividing the total number A of images by the length L (that is, L picture elements). Meanwhile, the number N of images per unit picture element is the number of images of a continuous image group in all in vivo images AI represented by the unit picture element of the time bar 310.

Next, the control unit 215 initializes the frame number n of all in vivo images AI displayed in the main display area 300 (step S1202). In this case, the display controller 215*b* initializes the frame number n to identify the first image in a continuous image group with N images contained in all in vivo images AI to an initial value (for example, n=1).

Subsequently, the control unit 215 determines a continuous image group to be processed for which counting processing of the number of bleeding images is performed from all in vivo images AI displayed in the main display area 300 (step S1203). In this case, the display controller 215*b* sets the image of the current frame number n as the first image to determine a continuous image group in all in vivo images AI in which N images are continuous (that is, a continuous image group with N images) as the continuous image group to be processed.

Meanwhile, the frame number n to identify the first image of the continuous image group with N images determined as the continuous image group to be processed is the frame number initialized in the aforementioned step S1202 or the frame number updated in step S1209 described later.

Next, the control unit 215 searches for any bleeding flag in the continuous image group with N images determined as the continuous image group to be processed in step S1203 (step S1204). In this case, the display controller 215*b* sequentially reads each image contained in the continuous image group with N images in order of frame number to search each read image for a bleeding flag. Here, if any bleeding image is contained in a continuous image group with N images, the display controller 215*b* reads such a bleeding image in the continuous image group and reads the bleeding flag attached to the bleeding image. By reading the bleeding flag as well as the bleeding image, the display controller 215*b* detects the bleeding flag attached to the bleeding image. That is, if one or more bleeding images are contained in a continuous image group with N images, the display controller 215*b* detects as many bleeding flags as the number of bleeding images from the continuous image group with N images.

Subsequently, based on a search result of the bleeding flag of search processing in step S1204, the control unit 215 determines whether there is any bleeding flag in the continuous image group with N images (step S1205). More specifically, if one or more bleeding flags are detected in a continuous image group with N images, the display controller 215*b* determines that there is a bleeding flag in the continuous image group with N images.

If it is determined that there is a bleeding flag in the continuous image group with N images determined as a continuous image group to be processed, as described above (step S1205, Yes), the control unit 215 counts the number of bleeding images contained in the continuous image group to be processed (step S1206). In this case, the display controller 215*b* counts the bleeding flags detected from among the continuous image group with N images determined as the continuous image group to be processed. Here, as described above, the number of detected bleeding flags is the same as the number of bleeding images in a continuous image group with N images. Therefore, by counting the number of detected bleeding flags, the display controller 215*b* obtains the number x of bleeding images [frames]contained in the continuous image group with N images.

Next, the control unit 215 sets the display color of lesion marks indicating the time positions of one or more bleeding images contained in the continuous image group with N images corresponding to the number x of bleeding images obtained in step S1206 (step S 1207). In this case, the display controller 215*b* calculates color elements of the lesion mark using the number x of bleeding images in the continuous image group with N images and sets the color formed by the obtained color elements as the display color of the lesion mark.

More specifically, the display controller 215*b* calculates the color elements of the lesion mark indicating the time positions of one or more bleeding images contained in the continuous image group with N images based on, for example, the following formula (1) containing the number x of bleeding images in the continuous image group with N images as a variable and the following formulae (2) and (3) and then sets the color formed by the obtained color elements as the display color of the lesion mark.

$$R \text{ value}=64+2\times \text{number } x \text{ of bleeding images} \qquad (1)$$

$$G \text{ value}=0 \qquad (2)$$

$$B \text{ value}=0 \qquad (3)$$

Here, the color formed by color elements calculated based on the above formulae (1) to (3) is a reddish color corresponding to the lesion indicated by bleeding images (that is, a bleeding site), and becomes darker with an increasing number x of bleeding images in the continuous image group with N images and becomes lighter with a decreasing number x of bleeding images. By setting the display color of a lesion mark based on the formulae (1) to (3), the display controller 215*b* changes gradations of the display color of a lesion mark in accordance with the number x of bleeding images in the continuous image group with N images.

Next, the display controller 215*b* controls the display unit 212 to display a lesion mark having the display color set in step S1207 (step S1208). In this case, the display controller 215*b* performs control to display a lesion mark having the display color in accordance with the number x of bleeding images in the continuous image group with N images (that is, the display color set in step S1207) at the time position in the mark display area 320 corresponding to the unit picture element of the time bar 310 representing the continuous image group with N images. Based on the control of the display controller 215*b*, the mark display area 320 displays a lesion mark in the display color in accordance with the number x of bleeding images in the continuous image group with N images in a picture element sequence of time positions corresponding to the unit picture element of the time bar 310 representing the continuous image group with N images.

Next, the control unit 215 updates the frame number n of all in vivo images AI displayed in the main display area 300 (step S1209). In this case, the display controller 215*b* adds the number N of images (number of images calculated in the aforementioned step S1201) to the current frame number n identifying the first image in the continuous image group currently to be processed to update the frame number n to the obtained value. The frame number n obtained in this manner identifies the first image in the next continuous image group in all in vivo images AI following the continuous image group currently to be processed.

Subsequently, the control unit 215 determines whether processing of all images in all in vivo images AI displayed in the main display area 300 has been completed (step S1210). More specifically, if the updated frame number n in the aforementioned step S1209 is equal to or smaller than the total number A of images in all in vivo images AI, the display controller 215*b* determines that processing of at least one image contained in all in vivo images AI has not been completed (step S1210, No) and returns to the aforementioned step S1203 to repeat the processing procedure of step S1203 and thereafter.

If, on the other hard, the updated frame number n in the aforementioned step S1209 exceeds the total number A of images in all in vivo images AI, the display controller 215*b* determines that processing of all images contained in all in vivo images AI has been completed (step S1210, Yes) and terminates lesion mark display processing for all in vivo images AI. In this state, the mark display area 320 displays a lesion mark having the display color in accordance with the number x of bleeding images for each continuous image group containing one or more bleeding images from among continuous image groups with N images contained in all in vivo images AI.

If, in the aforementioned step S1205, the control unit 215 determines that there is no bleeding flag in the continuous image group with N images, which is the continuous image group to be processed (step S1205, No), the control unit 215 proceeds to step S1209 without performing the processing procedure of steps S1206 to S1208. In this case, the display controller 215*b* has not detected any bleeding flag in the continuous image group with N images in the aforementioned step S1204. That is, the continuous image group with N images contains no bleeding image. If the continuous image group with N images contains no bleeding image, no lesion mark is made to be displayed by the display controller 215*b* at the time position in the mark display area 320 corresponding to the unit picture element of the time bar 310 representing the continuous image group with N images.

Figure 27:
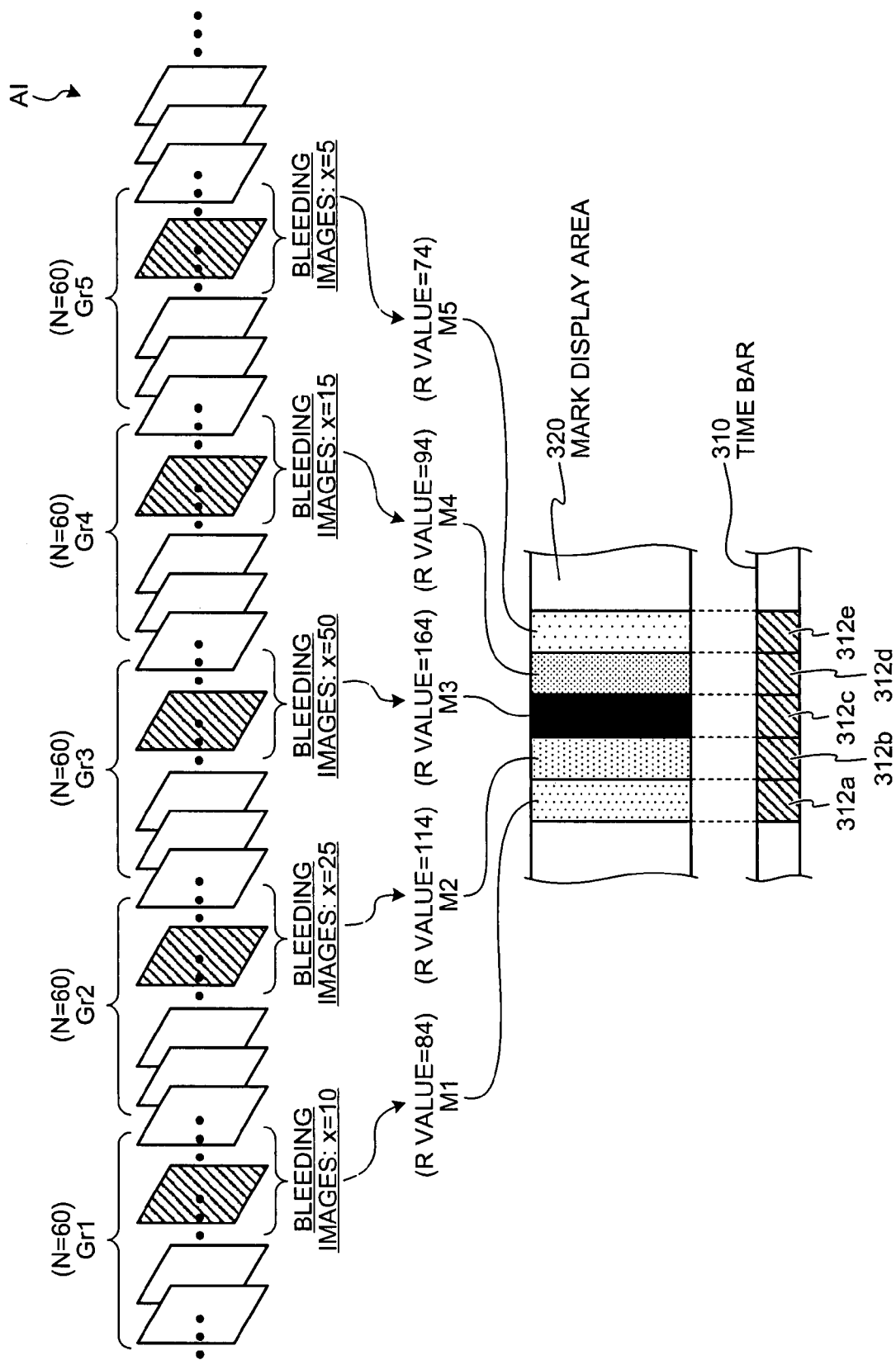
FIG. 27 is a schematic view concretely illustrating an operation of the display controller performing control to display a lesion mark having the display color in accordance with the number of bleeding images.

Next, the lesion marks M1 to M5 (See FIGS. 23 and 24) indicating the time positions of bleeding images contained in all in vivo images AI will be exemplified to concretely describe an operation of the display controller 215*b* that performs control to display a lesion mark having the display color in accordance with the number x of bleeding images for each continuous image group containing one or more bleeding images in all in vivo images AI. FIG. 27 is a schematic view concretely illustrating an operation of the display controller 215*b* performing control to display a lesion mark having the display color in accordance with the number x of bleeding images.

All in vivo images AI inside the subject 1 displayed in the main display area 300 is, for example, a group of images of 60,000 frames (that is, a group of images whose total number A of images is 60,000 frames) and contains a plurality of bleeding images. If, here, the length L of the time bar 310 (that is, the number of picture elements in the time axis direction forming the time bar 310) is 1,000 picture elements, the display controller 215*b* divides the total number A of images (=60,000 frames) in all in vivo images AI by the length L (=1,000 picture elements) of the time bar 310 to calculate the number N of images (=60 frames) per unit picture element of the time bar 310.

Subsequently, the display controller 215*b* determines a continuous image group one by one in all in vivo images AI in which N images are continuous per unit picture element and counts the number x of bleeding images in each continuous image group with N images. Then, the display controller 215*b* performs control to display a lesion mark in the display color in accordance with the number x of bleeding images for each continuous image group with N images containing one or more bleeding images.

More specifically, as shown in FIG. 27, the display controller 215*b* determines a continuous image group Gr1 of 60 frames in which as many images as the number N of images (=60 frames) corresponding to the unit picture element are continuous from among all in vivo images AI. The continuous image group Gr1 is represented by the unit picture element 312*a* of the time bar 310. That is, the time position of the continuous image group Gr1 corresponds to the unit picture element 312*a*.

The display controller 215*b* performs search processing of the bleeding flag in the continuous image group Gr1 and, based on a search result of the bleeding flag, counts the number x of bleeding images in the continuous image group Gr1. If, for example, 10 frames of bleeding images are contained in the continuous image group Gr1, the display controller 215*b* detects 10 bleeding flags from the continuous image group Gr1 and counts the number (=10) of detected bleeding flags as the number x of bleeding images in the continuous image group Gr1. In this way, the display controller 215*b* obtains the number x=10 of bleeding images in the continuous image group Gr1.

If 10 frames of bleeding images are contained in the continuous image group Gr1, the display controller 215*b* sets the display color for the lesion mark in accordance with the number x=10 of bleeding images in the continuous image group Gr1. More specifically, the display controller 215*b* calculates the color elements (R value=84, G value=0, and B value=0) in accordance with the number x=10 of bleeding images based on the aforementioned formulae (1) to (3) and sets the display color for the lesion mark formed by the obtained color elements.

The display controller 215*b* performs control to display the lesion mark M1 having the display color (R value=84, G value=0, and B value=0) set as described above at the time position in the mark display area 320 corresponding to the unit picture element 312*a*. Based on the control of the display controller 215*b*, the mark display area 320 displays the lesion mark M1 at the time position corresponding to the unit picture element 312*a*.

Subsequently, approximately similarly to the aforementioned continuous image group Gr1, the display controller 215*b* determines continuous image groups Gr2 to Gr5 one by one in all in vivo images AI in which N images are continuous per unit picture element of the time bar 310 and the number x of bleeding images is counted for each of the determined continuous image groups Gr2 to Gr5. Then, approximately similarly to the aforementioned lesion mark M1, the display controller 215*b* perform control to display the lesion marks M2 to M5 having the display colors in accordance with the numbers x of bleeding images of the continuous image group Gr2 to Gr5 respectively.

More specifically, the continuous image groups Gr2 to Gr5 are continuous image groups of 60 frames in which the aforementioned number N=60 of images are continuous and each contains one or more bleeding images. The continuous image groups Gr2 to Gr5 are continuous one after another following the aforementioned continuous image group Gr1. That is, the continuous image group Gr2 follows the continuous image group Gr1, the continuous image group Gr3 follows the continuous image group Gr2, the continuous image group Gr4 follows the continuous image group Gr3, and the continuous image group Gr5 follows the continuous image group Gr4. These continuous image groups Gr2 to Gr5 are represented by the unit picture elements 312*b* to 312*e* of the time bar 310 respectively. That is, the unit picture elements 312*b* to 312*e* of the time bar 310 correspond to each time position of the continuous image groups Gr2 to Gr5 respectively.

The display controller 215b counts the number of detected bleeding flags in each of the continuous image groups Gr2 to Gr5 one by one to obtain the number x=25 of bleeding images in the continuous image group Gr2, the number x=50 of bleeding images in the continuous image group Gr3, the number x=15 of bleeding images in the continuous image group Gr4, and the number x=5 of bleeding images in the continuous image group Gr5 one by one. The display controller 215b described above sets, based on the aforementioned formulae (1) to (3), the display color (R value=114, G value=0, and B value=0) for the lesion mark M2 in accordance with the number x=25 of bleeding images in the continuous image group Gr2, the display color (R value=164, G value=0, and B value=0) for the lesion mark M3 in accordance with the number x=50 of bleeding images in the continuous image group Gr3, the display color (R value=94, G value=0, and B value=0) for the lesion mark M4 in accordance with the number x=15 of bleeding images in the continuous image group Gr4, and the display color (R value=74, G value=0, and B value=0) for the lesion mark M5 in accordance with the number x=5 of bleeding images in the continuous image group Gr5 one by one.

The display controller 215b performs control to display the lesion marks M2 to M5 having the display colors in accordance with the numbers x of bleeding images at each time position in the mark display area 320 corresponding to the unit picture elements 312b to 312e respectively. Based on the control of the display controller 215b, the mark display area 320 displays the lesion marks M2 to M5 at each time position corresponding to the unit picture elements 312b to 312e respectively.

Here, the lesion marks M1 to M5 displayed by control of the display controller 215b represent each bleeding image group contained in the continuous image groups Gr1 to Gr5 respectively and are formed of each picture element sequence in the mark display area 320 corresponding to the unit picture element 312a to 312e of the time bar 310 respectively. The lesion mark M1 has the display color (R value=84, G value=0, and B value=0) in accordance with the number x=10 of bleeding images in the continuous image group Gr1, the lesion mark. M2 has the display color (R value=114, G value=0, and B value=0) in accordance with the number x=25 of bleeding images in the continuous image group Gr2, the lesion mark M3 has the display color (R value=164, G value=0, and B value=0) in accordance with the number x=50 of bleeding images in the continuous image group Gr3, the lesion mark M4 has the display color (R value=94, G value=0, and B value=0) in accordance with the number x=15 of bleeding images in the continuous image group Gr4, and the lesion mark M5 has the display color (R value=74, G value=0, and B value=0) in accordance with the number x=5 of bleeding images in the continuous image group Gr5.

Each display color of the lesion marks M1 to M5 is red corresponding to a bleeding site shown by bleeding images (that is, a color easily associated with a bleeding site) and becomes darker with an increasing number x of bleeding images in each of the continuous image groups Gr1 to Gr5. More specifically, the display color of the lesion mark M3 representing bleeding images of the number x=50 of bleeding images is darker red compared with the display colors of the lesion marks M1, M2, M4, and M5 representing less than 50 bleeding images. The display color of the lesion mark M2 representing bleeding images of the number x=25 of bleeding images is darker red compared with the display colors of the lesion marks M1, M4, and M5 representing less than 25 bleeding images. The display color of the lesion mark M4 representing bleeding images of the number x=15 of bleeding images is darker red compared with the display colors of the lesion marks M1, and M5 representing less than 15 bleeding images. The display color of the lesion mark M1 representing bleeding images of the number x=10 of bleeding images is darker red compared with the display colors of the lesion mark M5 representing less than 10 bleeding images.

The lesion marks M1 to M5 described above indicate each time position of bleeding images contained in the continuous image groups Gr1 to Gr5 along the time bar 310 respectively and also can indicate distribution of the numbers of bleeding images in the continuous image groups Gr1 to Gr5 along the time bar 310 by the depth of each display color (more specifically, red). In this case, the lesion marks M1 to M5 can indicate more or less of the number of bleeding images when compared among the continuous image groups Gr1 to Gr5 by a difference in depth of the display color among lesion marks.

A user such as a physician and nurse can understand over which time position of the overall time positions of all in vivo images AI bleeding images are distributed based on the display positions of the lesion marks M1 to M5 displayed along the time bar 310. At the same time, the user can easily understand distribution of the numbers of bleeding images in the overall time positions of all in vivo images AI based on the display color of the lesion marks M1 to M5 and also more or less of the number of bleeding images when compared among time positions of such bleeding images.

Meanwhile, the aforementioned display controller 215b performs control to display the image $P_n$ (frame number n=1, 2, 3, . . . ) in all in vivo images AI in the main display area 300 based on display instruction information input by an operation of the display operation icon group 330 shown in FIG. 23. More specifically, the input unit 211 inputs display instruction information corresponding to a desired icon into the control unit 215 by performing a click operation of the desired icon among the aforementioned display operation icon group 330. Based on the display instruction information input by the input unit 211, the display controller 215b performs control to display the $P_n$ in all in vivo images AI in the main display area 300.

If, for example, a click operation of the play icon 331 is performed, the image $P_n$ inside the subject 1 is made to be successively displayed in the main display area 300 by the display controller 215b in the forward direction of the time series and, when a click operation of the next frame icon 332 is performed, one frame of the image $P_n$ inside the subject 1 is made to be displayed in the main display area 300 in the forward direction of the time series each time the click operation is performed. When a click operation of the reverse play icon 334 is performed, the image $P_n$ inside the subject 1 is made to be successively displayed in the main display area 300 by the display controller 215b in the backward direction of the time series and, when a click operation of the previous frame icon 335 is performed, one frame of the image $P_n$ inside the subject 1 is made to be displayed in the main display area 300 in the backward direction of the time series each time the click operation is performed.

When, a click operation of the top search icon 333 is performed, on the other hand, the end image in all in vivo images AI is made to be displayed in the main display area 300 by the display controller 215b. When a click operation of the reverse top search icon 336 is performed, the first image in all in vivo images AI is made to be displayed in the main display area 300 by the display controller 215b.

As has been described, in the fifth embodiment of the present invention, the image display device is configured in such ways that one or more bleeding images contained in a group of images inside a subject picked up inside organs in a time series are detected, the total number of images inside the subject is divided by the number of picture elements in the time axis direction forming a time bar indicating overall time positions of the group of images inside the subject to calculate the number of images per unit picture element of the time bar, the number of bleeding images is counted for each continuous image group in the group of images inside the subject in which images corresponding to the unit picture element are continuous, and for each continuous image group containing one or more bleeding images, a lesion mark indicating the time position of bleeding images in the continuous image group is displayed in a display color (for example, a display color with different depth in accordance with the number of bleeding images) in accordance with the number of bleeding images in the continuous image group. Thus, the time position of bleeding images in the overall time positions of the group of images inside the subject can be indicated by the display positions of one or more lesion marks displayed along the time bar and also distribution of the numbers of bleeding images in the overall time positions by the display color of one or more lesion marks. As a result, a user can understand the time position of lesion images such as bleeding images contained in the group of images inside organs picked up in a time series and also an image display device that enables the user to easily understand distribution of the numbers of lesion images in the overall time positions of the group of images inside organs can be realized.

By using the image display device according to the fifth embodiment, the user can understand the time positions of one or more lesion images contained in a group of images inside a subject and, based on the time position, easily estimate an organ inside the subject in which lesion images have been picked up. In addition, the user can easily understand distribution of the numbers of lesion images in the overall time positions of the group of images inside the subject and easily estimate a rough number of lesion images close to the actual number of lesion images contained in the group of images inside the subject.

Sixth Embodiment

Next, a sixth embodiment of the present invention will be described. While, in the aforementioned fifth embodiment, the display color of each lesion mark is changed in accordance with the number x of bleeding images counted for each continuous image group in which as many images as the number N of images per unit picture element of the time bar 310 are continuous, in the sixth embodiment, the display size of each lesion mark is changed in accordance with the number x of bleeding images.

Figure 28:
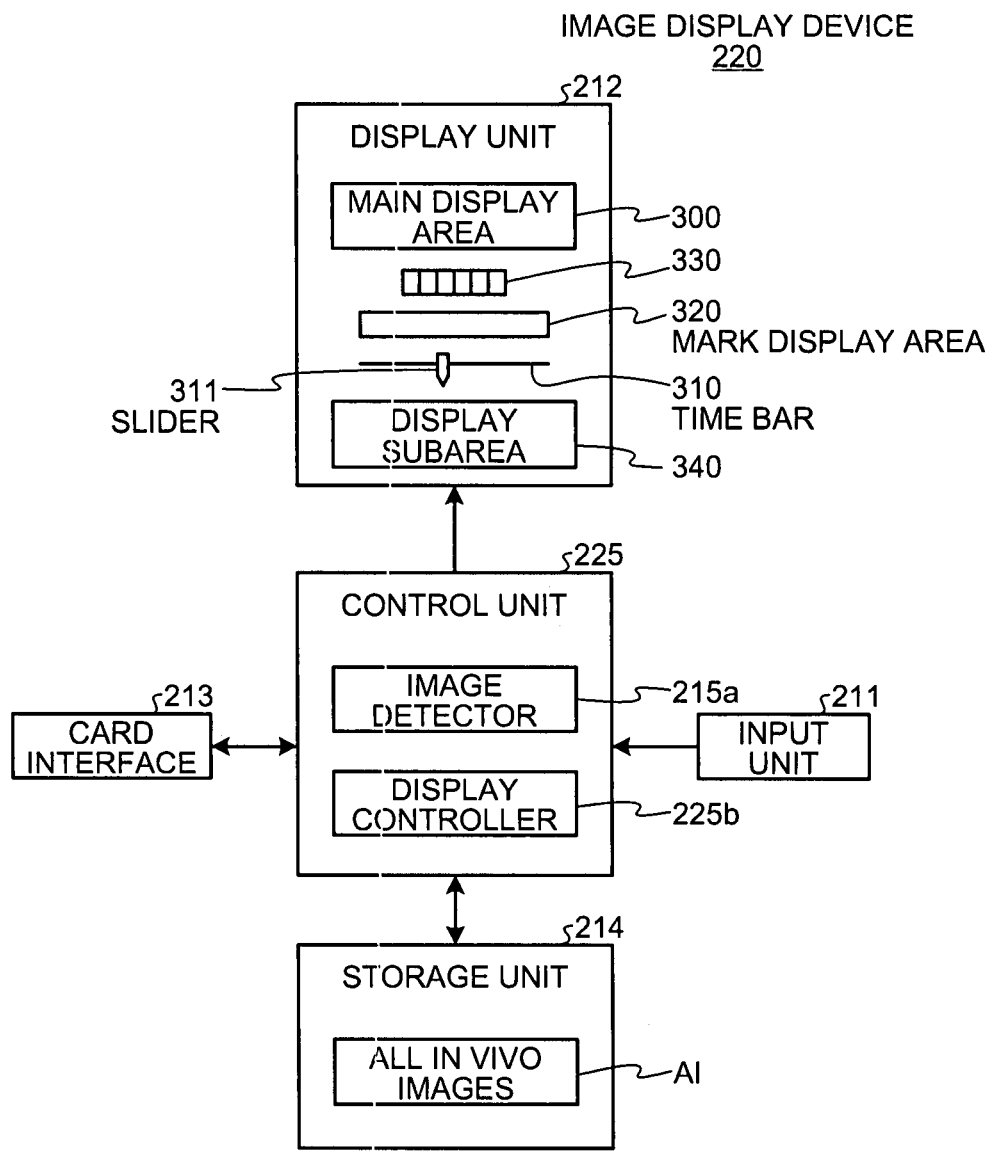
FIG. 28 is a block diagram schematically showing a configuration example of an image display device according to a sixth embodiment of the present invention.

FIG. 28 is a block diagram schematically showing a configuration example of an image display device according to a sixth embodiment of the present invention. As shown in FIG. 28, an image display device 220 according to the sixth embodiment has a control unit 225 instead of the control unit 215 of the image display device 204 according to the aforementioned fifth embodiment. In the image display device 220, the mark display area 320 of the display unit 212 displays each lesion mark, instead of changing the display color in accordance with the number x of bleeding images counted for each continuous image group with N images in all in vivo images AI, by changing the display size in accordance with the number x of bleeding images. An in-vivo information acquiring system according to the sixth embodiment of the present invention has the image display device 220 instead of the image display device 204 in the in-vivo information acquiring system according to the aforementioned fifth embodiment (See FIG. 21). Other components are the same as those of the fifth embodiment and the same numeral is attached to the same component.

The control unit 225 has the same functions as those of the control unit 215 of the image display device 204 according to the aforementioned fifth embodiment except for the mark display control function that performs control to display a lesion mark of the display size in accordance with the number x of bleeding images for each continuous image group with N images in all in vivo images AI containing one or more bleeding images. The control unit 225 described above has the image detector 215a like the control unit 215 of the image display device 204 according to the fifth embodiment and a display controller 225b instead of the aforementioned display controller 215b.

The display controller 225b performs control to display in the mark display area 320 of the display unit 212 lesion marks indicating the time positions of one or more lesion images (for example, bleeding images) contained in all in vivo images AI. More specifically, like the display controller 215b in the aforementioned fifth embodiment, the display controller 225b calculates the number N of images per unit picture element of the time bar 310 and counts the number x of bleeding images in each continuous image group with N continuous images in all in vivo images AI. If the number x of bleeding images in each continuous image group with N images is one or more, that is, if the continuous image group with N images contains one or more bleeding images, the display controller 225b each time causes the mark display area 320 to display a lesion mark having the display size in accordance with the number x of bleeding images of the continuous image group containing one or more bleeding images. In this case, the display controller 225b sets a reddish color (a color easily associated with a bleeding site) corresponding to a bleeding site shown by bleeding images as the display color of lesion images and enlarges the display size of a lesion mark having the reddish display color with an increasing number x of bleeding images.

Except for the mark display control function to cause the mark display area 320 to display a lesion mark having the display size changed in accordance with the number x of bleeding images, the display controller 225b has the same functions as those of the display controller 215b in the aforementioned fifth embodiment.

Figure 29:
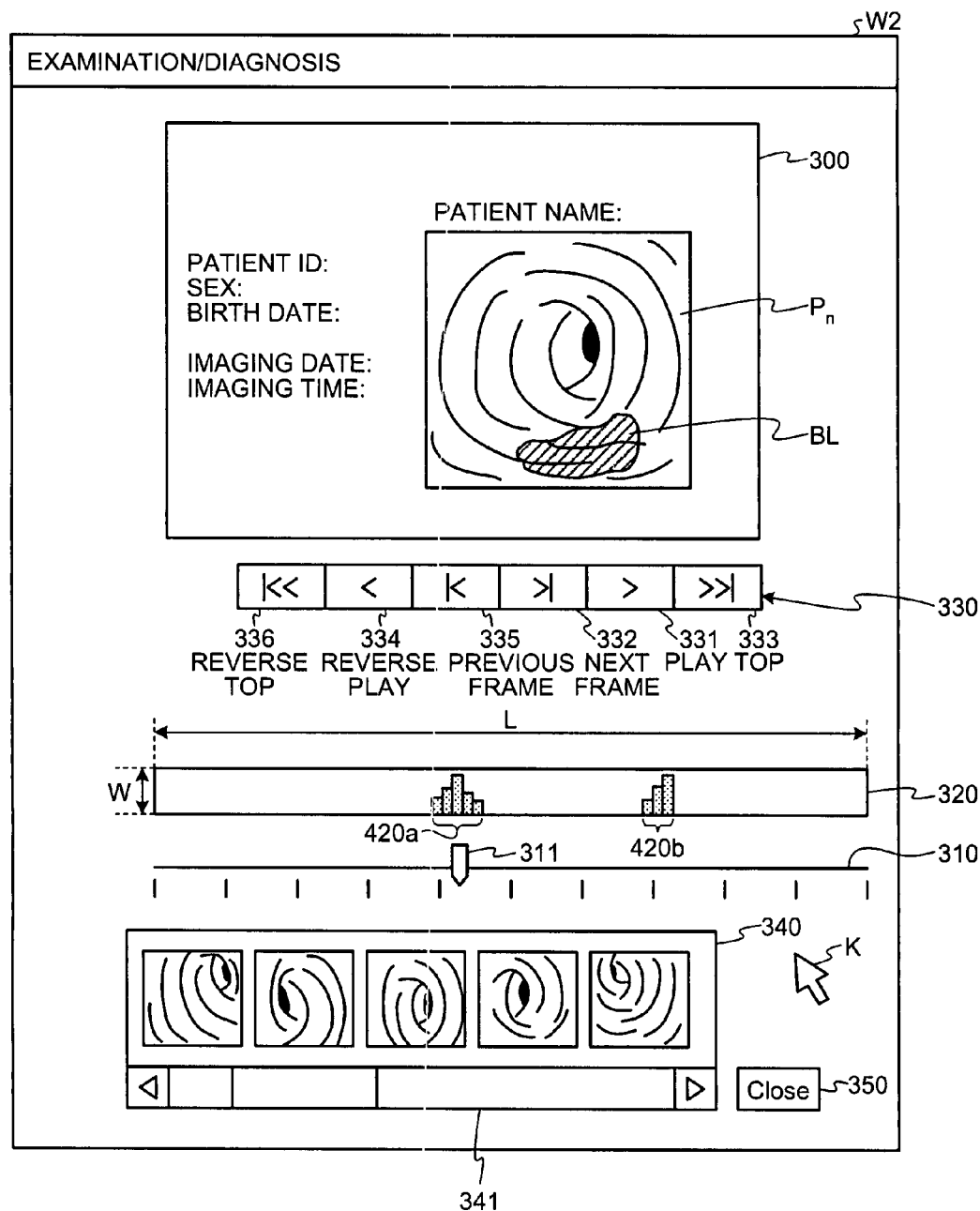
FIG. 29 is a schematic view exemplifying display content of the display unit of the image display device according to the fifth embodiment.

Next, a case in which a lesion image contained in all in vivo images AI is a bleeding image will be exemplified to concretely describe display content of the display unit 212 of the image display unit 220 according to the sixth embodiment of the present invention. FIG. 29 is a schematic view exemplifying display content of the display unit 212 of the image display device 220 according to the sixth embodiment.

As shown in FIG. 29, in the window W2 displayed in the display unit 212 of the image display device 220, the mark display area 320 displays lesion mark groups 420a and 420b containing one or more lesion marks having the display size in accordance with the number x of bleeding images instead of one or more lesion marks (for example, the aforementioned lesion marks 320a and 320b) having the display color in accordance with the number x of bleeding images in the continuous image group with N images. Like the aforementioned fifth embodiment, the mark display area 320 that displays the lesion mark groups 420a and 420b is formed of a group of (L×T) picture elements arranged like a grid within a rectangular area specified by the length L [picture elements] in the time axis direction and the width W [picture element unit] in a direction perpendicular to the time axis direction.

Other display content of the window W2 containing the mark display area 320 is the same as that of the aforementioned fifth embodiment.

Each of the lesion mark groups 420a and 420b contains a plurality of lesions marks displayed corresponding to the unit picture element of the time bar 310. Each of the plurality of lesion marks contained in the lesion mark groups 420a and 420b is formed of one or more picture elements contained in a picture element sequence (that is, picture element sequence in a direction perpendicular to the time axis of the time bar 310) in a longitudinal direction in the mark display area 320 and has the display size in accordance with the number x of bleeding images counted by the display controller 225b for each continuous image group with N images in all in vivo images AI.

The mark display area 320 that displays one or more lesion marks having a display mode exemplified by the aforementioned lesion mark groups 420a and 420b indicates the time position of each lesion image in all in vivo images AI along the time bar 310 and also functions as a time position display means for indicating distribution of the numbers of lesion images in the overall time positions (that is, the overall time positions indicated by the time bar 310) of all in vivo images AI. That is, the mark display area 320 indicates the time positions of one or more lesion images in all in vivo images AI on the time bar 310 by one or more lesion marks exemplified by the aforementioned lesion mark groups 420a and 420b and also indicates distribution of the numbers of lesion images in the overall time positions by a display mode (for example, the display size changed in accordance with the number of lesion images) of such lesion marks.

Figure 30:
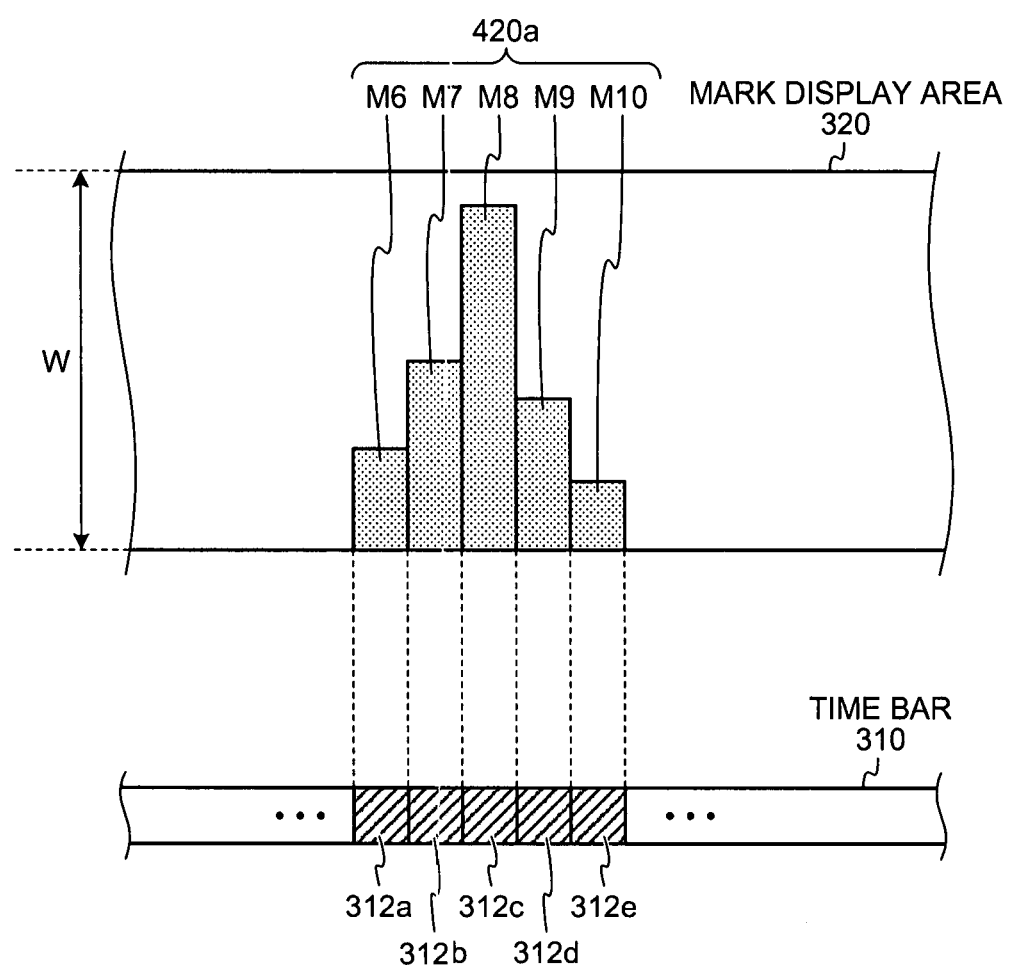
FIG. 30 is a schematic view showing a concrete example of a lesion mark which the display controller of the image display device according to the sixth embodiment causes the mark display unit to display.

Next, the aforementioned lesion mark group 420a in the mark display area 320 will be exemplified to describe in detail lesion marks displayed by the mark display area 320 based on control of the display controller 225b. FIG. 30 is a schematic view showing a concrete example of a lesion mark which the display controller 225b of the image display device 220 according to the sixth embodiment causes the mark display area 320 to display. FIG. 30 shows an enlarged view of the lesion mark group 420a displayed by the mark display area 320.

As shown in FIG. 30, the lesion mark group 420a contains, for example, five lesion marks M6 to M10 displayed along a picture element sequence in the time axis direction forming the time bar 310. The lesion marks M6 to M10 are displayed corresponding to the unit picture elements 312a to 312e of the time bar 310 respectively. The lesion marks M6 to M10 described above indicate the time positions of one or more bleeding images contained in each continuous image group with N images in all in vivo images AI represented by the unit picture elements 312a to 312e respectively.

More specifically, the lesion marks M6 to M10 are each formed of one or more picture elements contained in a group of picture elements in the mark display area 320 arranged one-dimensionally in a direction at right angles with respect to the time axis direction (that is, a picture element sequence in a direction perpendicular to the time axis of the time bar 310). In this case, one or more picture elements forming the lesion mark M6 are arranged in a direction at right angles with respect to the time axis direction (that is, the longitudinal direction of the mark display area 320) from one base of the mark display area 320 corresponding to the unit picture element 312a of the time bar 310. Similarly, one or more picture elements forming each of the lesion marks M7 to M10 are arranged in a direction at right angles with respect to the time axis direction from one base of the mark display area 320 corresponding to the unit picture elements 312b to 312e of the time bar 310 respectively.

The lesion mark M6 described above represents one or more bleeding images contained in the continuous image group (the aforementioned continuous image group with N images) in all in vivo images AI represented by the unit picture element 312a of the time bar 310 and also collectively shows the time position of bleeding images in the continuous image group represented by the unit picture element 312a. Similarly, the lesion marks M7 to M10 each represent one or more bleeding images contained in each continuous image group with N images represented by the unit picture elements 312b to 312e of the time bar 310 respectively and also collectively show the time positions of bleeding images in each continuous image group represented by the unit picture elements 312b to 312e respectively.

The display size of the lesion marks M6 to M10 changes depending on the number x of bleeding images in each continuous image group with N images represented by the unit picture elements 312a to 312e of the time bar 310 respectively. More specifically, the display size of each of the lesion marks M6 to M10 increases with an increasing number x of bleeding images in each continuous image group with N images represented by the unit picture elements 312a to 312e respectively and decreases with a decreasing number x of bleeding images. That is, the number of picture elements of each of the lesion marks M6 to M10 at right angles with respect to the time axis of the time bar 310 increases with an increasing number x of bleeding images in each continuous image group with N images represented by the unit picture elements 312a to 312e respectively and decreases with a decreasing number x of bleeding images. In this case, an upper limit of the number of picture elements of each of the lesion marks M6 to M10 is the same as the width W [picture elements] of the mark display area 320.

The lesion marks M6 to M10 described above indicate the time positions of bleeding images for each continuous image group with N images in all in vivo images AI containing one or more bleeding images and also shows distribution of the numbers of bleeding images for each continuous image group with N images by the display size thereof (the number of picture elements of a lesion mark changing up to the width W as an upper limit). This also applies to the lesion mark group 420b.

The display color of lesion marks (for example, the lesion marks M6 to M10) whose display size changes in accordance with the number x of bleeding images may be a desired color, as described above, but a reddish color corresponding to a bleeding site shown by bleeding images is desirable. This is because a bleeding site shown by bleeding images can be made more easily associable by setting the display color of lesion mark to reddish.

Lightness of the background of the mark display area 320 displaying such lesion marks (that is, the rectangular area specified by the length L and width W) has desirably an approximately mean value between lightness of a lesion mark and that of the background of the window W2 and the background color of the mark display area 320 is desirably a complementary color of the lesion mark. This makes the boundary between the background of the mark display area 320 and lesion marks clear, and as a result, lesion marks can be displayed by the mark display area 320 in such an aspect that can easily be confirmed visually by a user such as a physician and nurse.

Figure 31:
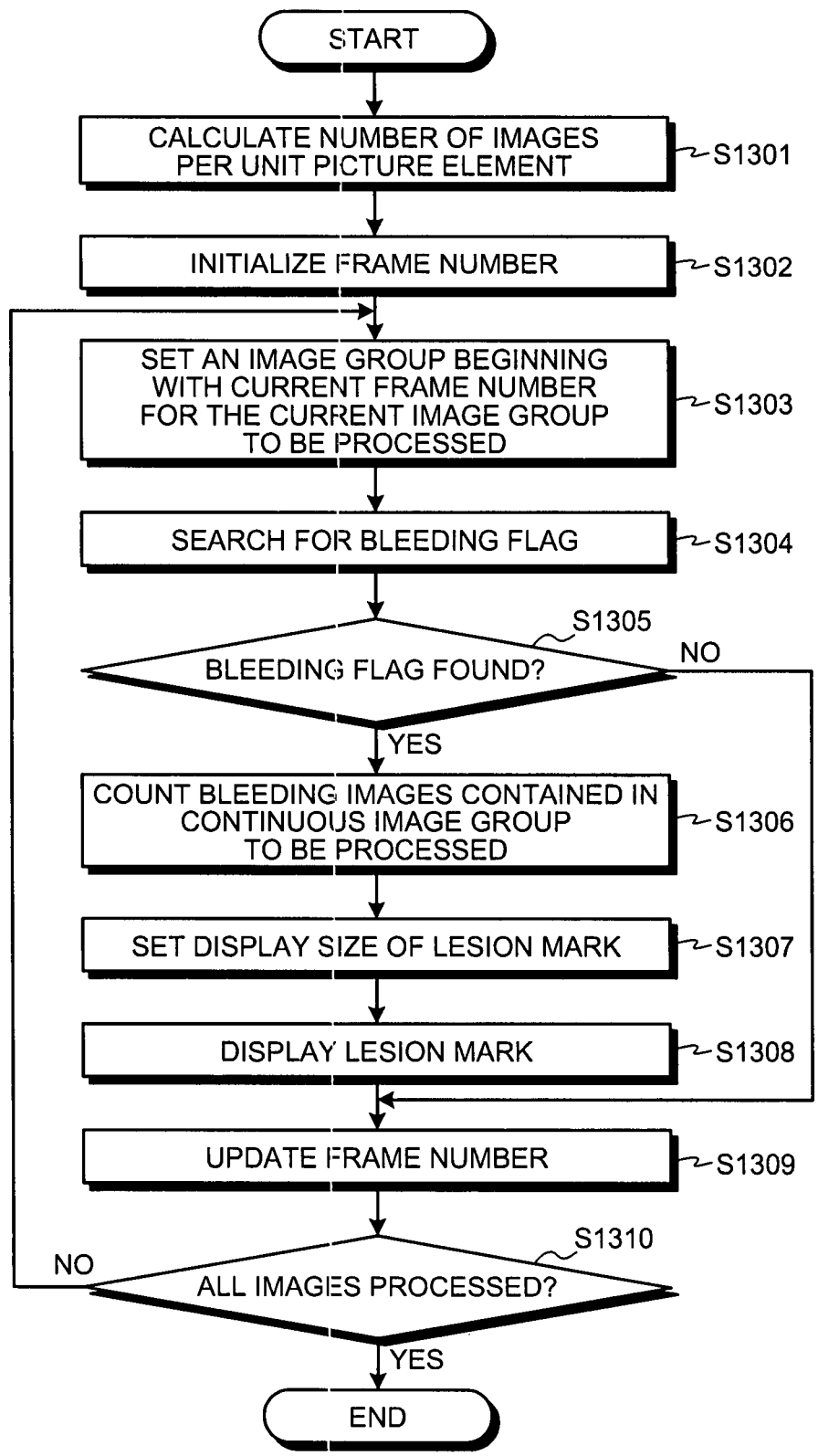
FIG. 31 is a flow chart showing an example of the processing procedure of the control unit performing control to display a lesion mark having a display size corresponding to a counting result of bleeding images.

Next, a case in which a bleeding image as an example of a lesion image is contained in all in vivo images AI will be exemplified to describe an operation of the control unit 225 that performs control to display a lesion mark indicating the time position of bleeding images in all in vivo images AI. FIG. 31 is a flow chart showing an example of the processing procedure of the control unit 225 performing control to display a lesion mark having the display size corresponding to a counting result of bleeding images.

By performing approximately the same processing procedure as that of the aforementioned steps S1201 to S1210 (See FIG. 26), the control unit 225 counts the number x of bleeding images in each continuous image group with N images contained in all in vivo images AI displayed in the main display area 300 to cause the mark display area 320 to display each lesion mark having the display size in accordance with a counting result of the number x of bleeding images. In this case, instead of the processing procedure of the aforementioned steps S1207 and S1208, the control unit 225 sets the display size in accordance with the number x of bleeding images in a continuous image group with N images, which is the continuous image group to be processed, and cause the mark display area 320 to display a lesion mark having the set display size.

More specifically, as shown in FIG. 31, like the aforementioned steps S1201 to S1204, the display controller 225*b* calculates the number N of images per unit picture element of the time bar 310 (step S1301), initializes the frame number n of all in vivo images AI (step S1302), determines a continuous image group in all in vivo images AI with N continuous images as the continuous image group to be processed (step S1303), and searches for bleeding flags in the continuous image group with N images, which is the continuous image group to be processed (step S1304).

Then, like the aforementioned steps S1305 and S1306, the display controller 225*b* determines whether there is any bleeding flag in the continuous image group with N images (step S1305) and, if it is determined that there is a bleeding flag (step S1305, Yes), counts the number of bleeding images contained in the continuous image group with N images (step S1206) to obtain the number x of bleeding images in the continuous image group with N images, which is the image group to be processed.

Next, the display controller 225*b* sets the display size of the lesion mark indicating the time position of one or more bleeding images contained in the continuous image group with N images (step S1307) corresponding to the number x of bleeding images obtained in step S1306. The display controller 225*b* uses the number x of bleeding images in the continuous image group with N images to calculate the number of picture elements of a picture element sequence forming a lesion mark and sets the obtained number of picture elements as the display size of the lesion mark.

More specifically, the display controller 225*b* calculates a display size $T_x$ [picture elements] of a lesion mark indicating the time position of one or more bleeding images contained in the continuous image group with N images based on, for example, the following formula (4) containing the number N of images in the continuous image group to be processed, the number x of bleeding images in the continuous image group with N images, and the width W of the mark display area 320 as variables. The display size $T_x$ is the number of picture elements in the picture element sequence forming the lesion mark. The display controller 225*b* sets the obtained display size $T_x$ as the display size of the lesion mark.

$$T_x = 10 + (\text{width } W - 10) \times (\text{bleeding image number } x / \text{image number } N) \quad (4)$$

Here, the display size $T_x$ (that is, the number of picture elements in the lesion mark) calculated based on the formula (4) increases with an increasing number x of bleeding images in the continuous image group with N images and decreases with a decreasing number x of bleeding images. By setting the display size of a lesion mark based on the formula (4), the display controller 225*b* changes the display size of a lesion mark in accordance with the number x of bleeding images in the continuous image group with N images.

Next, the display controller 225*b* controls the display unit 212 to display a lesion mark having the display size set in step S1307 (step S1308). More specifically, the display controller 225*b* performs control to display a lesion mark having the display size $T_x$ in accordance with the number x of bleeding images in the continuous image group with N images at the time position in the mark display area 320 corresponding to the unit picture element of the time bar 310 representing the continuous image group with N images. Based on the control of the display controller 225*b*, the mark display area 320 displays a lesion mark formed by a picture element sequence of the display size $T_x$ at the time position corresponding to the unit picture element of the time bar 310 representing the continuous image group with N images.

Subsequently, like the aforementioned step S1209, the display controller 225*b* updates the frame number n of all in vivo images AI displayed in the main display area 300 (step S1309). Then, like the aforementioned step S1210, the display controller 225*b* determines whether processing of all images in all in vivo images AI has been completed (step S1310) and, if it is determined that processing of at least one image contained in all in vivo images AI has not been completed (step S1310, No), returns to step S1303 to repeat the processing procedure of step S1303 and thereafter.

If, on the other hand, the display controller 225*b* determines that processing of all images contained in all in vivo images AI has been completed (step S1310, Yes), the display controller 225*b* terminates lesion mark display processing for all in vivo images AI. In this state, the mark display area 320 displays a lesion mark having the display size $T_x$ in accordance with the number x of bleeding images for each continuous image group containing one or more bleeding images from among continuous image groups with N images contained in all in vivo images AI.

If, in the aforementioned step S1305, the display controller 225*b* determines that there is no bleeding flag (step S1305, No), the display controller 225*b* proceeds to step S1309 without performing the processing procedure of steps S1306 to S1308. In this case, the display controller 225*b* has not detected any bleeding flag in the continuous image group with N images in the aforementioned step S1304. That is, the continuous image group with N images contains no bleeding image. If the continuous image group with N images contains no bleeding image, no lesion mark is made to be displayed by the display controller 225*b* at the time position in the mark display area 320 corresponding to the unit picture element of the time bar 310 representing the continuous image group with N images.

Figure 32:
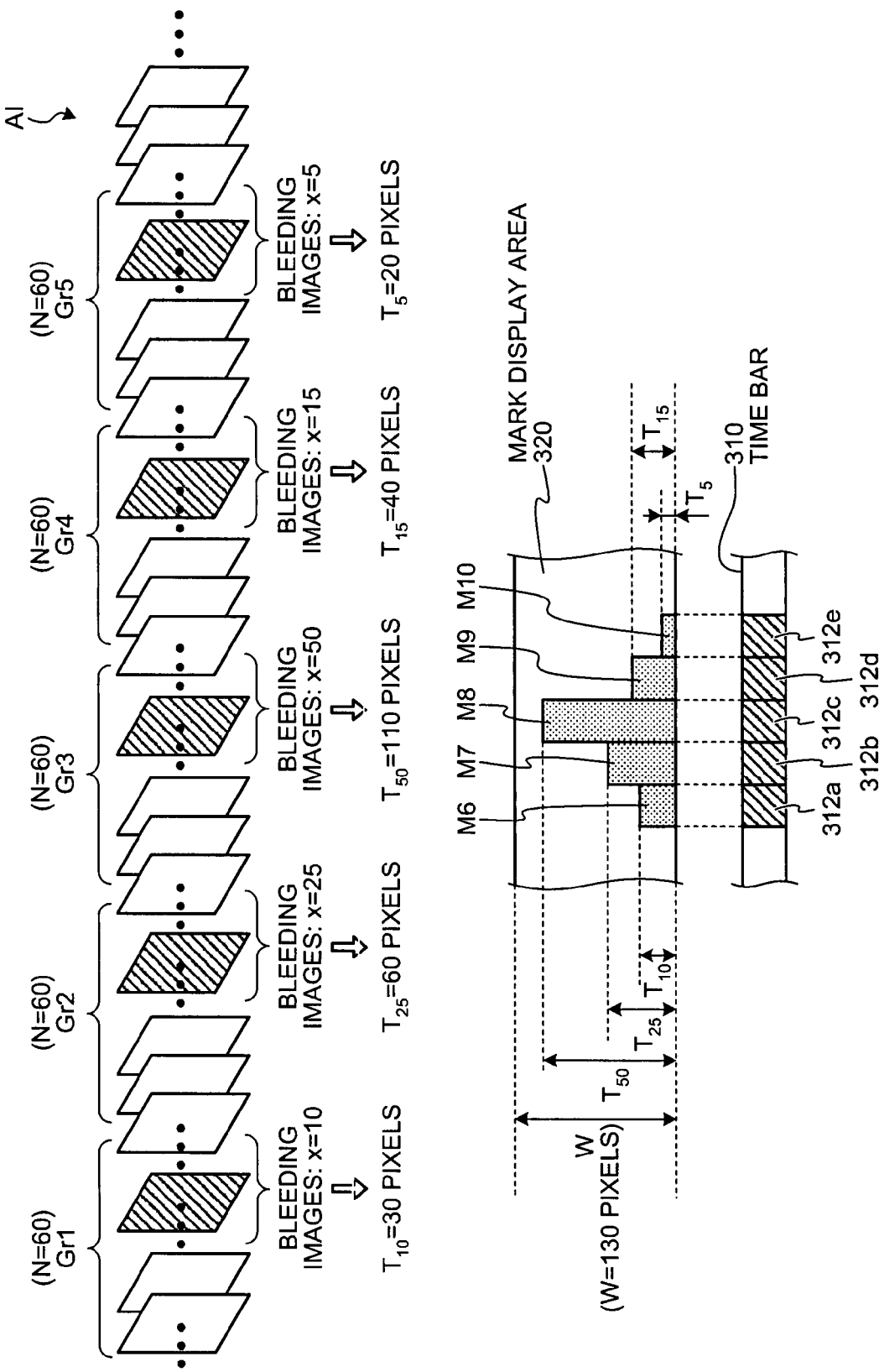
FIG. 32 is a schematic view concretely illustrating an operation of the display controller performing control to display the lesion mark having the display size in accordance with the number of bleeding images.

Next, the lesion marks M6 to M10 (See FIGS. 29 and 30) indicating the time positions of bleeding images contained in all in vivo images AI will be exemplified to concretely describe an operation of the display controller 225*b* that performs control to display a lesion mark having the display size in accordance with the number x of bleeding images for each continuous image group containing one or more bleeding images in all in vivo images AI. FIG. 32 is a schematic view concretely illustrating an operation of the display controller 225$b$ performing control to display the lesion mark having the display size $T_x$ in accordance with the number x of bleeding images.

All in vivo images AI inside the subject 1 displayed in the main display area 300 is, for example, a group of images of 60,000 frames (that is, a group of images whose total number A of images is 60,000 frames) and contains a plurality of bleeding images. If, here, the length L of the time bar 310 (that is, the number of picture elements in the time axis direction forming the time bar 310) is 1,000 picture elements, the display controller 225$b$ divides the total number A of images (=60,000 frames) in all in vivo images AI by the length L (=1,000 picture elements) of the time bar 310 to calculate the number N of images (=60 frames) per unit picture element of the time bar 310. The width W of the time bar 310 (that is, the upper limit of the display size of a lesion mark) is, for example, 130 picture elements.

Subsequently, the display controller 225$b$ determines a continuous image group one by one in all in vivo images AI in which N images corresponding to the unit picture element are continuous and counts the number x of bleeding images in each continuous image group with N images. Then, the display controller 225$b$ performs control to display a lesion mark having the display size $T_x$ in accordance with the number x of bleeding images for each continuous image group containing one or more bleeding images in all in vivo images AI.

More specifically, as shown in FIG. 32, the display controller 225$b$ determines the image group Gr1 of 60 frames in which as many images as the number N of images (=60 frames) corresponding to the unit picture element are continuous from among all in vivo images AI. The continuous image group Gr1 is represented, like the aforementioned fifth embodiment, by the unit picture element 312$a$ of the time bar 310.

Like the aforementioned fifth embodiment, the display controller 225$b$ detects 10 bleeding flags from the continuous image group Gr1 and counts the number of detected bleeding flags (=10) as the number x of bleeding images in the continuous image group Gr1. In this way, the display controller 225$b$ obtains the number x=10 of bleeding images in the continuous image group Gr1.

If 10 frames of bleeding images are contained in the continuous image group Gr1, the display controller 225$b$ sets the display size of a lesion mark in accordance with the number x=10 of bleeding images in the continuous image group Gr1. More specifically, the display controller 225$b$ calculates the display size $T_{10}$ (=30 picture elements) in accordance with the number x=10 of bleeding images based on the aforementioned formula (4) and sets the obtained display size $T_{10}$ as the display size of the lesion mark indicating the time position of bleeding images in the continuous image group Gr1.

The display controller 225$b$ performs control to display the lesion mark M6 having the display size $T_{10}$ (=30 picture elements) set as described above at the time position in the mark display area 320 corresponding to the unit picture element 312$a$. Based on the control of the display controller 225$b$, the mark display area 320 displays the lesion mark M6 at the time position corresponding to the unit picture element 312$a$.

Subsequently, like the aforementioned fifth embodiment, the display controller 225$b$ determines the continuous image groups Gr2 to Gr5 one by one in all in vivo images AI in which as many images as the number N (=60) of images per unit picture element of the time bar 310 are continuous and counts the number x of bleeding images in each of the determined continuous image groups Gr2 to Gr5. Then, approximately similarly to the aforementioned lesion mark M6, the display controller 225$b$ performs control to display the lesion marks M7 to M10 having each display size $T_x$ in accordance with the number x of bleeding images of the continuous image groups Gr2 to Gr5 respectively.

Like the aforementioned fifth embodiment, the continuous image groups Gr2 to Gr5 are continuous image groups of 60 frames represented by the unit picture elements 312$b$ to 312$e$ of the time bar 310 respectively and each of the continuous image groups Gr2 to Gr5 contains one or more bleeding images.

Like the aforementioned fifth embodiment, the display controller 225$b$ obtains the number x=25 of bleeding images of the continuous image group Gr2, the number x=50 of bleeding images of the continuous image group Gr3, the number x=15 of bleeding images of the continuous image group Gr4, and the number x=5 of bleeding images of the continuous image group Gr5 one by one. The display controller 225$b$ described above sets, based on the aforementioned formula (4), the display size $T_{25}$ (=60 picture elements) of the lesion mark M7 in accordance with the number x=25 of bleeding images of the continuous image group Gr2, the display size $T_{50}$ (=110 picture elements) of the lesion mark M8 in accordance with the number x=50 of bleeding images of the continuous image group Gr3, the display size $T_{15}$ (=40 picture elements) of the lesion mark M9 in accordance with the number x=15 of bleeding images of the continuous image group Gr4, and the display size $T_5$ (=20 picture elements) of the lesion mark M10 in accordance with the number x=5 of bleeding images of the continuous image group Gr5 one by one.

The display controller 225$b$ performs control to display the lesion marks M7 to M10 having the display size $T_x$ in accordance with the number x of bleeding images at each time position in the mark display area 320 corresponding to the unit picture elements 312$b$ to 312$e$ one by one respectively. Based on the control of the display controller 225$b$, the mark display area 320 displays the lesion marks M7 to M10 at each time position corresponding to the unit picture elements 312$b$ to 312$e$ one by one respectively.

Here, the lesion marks M6 to M10 displayed based on the control of the display controller 225$b$ represent each group of bleeding images contained in the continuous image groups Gr1 to Gr5 respectively. The lesion mark M6 having the display size $T_{10}$ (=30 picture elements) is formed by a picture element sequence of 30 picture elements arranged in the longitudinal direction of the mark display area 320 from one base of the mark display area 320 at the time position in the mark display area 320 corresponding to the unit picture element 312$a$. The lesion mark M7 having the display size $T_{25}$ (=60 picture elements) is formed by a picture element sequence of 60 picture elements arranged in the longitudinal direction of the mark display area 320 from one base of the mark display area 320 at the time position in the mark display area 320 corresponding to the unit picture element 312$b$. The lesion mark M8 having the display size $T_{50}$ (=110 picture elements) is formed by a picture element sequence of 110 picture elements arranged in the longitudinal direction of the mark display area 320 from one base of the mark display area 320 at the time position in the mark display area 320 corresponding to the unit picture element 312$c$. The lesion mark M9 having the display size $T_{15}$ (=40 picture elements) is formed by a picture element sequence of 40 picture elements arranged in the longitudinal direction of the mark display area 320 from one base of the mark display area 320 at the time position in the mark display area 320 corresponding to the unit picture element 312$d$. The lesion mark M10 having the display size $T_5$ (=20 picture elements) is formed by a picture element sequence of 20 picture elements arranged in the longitudinal direction of the mark display area 320 from one base of the mark display area 320 at the time position in the mark display area 320 corresponding to the unit picture element 312*e*.

Each display size $T_x$ of the lesion marks M6 to M10 increases with an increasing number x of bleeding images in the aforementioned continuous image groups Gr1 to Gr5. More specifically, the display size $T_{50}$ of the lesion mark M8 representing bleeding images of the number x=50 of bleeding images is larger than the lesion marks M6, M7, M9, and M10 representing less than 50 bleeding images. The display size $T_{25}$ of the lesion mark M7 representing bleeding images of the number x=25 of bleeding images is larger than the lesion marks M6, M9, and M10 representing less than 25 bleeding images. The display size $T_{15}$ of the lesion mark M9 representing bleeding images of the number x=15 of bleeding images is larger than the lesion marks M6, and M10 representing less than 15 bleeding images. The display size $T_{10}$ of the lesion mark M6 representing bleeding images of the number x=10 of bleeding images is larger than the lesion mark M10 representing less than 10 bleeding images.

The lesion marks M6 to M10 described above indicate each time position of bleeding images contained in the continuous image groups Gr1 to Gr5 along the time bar 310 respectively and also can indicate distribution of the numbers of bleeding images in the continuous image groups Gr1 to Gr5 along the time bar 310 by each display size $T_x$. In this case, the lesion marks M6 to M10 can indicate more or less of the number of bleeding images when compared among the continuous image groups Gr1 to Gr5 by a difference in display size $T_x$ among lesion marks.

A user such as a physician and nurse can understand over which time position of the overall time positions of all in vivo images AI bleeding images are distributed based on the display positions of the lesion marks M6 to M10 displayed along the time bar 310. At the same time, the user can easily understand distribution of the numbers of bleeding images in the overall time positions of all in vivo images AI based on the display size of the lesion marks M6 to M10 and also more or less of the number of bleeding images when compared among time positions of such bleeding images.

As has been described, in the sixth embodiment of the present invention, the image display device is configured in such ways that, instead of the aforementioned display color of lesion marks, the display size of each lesion mark is changed in accordance with the number of bleeding images counted for each continuous image group in which so many images as to correspond to the unit picture element of a time bar are continuous and a lesion mark having the display size in accordance with the number of bleeding images is displayed. Otherwise, the configuration is the same as that of the fifth embodiment. Thus, operation effects of the aforementioned fifth embodiment can be gained, and also distribution of the numbers of lesion images in the overall time positions of a group of images inside organs picked up in a time series can be displayed in such a display mode as to make visual confirmation still easier and an image display device that enables a user to understand distribution of the numbers of bleeding images more easily can be realized.

In the first to fourth embodiments of the present invention, a bleeding site or fading site is exemplified as a lesion contained as a photographic object of lesion images, but these embodiments are not limited to this and lesions indicated by such lesion images may be various kinds of lesions that could develop in a living body including a flare site, clotted blood site, erosion site, and ulcer site, in addition to the bleeding site and fading site.

In the second to fourth embodiments of the present invention, a bleeding site and fading site are exemplified as multiple kinds of lesions, but these embodiments are not limited to this and may be various kinds of lesions that could develop in a living body including a bleeding site, fading site, flare site, clotted blood site, erosion site, and ulcer site. In this case, like the aforementioned case of a bleeding image and fading image, the lesion detector 25*b* may determine whether an image is a lesion image based on color information (such as the average color and RGB color element values) of the image and, if it is determined that the image is a lesion image, attach a lesion flag corresponding to the lesion (such as a bleeding site, fading site, flare site, clotted blood site, erosion site, and ulcer site) indicated by the lesion image. The lesion color of the aforementioned lesion mark and the slider 111 may be set to a different color for each of the multiple kinds of lesions.

Further, in the third and fourth embodiments of the present invention, at least one of a bleeding site and fading site is selected, but these embodiments are not limited to this and one or more lesions selected by the lesion selector 160 may be allowed if such lesions include at least one of various kinds of lesions that could develop in a living body including a bleeding site, fading site, flare site, clotted blood site, erosion site, and ulcer site. In this case, the selection menu of the lesion selector 160 may add multiple kinds of lesions such as bleeding site, fading site, flare site, clotted blood site, erosion site, and ulcer site as selection choices.

Also, in the first to fourth embodiments of the present invention, display color information for setting the lesion color corresponding to a lesion indicated by lesion images (that is, the lesion colors of the aforementioned lesion marks and the slider 111) and the default color of the slider 111 is stored in the storage unit 14 in advance and the lesion color set based on the display color information is adopted as the lesion color for the lesion mark and the slider 111, but these embodiments are not limited to this and the lesion color for the lesion mark and the slider 111 is desirably a color that closely resembles that of a lesion indicates by lesion images or may be the average color of lesion images.

Further, in the second to fourth embodiments of the present invention, a plurality of lesion marks indicating each of the time positions of a plurality of lesion images contained in all in vivo images AI are displayed in the one mark display area 120, but these embodiments are not limited to this and a plurality of mark display units may be provided for each kind of lesions so that the plurality of mark display units can display each of the plurality of lesion marks classified for each kind of lesions.

Also, in the first to fourth embodiments of the present invention, one or more lesion images in all in vivo images AI are detected when capturing all in vivo images AI from the portable recording medium 5, but these embodiments are not limited to this and all in vivo images AI captured from the portable recording medium 5 may be stored in the storage unit 14 so that one or more lesion images contained in all in vivo images AI in the storage unit 14 can thereafter be detected. In this case, in the aforementioned third and fourth embodiments, among lesions images contained in all in vivo images AI, one or more lesion images containing the lesion selected by the lesion selector 160 as a photographic object may be selected from all in vivo images AI.

Further, in the first to fourth embodiments of the present invention, when a lesion image is currently displayed in the main display area 100, the display color of the slider 111 indicating the time position of the lesion image is changed to a lesion color, but these embodiments are not limited to this and the display color of the slider 111 may be displayed in a predetermined color (for example, the default color) regardless of the image currently displayed in the main display area 100. That is, the display color of the slider 111 may not be changed.

Also, is the fifth embodiment of the present invention, the display color of a lesion mark in accordance with the number x of bleeding images is set based on the aforementioned formulae (1) to (3), but the formulae (1) to (3) are only an example of calculation formulae of each color element (R value, G value, B value) forming the display color of a lesion mark in accordance with the number x of bleeding images and do not limit the present invention.

More specifically, the calculation formula of the R value forming the display color of a lesion mark is not limited to the aforementioned formula (1) and any calculation formula will do that includes the number of lesion images exemplified by the number x of bleeding images as a variable and provides an R value in the range of 0 to 255 in accordance with the number of lesion images. In this case, coefficients and constants in each term of the calculation formula of the R value may have desired numerical values, but it is desirable that such coefficients and constants are set so that changes in depth of red caused by changes in the number of lesion images are a linear change for human visual perception.

Also, in the fifth embodiment of the present invention, the display color of a lesion mark is set to red (that is, $1 \le R$ value $\le 255$, G value=0, B value=0) corresponding to a bleeding site indicated by bleeding images and depth of the display color (red) of the lesion mark is changed as the number x of bleeding images changes, but the present embodiment is not limited to this and the display color of a lesion mark may be set to a color formed by combining at least two of the three color elements R, G, and B so that color information such as a hue, lightness, and chroma of the display color of the lesion mark is changed as the number of lesion images exemplified by the number x of bleeding images changes. In this case, after setting at least two of the three color element values (R value, G value, B value) to numerical values equal to or greater than 1, each value of at least two color elements may be changed within the range of numerical values of 1 to 255 as the number of lesion images changes.

Further, in the fifth embodiment of the present invention, the value of a color element (R value) forming the display color of a lesion mark is changed linearly with the number x of bleeding images, but the present embodiment is not limited to this and the values of color elements (R value, G value, B value) forming the display color of a lesion mark may be changed non-linearly with respect to the number of lesion images such as the number x of bleeding images. In this case, the calculation formula of the color element values forming the display color of the lesion mark may be formed by a multidimensional function containing the number of lesion images as a variable. If a color formed by combining at least two of the three color elements R, G, and B is set as the display color of a lesion mark, at least two of the three calculation formulae of the R value, G value, and B value may be formed by multidimensional functions containing the number of lesion images as a variable. In addition, such multidimensional functions are desirably set so that changes in display color (for example, changes in hue, lightness, chroma, and depth) caused by a changing number of lesion images are a linear change for human visual perception.

Also, in the sixth embodiment of the present invention, the display size $T_x$ of a lesion mark in accordance with the number x of bleeding images is set based on the aforementioned formula (4), but the formula (4) is an example of a calculation formula for calculating the display size $T_x$ of a lesion mark in accordance with the number x of bleeding images and does not limit the present invention.

More specifically, the calculation formula of the display size $T_x$ of a lesion mark is not limited to the aforementioned formula (4) and any calculation formula will do that includes the number of lesion images exemplified by the number x of bleeding images as a variable and provides the number of picture elements in the range of 0 to W picture elements, (corresponding to the width W of the mark display area 320) in accordance with the number of lesion images. In this case, coefficients and constants in each term of the calculation formula of the display size $T_x$ may have desired numerical values, but it is desirable that such coefficients and constants are set so that changes in display size $T_x$ caused by changes in the number of lesion images are a linear change for human visual perception.

Also, in the sixth embodiment of the present invention, the display size $T_x$ of a lesion mark is changed linearly with the number x of bleeding images, but the present embodiment is not limited to this and the display size $T_x$ of a lesion mark may be changed non-linearly with the number of lesion images such as the x of bleeding images. In this case, the calculation formula of the display size $T_x$ of a lesion mark may be formed by a multidimensional function containing the number of lesion images as a variable. In addition, such a multidimensional function is desirably set so that a change in display size $T_x$ caused by a changing number of lesion images is a linear change for human visual perception.

Further, in the fifth and sixth embodiments of the present invention, a bleeding site is exemplified as a lesion indicated by a lesion image (that is, a lesion contained in a lesion image as a photographic object), but these embodiments are not limited to this and lesions indicated by such a lesion image may be various kinds of lesions that could develop in a living body including a fading site, flare site, clotted blood site, erosion site, and ulcer site, in addition to the bleeding site. The display color of a lesion mark indicating the time position of such a lesion image is desirably a color corresponding to the lesion indicated by such lesion images (such as a bleeding site, fading site, flare site, clotted blood site, erosion site, and ulcer site). More specifically, if the lesion indicated by a lesion image is a bleeding site, flare site, or clotted blood site, the display color of a lesion mark indicating the time position of such images is desirably reddish. If the lesion indicated by a lesion image is a fading site, erosion site, or ulcer site, the display color of a lesion mark indicating the time position of such images is desirably white or gray.

Also, in the fifth and sixth embodiments of the present invention, one or more lesion images in all in vivo images AI are detected when capturing all in vivo images AI from the portable recording medium 205, but these embodiments are not limited to this and all in vivo images AI captured from the portable recording medium 205 may be stored in the storage unit 214 so that one or more lesion images contained in all in vivo images AI in the storage unit 214 can thereafter be detected.

Figure 33:
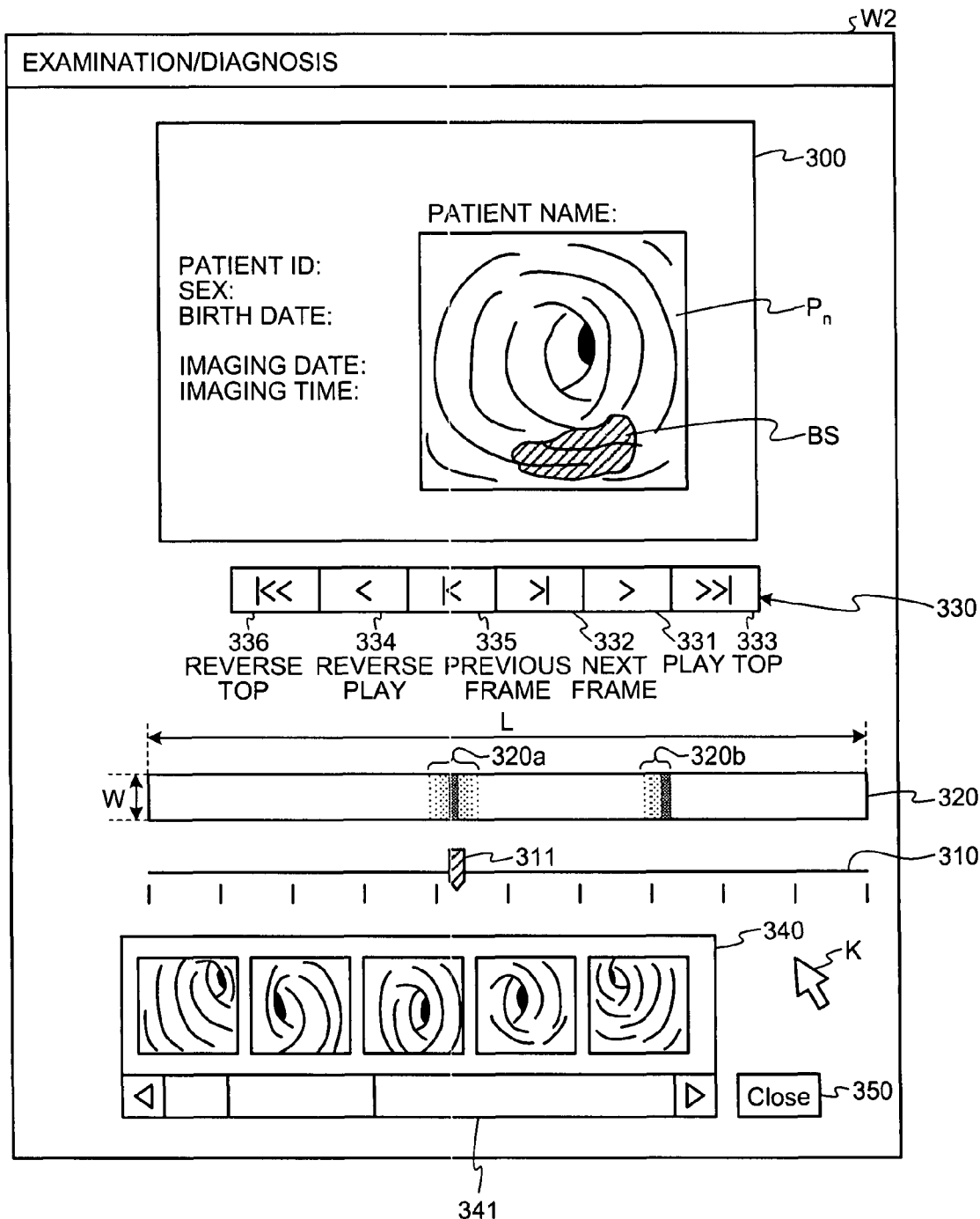
FIG. 33 is a schematic view exemplifying the display contents of the display unit of the image display device which display unit displays a group of lesion marks having the display mode responsive to the number of lesion images and a slider whose color has changed to the lesion color.

Further, in the fifth and sixth embodiments of the present invention, the display color of the slider 311 is not changed before or after displaying a lesion image in the main display area 300, but these embodiments are not limited to this and, as exemplified in the aforementioned first to fourth embodiments, if a lesion image is currently displayed in the main display area 300, the display color of the slider 311 indicating the time position of the lesion image may be changed to a lesion color. That is, the aforementioned first to fourth embodiments and the fifth and sixth embodiments may suitably be combined. In this case, the display controller of the image display device according to the aforementioned fifth or sixth embodiment (that is, the display controller 215b, 225b) has approximately the same control function as the display controllers 15a, 25a, 35a, and 45a of the image display device according to the first to fourth embodiments and if a lesion image is currently displayed in the main display area 300, as shown in FIG. 33 for example, control to change the display color of the slider 311 indicating the time position of the lesion image from the default color to a lesion color (more particularly, a lesion color corresponding to the lesion indicated by the lesion image) may be performed.

<Various Modifications>

The above described embodiments are only for the purpose of describing the principles of the invention. Therefore, various variations and modifications of the above embodiments are apparent to those skilled in the art.

For example, in the above-described embodiments, the color of the slider is changed depending on whether the current in vivo image currently displayed in the main display area is a lesion image. However, since one of the purposes of the invention is achieved as long as the slider is displayed such that a change in the display mode of the slider can be visually recognized, any display mode of the slider may be changed. For example, any one or combination may be changed of color, shape, filling pattern, blink, blinking pattern and blinking frequency of the slider.

Also, in the above-described embodiments, both of the time bar and the mark display area are used. However, the time bar and the mark display area are not necessarily discriminated from each other. Even if it were not for the time bar, a slider movable along the mark display area will suffice. In this case, only the time scale of the time bar may be displayed along and adjacent to the mark display area if necessary or even must not be displayed. Alternatively, instead of displaying the slider, the pixels located in the time position corresponding to the current in vivo image in the mark display area may be made to emit light either by differentiating the luminance or the color thereof from that of the other pixels or by blinking the pixels located in the time position such that the pixels in the time position can be visually differentiated from the other pixels.

Though in the fifth and sixth embodiments it is assumed that the total number A of all in vivo images is inter times the pixel number L of the long side of the mark display area, the total number A has not necessarily to be inter times the pixel number L. If the total number A is not inter times the pixel number L, L continuous image groups into which all in vivo images are divided by the pixel number L may be determined, and the L continuous image groups may be mapped one-to-one onto respective L time positions.

In connection with setting the color of the lesion mark in step S1207 in the fifth embodiment, the description has been done as if a continuous image group includes one or more lesion images for lesions of only one kind. However, a continuous image group may include lesion images for lesions of a plurality of kinds. In order to cope with such a situation, lesion display colors are preferably assigned to respective kinds of lesions; and if a continuous image group includes lesions of only one kind, then the color density of the lesion mark for the continuous image group may be controlled according to the equation (1) or if a continuous image group includes lesions of a plurality of kinds, then a color component for each lesion color is calculated from an equation similar to equation (1) and the mixture of the calculated color components may be set for the color of the lesion mark for the continuous image group.

Also, in the above-described embodiments, the mark display area has been a horizontally elongated area, but may be a vertically elongated area. Further, the mark display area has not necessarily to be a straight bar, and may be of an L shape or even rectangular as long as the start point and the end point are definitely defined. Alternatively, the display screen may be provided with a display area in which a schematic diagram showing a simplified gastrointestinal (GI) tract through which the capsule endoscope travels; and the GI tract portion of the schematic diagram may be used as the mark display area, or the lesion marks may be displayed on the GI tract portion (together with another slider if necessary) as well as the above-described mark display area. Doing this makes it possible to identify not only the time position but also the location in the GI tract of each lesion.

We have focused the description on an image display device for displaying in vivo images obtained through a capsule endoscope which automatically outputs in vivo images at predetermined time intervals. However, the principles of the invention is also applicable to the display of in vivo images obtained through an endoscope of such a type as requires the user to shoot. Though the time intervals between adjacent ones of all in vivo images are not constant, all in vivo images can be expressed and managed by using a mark display area and a time bar having both ends thereof set for the first in vivo image and the last in vivo image to share an identical time scale. In this case, since the time intervals between adjacent in vivo images are not constant, mapping all in vivo images onto a mark display area and/or a time bar results in the time scale or all in vivo images containing, in a mixed manner, time periods (or continuous image groups) of the first kind for which the time intervals between adjacent in vivo images (or the intervals between time positions of adjacent in vivo images in the time scale) are longer than a minimum unit period of time discriminable in the time scale (i.e., the interval between pixels in the time scale direction of the mark display area and the time bar), time periods (or continuous image groups) of the second kind for which the time intervals are equal to the minimum unit period and time periods (or continuous image groups) of the third kind for which the time intervals are shorter than the minimum unit period. As for the continuous image groups of the first and second kinds, the invention can be easily implemented by simply mapping such the continuous image groups onto the mark display area and/or the time bar. However, as for the continuous image groups of the third kind (or as for the continuous image groups or periods of the time scale for which the density of in vivo images is larger than the resolution in the direction of time bar), it is preferable to use techniques disclosed in connection with the fifth or sixth embodiment in order to implement the invention.

In an image display device according to the present invention, by visually confirming a display color of a slider indicating a time position of an image inside a subject currently displayed in a display area, whether the image inside the subject is a lesion image can easily be determined. As a result, an advantage of being able to easily identify lesion images such as a bleeding site from among a group of images inside the subject successively displayed in the display area without disturbing observation of the image inside the subject currently displayed in the display area can be obtained.

Also, in an image display device according to the present invention, a time position of a lesion image in overall time positions of a group of images inside a subject can be indicated by a display position of one or more lesion marks displayed along a time axis of a time bar and also distribution of the numbers of lesion images in the overall time positions can be indicated by a display mode (for example, the display color and display size) of one or more lesion marks. As a result, the time position of a lesion image contained in a group of images inside organs picked up in a time series can be understood and an advantage of being able to easily understand distribution of the numbers of lesion images in the overall time positions of the group of images inside organs can be obtained.

Further advantages and modifications will occur to those skilled in the art. Embodiments of the present invention are not limited by specific embodiments shown and described herein and thus various modifications may be made without departing from the spirit or scope of the inventive concept as defined by the appended claims and their equivalents.

As has been described above, an image display device according to the present invention is useful for examination inside a subject by observing each image picked up inside organs of the subject such as a patient. Particularly, lesion images among a group of images inside the subject displayed on a screen can easily be identified, or distribution of the numbers of lesion images in overall time positions of the group of images inside the subject can easily be understood, and as a result, the image display device according to the present invention is suitable as an image display device that enables a user to observe lesion images inside the subject easily and efficiently.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. An image display device for displaying in vivo images picked up inside a subject in a time series, comprising:
    an image detector for detecting a lesion image contained in vivo images picked up over the time series;
    a fundamental display unit for displaying an elongated display area having a scale assigned along a longitudinal direction thereof and an indicator which moves along the scale to indicate a position in the scale which corresponds to a current one of the all in vivo images which is currently displayed in a main display area;
    a lesion display unit, responsive to a detection of the lesion image by the image detector, for making pixels located at a position in the elongated display area which position corresponds to the lesion image to emit light in a predetermined pixel-display mode; and
    a display controlling unit for controlling a display mode of the indicator based on information on a lesion that is possible to be contained in the current in vivo image;
    wherein the fundamental display unit is adapted to respond to a determination that a total number of all in vivo images is larger than a pixel number L of pixels along a long side of the elongated display area, and to map L continuous image groups into which all in vivo images are divided by the pixel number onto L positions of the scale and display the indicator at a position corresponding to a continuous image group in which the current in vivo image is included, and wherein the lesion display unit includes:
    lesion mark display unit for making a pixel column at each position in the elongated display area to emit light quantitatively in response to a number of lesion images included in the continuous image group corresponding to the position.

2. The image display device according to claim 1, wherein the lesion mark display unit is adapted to make only a part of the pixel column which length is responsive to the number of lesion images to emit light.

3. The image display device according to claim 2, wherein one end of the part of the pixel column is on a lower long side of the elongated display area.

4. The image display device according to claim 3, wherein a color of the light is a color associated with the kind of lesions contained in the lesion images.

5. The image display device according to claim 2, wherein a color of the light is a color associated with the kind of lesions contained in the lesion images.

6. The image display device according to claim 1, wherein a color of the light is a color associated with the kind of lesions contained in the lesion images.

7. An image display device for displaying in vivo images picked up inside a subject in a time series, comprising:
    an image detector for detecting a lesion image contained in vivo images picked up over the time series;
    a display comprising:
        a fundamental display unit for displaying an elongated display area having a scale assigned along a longitudinal direction thereof and an indicator which moves along the scale to indicate a position in the scale which corresponds to a current one of the all in vivo images which is currently displayed in a main display area; and
        a lesion display unit, responsive to a detection of the lesion image by the image detector, for making pixels located at a position in the elongated display area which position corresponds to the lesion image to emit light in a predetermined pixel-display mode; and
    a controller for grouping the in-vivo images into a plurality of subsets, for counting a number of lesion images within each of the plurality of subsets and for controlling a display mode of the indicator based on a counting result of the number of lesion images within each of the plurality of subsets,
    wherein the lesion display unit displays a lesion mark for each of the plurality of subsets having a display mode based on the counting result of the number of lesion images.

8. The image display device according to claim 7, wherein the lesion display unit changes a display color of the lesion mark in accordance with the counting result of the number of lesion images.

9. The image display device according to claim 8, wherein the lesion display unit changes the display color of the lesion mark to be darker as the number of lesion images increases and changes the display color of the lesion mark to be lighter as the number of lesion images decreases.

10. The image display device according to claim 7, wherein the lesion display unit changes a display size of the lesion mark in accordance with the counting result of the number of lesion images.

11. The image display device according to claim 10, wherein the lesion display unit enlarges the display size of the lesion mark as the number of lesion images increases.

* * * * *